US008926633B2

(12) United States Patent
Carly

(10) Patent No.: US 8,926,633 B2

(45) Date of Patent: Jan. 6, 2015

(54) APPARATUS AND METHOD FOR DELIVERING A CLOSURE ELEMENT

(75) Inventor: Michael T. Carly, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 756 days.

(21) Appl. No.: 11/455,993

(22) Filed: Jun. 19, 2006

(65) Prior Publication Data

US 2007/0021778 A1 Jan. 25, 2007

Related U.S. Application Data

(60) Provisional application No. 60/693,531, filed on Jun. 24, 2005.

(51) Int. Cl.

*A61B 17/128* (2006.01)
*A61B 17/00* (2006.01)
*A61B 17/08* (2006.01)
*A61B 17/064* (2006.01)

(52) U.S. Cl.

CPC ........... *A61B 17/0057* (2013.01); *A61B 17/083* (2013.01); *A61B 17/0644* (2013.01); *A61B 2017/00336* (2013.01); *A61B 2017/00672* (2013.01); *A61B 2017/00867* (2013.01)

USPC ............ 606/139; 606/142; 606/213; 606/191

(58) Field of Classification Search

USPC ................. 606/232, 139–142, 151, 157–158, 606/191–195, 198

See application file for complete search history.

(56) References Cited

U.S. PATENT DOCUMENTS 287,046 A 10/1883 Norton
438,400 A 10/1890 Brennen
556,082 A 3/1896 Boeddinghaus
1,088,393 A 2/1914 Backus
1,242,139 A 10/1917 Callahan
1,331,401 A 2/1920 Summers (Continued)

FOREIGN PATENT DOCUMENTS

AU 2003297432 7/2004
CA 2 339 060 2/2000

(Continued)

OTHER PUBLICATIONS

PCT patent application No. PCT/US2006/024334, International Search Report mailed Jan. 16, 2007.

(Continued)

*Primary Examiner* — Elizabeth Houston

(74) *Attorney, Agent, or Firm* — Workman Nydegger; Randy Shen

(57) ABSTRACT

An apparatus for delivering and deploying a closure element to an opening formed in a body lumen, including a delivery assembly positionable through the tissue and into the opening. The delivery assembly includes a distal locator portion and a carrier portion oriented proximal to the distal locator portion. The distal locator portion is configured to selectably engage the body lumen adjacent to the opening, and the carrier portion is configured to carry and support the closure element in a substantially tubular configuration. The carrier portion is further configured to urge the closure element toward an expanded cross-sectional dimension for deployment thereof, such that the closure element is oriented to engage the tissue when deployed and, when released, to return to the natural, substantially planar configuration and the natural cross-section dimension wherein the engaged tissue is drawn substantially closed.

29 Claims, 14 Drawing Sheets

(56) References Cited

U.S. PATENT DOCUMENTS 1,426,111 A 8/1922 Sacker
1,480,935 A 1/1924 Gleason
1,516,990 A 11/1924 Silverman
1,596,004 A 8/1926 De Bengoa
1,647,958 A 11/1927 Ciarlante
1,847,347 A 3/1932 Maisto
1,852,098 A 4/1932 Anderson
1,880,569 A 10/1932 Weis
2,075,508 A 3/1937 Davidson
2,087,074 A 7/1937 Tucker
2,108,206 A 2/1938 Meeker
2,210,061 A 8/1940 Caminez
2,254,620 A 9/1941 Miller
2,316,297 A 4/1943 Southerland et al.
2,371,978 A 3/1945 Perham
2,453,227 A 11/1948 James
2,583,625 A 1/1952 Bergan
2,610,631 A 9/1952 Calicchio
2,684,070 A 7/1954 Kelsey
2,755,699 A 7/1956 Forster
2,910,067 A 10/1959 White
2,944,311 A 7/1960 Schneckenberger
2,951,482 A 9/1960 Sullivan
2,969,887 A 1/1961 Darmstadt et al.
3,014,483 A 12/1961 McCarthy
3,015,403 A 1/1962 Fuller
3,113,379 A 12/1963 Frank
3,120,230 A 2/1964 Skold
3,142,878 A 8/1964 Santora
3,209,754 A 10/1965 Brown
3,348,595 A 10/1967 Stevens, Jr.
3,357,070 A 12/1967 Sloan
3,482,428 A 12/1969 Kapitanov et al.
3,494,533 A 2/1970 Green et al.
3,510,923 A 5/1970 Blake
3,513,848 A 5/1970 Winston et al.
3,523,351 A 8/1970 Filia
3,525,340 A 8/1970 Gilbert
3,586,002 A 6/1971 Wood
3,604,425 A 9/1971 Le Roy
3,618,447 A 11/1971 Goins
3,664,345 A 5/1972 Dabbs et al.
3,677,243 A 7/1972 Nerz
3,682,180 A 8/1972 McFarlane
3,732,719 A 5/1973 Pallotta
3,750,650 A 8/1973 Ruttgers
3,753,438 A 8/1973 Wood et al.
3,757,629 A 9/1973 Schneider
3,805,337 A 4/1974 Branstetter
3,814,104 A 6/1974 Irnich et al.
3,823,719 A 7/1974 Cummings
3,828,791 A 8/1974 Santos
3,831,608 A 8/1974 Kletschka et al.
3,856,016 A 12/1974 Davis
3,874,388 A 4/1975 King et al.
3,908,662 A 9/1975 Razgulov et al.
3,926,194 A 12/1975 Greenberg et al.
3,931,821 A 1/1976 Kletschka et al.
3,939,820 A 2/1976 Grayzel
3,944,114 A 3/1976 Coppens
3,960,147 A 6/1976 Murray
3,976,079 A 8/1976 Samuels et al.
3,985,138 A 10/1976 Jarvik
4,007,743 A 2/1977 Blake
4,011,872 A 3/1977 Komiya
4,014,492 A 3/1977 Rothfuss
4,018,228 A 4/1977 Goosen
4,047,533 A 9/1977 Perciaccante et al.
4,064,881 A 12/1977 Meredith
4,112,944 A 9/1978 Williams
4,153,321 A 5/1979 Pombrol
4,162,673 A 7/1979 Patel
4,169,476 A 10/1979 Hiltebrandt
4,189,808 A 2/1980 Brown
4,192,315 A 3/1980 Hilzinger et al.
4,201,215 A 5/1980 Crossett et al.
4,204,541 A 5/1980 Kapitanov
4,207,870 A 6/1980 Eldridge
4,214,587 A 7/1980 Sakura, Jr.
4,215,699 A 8/1980 Patel
4,217,902 A 8/1980 March
4,267,995 A 5/1981 McMillan
4,273,129 A 6/1981 Boebel
4,274,415 A 6/1981 Kanamoto et al.
4,278,091 A 7/1981 Borzone
4,287,489 A 9/1981 Pinkham
4,291,698 A 9/1981 Fuchs et al.
4,317,445 A 3/1982 Robinson
4,317,451 A 3/1982 Cerwin et al.
4,318,401 A 3/1982 Zimmerman
4,327,485 A 5/1982 Rix
4,345,606 A 8/1982 Littleford
4,368,736 A 1/1983 Kaster
4,387,489 A 6/1983 Dudek
4,396,139 A 8/1983 Hall et al.
4,400,879 A 8/1983 Hildreth
4,407,286 A 10/1983 Noiles et al.
4,411,654 A 10/1983 Boarini et al.
4,412,832 A 11/1983 Kling et al.
4,428,376 A 1/1984 Mericle
4,440,170 A 4/1984 Golden et al.
4,449,531 A 5/1984 Cerwin et al.
4,475,544 A 10/1984 Reis
4,480,356 A 11/1984 Martin
4,485,816 A 12/1984 Krumme
4,501,276 A 2/1985 Lombardi
RE31,855 E 3/1985 Osborne
4,505,273 A 3/1985 Braun et al.
4,505,274 A 3/1985 Speelman
4,523,591 A 6/1985 Kaplan et al.
4,523,695 A 6/1985 Braun et al.
4,525,157 A 6/1985 Valaincourt
4,526,174 A 7/1985 Froehlich
4,577,635 A 3/1986 Meredith
4,586,503 A 5/1986 Kirsch et al.
4,592,498 A 6/1986 Braun et al.
4,596,559 A 6/1986 Fleischhacker
4,607,638 A 8/1986 Crainich
4,610,251 A 9/1986 Kumar
4,610,252 A 9/1986 Catalano
4,635,634 A 1/1987 Santos
4,644,956 A 2/1987 Morgenstern
4,651,737 A 3/1987 Deniega
4,664,305 A 5/1987 Blake, III et al.
4,665,906 A 5/1987 Jervis
4,667,675 A 5/1987 Davis
4,683,895 A 8/1987 Pohndorf
4,687,469 A 8/1987 Osypka
4,693,249 A 9/1987 Schenck et al.
4,697,312 A 10/1987 Freyer
4,719,917 A 1/1988 Barrows et al.
4,724,840 A 2/1988 McVay et al.
4,738,658 A 4/1988 Magro et al.
4,744,364 A 5/1988 Kensey
4,747,407 A 5/1988 Liu et al.
4,750,492 A 6/1988 Jacobs
4,759,364 A 7/1988 Boebel
4,771,782 A 9/1988 Millar
4,772,266 A 9/1988 Groshong
4,773,421 A 9/1988 Davis
4,777,950 A 10/1988 Kees, Jr.
4,789,090 A 12/1988 Blake, III
4,813,586 A 3/1989 Seifert
4,823,794 A 4/1989 Pierce
4,830,002 A 5/1989 Semm
4,832,688 A 5/1989 Sagae et al.
4,836,204 A 6/1989 Landymore et al.
4,852,568 A 8/1989 Kensey
4,860,746 A 8/1989 Yoon
4,865,026 A 9/1989 Barrett
4,866,818 A 9/1989 Thompson
4,874,122 A 10/1989 Froelich et al.
4,878,915 A 11/1989 Brantigan
4,885,003 A 12/1989 Hillstead

(56) References Cited

U.S. PATENT DOCUMENTS 4,886,067 A 12/1989 Palermo
4,887,601 A 12/1989 Richards
4,890,612 A 1/1990 Kensey
4,902,508 A 2/1990 Badylak et al.
4,917,087 A 4/1990 Walsh et al.
4,917,089 A 4/1990 Sideris
4,929,240 A 5/1990 Kirsch et al.
4,934,364 A 6/1990 Green
4,950,258 A 8/1990 Kawai et al.
4,957,499 A 9/1990 Lipatov et al.
4,961,729 A 10/1990 Vaillancourt
4,967,949 A 11/1990 Sandhaus
4,976,721 A 12/1990 Blasnik et al.
4,983,176 A 1/1991 Cushman et al.
4,997,436 A 3/1991 Oberlander
4,997,439 A 3/1991 Chen
5,002,562 A 3/1991 Oberlander
5,007,921 A 4/1991 Brown
5,009,663 A 4/1991 Broom
5,015,247 A 5/1991 Michelson
5,021,059 A 6/1991 Kensey et al.
5,026,390 A 6/1991 Brown
5,030,226 A 7/1991 Green et al.
5,032,127 A 7/1991 Frazee et al.
5,035,692 A 7/1991 Lyon et al.
5,047,047 A 9/1991 Yoon
5,053,008 A 10/1991 Bajaj
5,059,201 A 10/1991 Asnis
5,061,274 A 10/1991 Kensey
5,071,430 A 12/1991 de Salis et al.
5,078,731 A 1/1992 Hayhurst
5,092,941 A 3/1992 Miura
5,100,418 A 3/1992 Yoon et al.
5,100,422 A 3/1992 Berguer et al.
5,108,420 A 4/1992 Marks
5,108,421 A 4/1992 Fowler
5,114,032 A 5/1992 Laidlaw
5,114,065 A 5/1992 Storace
5,116,349 A 5/1992 Aranyi
5,122,122 A 6/1992 Allgood
5,122,156 A 6/1992 Granger et al.
5,131,379 A 7/1992 Sewell, Jr.
5,141,520 A 8/1992 Goble et al.
5,147,381 A 9/1992 Heimerl et al.
5,156,609 A 10/1992 Nakao et al.
5,158,566 A 10/1992 Pianetti
5,160,339 A 11/1992 Chen et al.
5,163,343 A 11/1992 Gish
5,167,634 A 12/1992 Corrigan, Jr. et al.
5,167,643 A 12/1992 Lynn
5,171,249 A 12/1992 Stefanchik et al.
5,171,250 A 12/1992 Yoon
5,171,251 A 12/1992 Bregen et al.
5,176,648 A 1/1993 Holmes et al.
5,176,682 A 1/1993 Chow
5,176,691 A 1/1993 Pierce
5,192,287 A 3/1993 Fournier et al.
5,192,288 A 3/1993 Thompson et al.
5,192,300 A 3/1993 Fowler
5,192,301 A 3/1993 Kamiya et al.
5,192,302 A 3/1993 Kensey et al.
5,192,602 A 3/1993 Spencer et al.
5,193,533 A 3/1993 Body et al.
5,197,971 A 3/1993 Bonutti
5,203,787 A 4/1993 Noblitt et al.
5,209,756 A 5/1993 Seedhorm et al.
5,217,024 A 6/1993 Dorsey et al.
5,217,471 A 6/1993 Burkhart
5,219,359 A 6/1993 McQuilkin et al.
5,222,974 A 6/1993 Kensey et al.
5,226,908 A 7/1993 Yoon
5,234,449 A 8/1993 Bruker et al.
5,236,435 A 8/1993 Sewell, Jr.
5,236,445 A 8/1993 Hayhurst et al.
5,237,996 A 8/1993 Waldman
5,242,456 A 9/1993 Nash et al.
5,242,457 A 9/1993 Akopov et al.
5,242,459 A 9/1993 Buelna
5,243,857 A 9/1993 Velez
5,246,156 A 9/1993 Rothfuss et al.
5,246,443 A 9/1993 Mai
5,250,058 A 10/1993 Miller et al.
5,254,105 A 10/1993 Haaga
5,255,679 A 10/1993 Imran
5,258,015 A 11/1993 Li et al.
5,269,792 A 12/1993 Kovac et al.
5,275,616 A 1/1994 Fowler
5,281,422 A 1/1994 Badylak et al.
5,282,808 A 2/1994 Kovac et al.
5,282,827 A 2/1994 Kensey et al.
5,282,832 A 2/1994 Toso et al.
5,289,963 A 3/1994 McGarry et al.
5,290,243 A 3/1994 Chodorow et al.
5,290,310 A 3/1994 Makower et al.
5,292,309 A 3/1994 Van Tassel et al.
5,292,332 A 3/1994 Lee
5,304,183 A 4/1994 Gourlay et al.
5,304,184 A 4/1994 Hathaway et al.
5,304,204 A 4/1994 Bregen
5,306,254 A 4/1994 Nash et al.
5,306,280 A 4/1994 Bregen et al.
5,309,927 A 5/1994 Welch
5,318,542 A 6/1994 Hirsch et al.
5,320,639 A 6/1994 Rudnick
5,327,908 A 7/1994 Gerry
5,330,442 A 7/1994 Green et al.
5,330,445 A 7/1994 Haaga
5,330,503 A 7/1994 Yoon
5,334,216 A 8/1994 Vidal et al.
5,334,217 A 8/1994 Das
5,335,680 A 8/1994 Moore
5,340,360 A 8/1994 Stefanchik
5,342,393 A 8/1994 Stack
5,344,439 A 9/1994 Otten
5,350,399 A 9/1994 Erlebacher et al.
5,352,229 A 10/1994 Goble et al.
5,354,279 A 10/1994 Hofling
5,364,406 A 11/1994 Sewell, Jr.
5,364,408 A 11/1994 Gordon
5,366,458 A 11/1994 Korthoff et al.
5,366,479 A 11/1994 McGarry et al.
5,376,101 A 12/1994 Green et al.
5,383,896 A 1/1995 Gershony et al.
5,383,897 A 1/1995 Wholey
5,383,905 A 1/1995 Golds et al.
RE34,866 E 2/1995 Kensey et al.
5,391,173 A 2/1995 Wilk
5,392,978 A 2/1995 Velez et al.
5,395,030 A 3/1995 Kuramoto et al.
5,403,330 A 4/1995 Tuason
5,403,331 A 4/1995 Chesterfield et al.
5,404,621 A 4/1995 Heinke
5,409,499 A 4/1995 Yi
5,411,520 A 5/1995 Nash et al.
5,413,571 A 5/1995 Katsaros et al.
5,413,584 A 5/1995 Schulze
5,416,584 A 5/1995 Kay
5,417,699 A 5/1995 Klein et al.
5,419,765 A 5/1995 Weldon et al.
5,419,777 A 5/1995 Hofling
5,421,832 A 6/1995 Lefebvre
5,423,857 A 6/1995 Rosenman et al.
5,425,489 A 6/1995 Shichman et al.
5,425,740 A 6/1995 Hutchinson, Jr.
5,431,639 A 7/1995 Shaw
5,431,667 A 7/1995 Thompson et al.
5,433,721 A 7/1995 Hooven et al.
5,437,631 A 8/1995 Janzen
5,439,479 A 8/1995 Shichman et al.
5,443,477 A 8/1995 Marin et al.
5,443,481 A 8/1995 Lee
5,445,167 A 8/1995 Yoon et al.
5,449,359 A 9/1995 Groiso
5,451,235 A 9/1995 Lock et al.

(56) References Cited

U.S. PATENT DOCUMENTS 5,456,400 A 10/1995 Shichman et al.
5,462,558 A 10/1995 Kolesa et al.
5,462,561 A 10/1995 Voda
5,464,413 A 11/1995 Siska, Jr. et al.
5,466,241 A 11/1995 Leroy et al.
5,470,010 A 11/1995 Rothfuss et al.
5,471,982 A 12/1995 Edwards et al.
5,474,557 A 12/1995 Mai
5,474,569 A 12/1995 Zinreich et al.
5,474,572 A 12/1995 Hayhurst
5,476,505 A 12/1995 Limon
5,478,352 A 12/1995 Fowler
5,478,353 A 12/1995 Yoon et al.
5,478,354 A 12/1995 Tovey et al.
5,486,195 A 1/1996 Myers et al.
5,492,119 A 2/1996 Abrams
5,496,332 A 3/1996 Sierra et al.
5,497,933 A 3/1996 DeFonzo et al.
5,501,698 A 3/1996 Roth et al.
5,507,744 A 4/1996 Tay et al.
5,507,755 A 4/1996 Gresl et al.
5,510,115 A 4/1996 Breillatt, Jr. et al.
5,514,159 A 5/1996 Matula et al.
5,521,184 A 5/1996 Zimmermann
5,522,840 A 6/1996 Krajicek
5,527,322 A 6/1996 Klein et al.
5,536,251 A 7/1996 Evard et al.
5,536,267 A 7/1996 Edwards
5,540,712 A 7/1996 Kleshinski et al.
5,540,716 A 7/1996 Hlavacek
5,543,520 A 8/1996 Zimmermann
5,544,802 A 8/1996 Crainich
5,547,474 A 8/1996 Kloeckl et al.
5,560,532 A 10/1996 DeFonzo et al.
5,562,684 A 10/1996 Kammerer
5,571,120 A 11/1996 Yoon
5,573,540 A 11/1996 Yoon
5,573,784 A 11/1996 Badylak et al.
5,575,771 A 11/1996 Walinsky
5,582,616 A 12/1996 Bolduc et al.
5,584,879 A 12/1996 Reimold et al.
5,591,205 A 1/1997 Fowler
5,593,412 A 1/1997 Martinez et al.
5,593,422 A 1/1997 Muijs Van de Moer et al.
5,593,425 A 1/1997 Bonutti et al.
5,601,602 A 2/1997 Fowler
5,609,597 A 3/1997 Lehrer
5,611,986 A 3/1997 Datta et al.
5,613,974 A 3/1997 Andreas et al.
5,613,975 A 3/1997 Christy
5,618,291 A 4/1997 Thompson et al.
5,618,306 A 4/1997 Roth et al.
5,620,452 A 4/1997 Yoon
5,620,461 A 4/1997 Muijs et al.
5,626,614 A 5/1997 Hart
5,630,824 A 5/1997 Hart
5,634,936 A 6/1997 Linden et al.
5,643,318 A 7/1997 Tsukernik et al.
5,645,553 A 7/1997 Kolesa et al.
5,645,565 A 7/1997 Rudd et al.
5,645,566 A 7/1997 Brenneman et al.
5,645,567 A 7/1997 Crainich
5,647,372 A 7/1997 Tovey et al.
5,649,959 A 7/1997 Hannam et al.
D383,539 S 9/1997 Croley
5,669,917 A 9/1997 Sauer et al.
5,669,935 A 9/1997 Rosenman et al.
5,672,174 A 9/1997 Gough et al.
5,674,231 A 10/1997 Green et al.
5,676,689 A 10/1997 Kensey et al.
5,676,974 A 10/1997 Valdes et al.
5,681,280 A 10/1997 Rusk et al.
5,681,334 A 10/1997 Evans et al.
5,681,351 A 10/1997 Jamiolkowski et al.
5,683,405 A 11/1997 Yacoubian et al.
5,690,674 A 11/1997 Diaz
5,693,061 A 12/1997 Pierce et al.
5,695,504 A 12/1997 Gifford, III et al.
5,695,505 A 12/1997 Yoon
5,695,524 A 12/1997 Kelley et al.
5,697,943 A 12/1997 Sauer et al.
5,700,273 A 12/1997 Buelna et al.
5,709,224 A 1/1998 Behl et al.
5,709,708 A 1/1998 Thal
5,713,899 A 2/1998 Marnay et al.
5,715,987 A 2/1998 Kelley et al.
5,716,375 A 2/1998 Fowler
5,720,755 A 2/1998 Dakov
5,720,765 A 2/1998 Thal
5,725,498 A 3/1998 Janzen et al.
5,725,552 A 3/1998 Kotula et al.
5,725,554 A 3/1998 Simon et al.
5,725,556 A 3/1998 Moser et al.
5,728,109 A 3/1998 Schulze et al.
5,728,110 A 3/1998 Vidal et al.
5,728,114 A 3/1998 Evans et al.
5,728,116 A 3/1998 Rosenman
5,728,122 A 3/1998 Leschinsky et al.
5,728,132 A 3/1998 Van Tassel et al.
5,728,133 A 3/1998 Kontos
5,728,143 A 3/1998 Gough et al.
5,732,872 A 3/1998 Bolduc et al.
5,735,736 A 4/1998 Volk
5,735,873 A 4/1998 MacLean
5,735,875 A 4/1998 Bonutti et al.
5,735,877 A 4/1998 Pagedas
5,749,826 A 5/1998 Faulkner
5,749,898 A 5/1998 Schulze et al.
5,752,966 A 5/1998 Chang
5,755,726 A 5/1998 Pratt et al.
5,755,778 A 5/1998 Kleshinski
5,759,189 A 6/1998 Ferragamo et al.
5,766,217 A 6/1998 Christy
5,766,246 A 6/1998 Mulhauser et al.
5,769,862 A 6/1998 Kammerer et al.
5,769,870 A 6/1998 Salahieh et al.
5,776,147 A 7/1998 Dolendo
5,776,150 A 7/1998 Nolan et al.
5,779,707 A 7/1998 Bertholet et al.
5,780,807 A 7/1998 Saunders
5,782,844 A 7/1998 Yoon et al.
5,782,860 A 7/1998 Epstein et al.
5,782,861 A 7/1998 Cragg et al.
5,782,864 A 7/1998 Lizardi
5,795,958 A 8/1998 Rao et al.
5,797,928 A 8/1998 Kogasaka
5,797,929 A 8/1998 Andreas et al.
5,797,931 A 8/1998 Bito et al.
5,797,933 A 8/1998 Snow et al.
5,797,958 A 8/1998 Yoon
5,797,960 A 8/1998 Stevens et al.
5,810,776 A 9/1998 Bacich et al.
5,810,846 A 9/1998 Virnich et al.
5,810,851 A 9/1998 Yoon
5,810,877 A 9/1998 Roth et al.
5,814,069 A 9/1998 Schulze et al.
5,817,113 A 10/1998 Gifford, III et al.
5,820,631 A 10/1998 Nobles
5,827,298 A 10/1998 Hart et al.
5,830,125 A 11/1998 Scribner et al.
5,830,221 A 11/1998 Stein et al.
5,833,698 A 11/1998 Hinchliffe et al.
5,843,164 A 12/1998 Frantzen et al.
5,843,167 A 12/1998 Dwyer et al.
5,845,657 A 12/1998 Carberry et al.
5,846,254 A 12/1998 Schulze et al.
5,853,421 A 12/1998 Leschinsky et al.
5,853,422 A 12/1998 Huebsch et al.
5,855,312 A 1/1999 Toledano
5,855,576 A 1/1999 LeVeen et al.
5,858,082 A 1/1999 Cruz et al.
5,860,991 A 1/1999 Klein et al.
5,861,003 A 1/1999 Latson et al.
5,861,005 A 1/1999 Kontos

(56) References Cited

U.S. PATENT DOCUMENTS 5,868,755 A 2/1999 Kanner et al.
5,868,762 A 2/1999 Cragg et al.
5,868,763 A 2/1999 Spence et al.
5,871,474 A 2/1999 Hermann et al.
5,871,490 A 2/1999 Schulze et al.
5,871,501 A 2/1999 Leschinsky et al.
5,871,525 A 2/1999 Edwards et al.
5,873,876 A 2/1999 Christy
5,873,891 A 2/1999 Sohn
5,879,366 A 3/1999 Shaw et al.
5,891,088 A 4/1999 Thompson et al.
5,893,592 A 4/1999 Schulze et al.
5,897,487 A 4/1999 Ouchi
5,902,310 A 5/1999 Foerster et al.
5,904,697 A 5/1999 Gifford, III et al.
5,906,631 A 5/1999 Imran
5,907,893 A 6/1999 Zadno-Azizi et al.
5,908,149 A 6/1999 Welch et al.
5,910,155 A 6/1999 Ratcliff et al.
5,919,207 A 7/1999 Taheri
5,919,208 A 7/1999 Valenti
5,922,009 A 7/1999 Epstein et al.
5,928,231 A 7/1999 Klein et al.
5,928,251 A 7/1999 Aranyi et al.
5,935,147 A 8/1999 Kensey et al.
5,938,667 A 8/1999 Peyser et al.
5,941,890 A 8/1999 Voegele et al.
5,947,999 A 9/1999 Groiso
5,948,001 A 9/1999 Larsen
5,951,518 A 9/1999 Licata et al.
5,951,547 A 9/1999 Gough et al.
5,951,575 A 9/1999 Bolduc et al.
5,951,576 A 9/1999 Wakabayashi
5,951,589 A 9/1999 Epstein et al.
5,954,732 A 9/1999 Hart et al.
5,957,900 A 9/1999 Ouchi
5,957,936 A 9/1999 Yoon et al.
5,957,938 A 9/1999 Zhu et al.
5,957,940 A 9/1999 Tanner et al.
5,964,782 A 10/1999 Lafontaine et al.
5,972,023 A 10/1999 Tanner et al.
5,976,159 A 11/1999 Bolduc et al.
5,976,161 A 11/1999 Kirsch et al.
5,976,174 A 11/1999 Ruiz
5,980,517 A 11/1999 Gough et al.
5,984,934 A 11/1999 Ashby et al.
5,984,948 A 11/1999 Hasson
5,984,949 A 11/1999 Levin
5,993,466 A 11/1999 Yoon
5,993,468 A 11/1999 Rygaard
5,993,476 A 11/1999 Groiso
6,001,110 A 12/1999 Adams
6,004,341 A 12/1999 Zhu et al.
6,007,563 A 12/1999 Nash et al.
6,009,877 A 1/2000 Edwards
6,010,517 A 1/2000 Baccaro
6,013,084 A 1/2000 Ken et al.
6,015,815 A 1/2000 Mollison
6,019,779 A 2/2000 Thorud et al.
6,022,372 A 2/2000 Kontos
6,024,747 A 2/2000 Kontos
6,024,750 A 2/2000 Mastri et al.
6,024,756 A 2/2000 Huebsch et al.
6,024,758 A 2/2000 Thal
6,030,364 A 2/2000 Durgin et al.
6,030,413 A 2/2000 Lazarus
6,033,427 A 3/2000 Lee
6,036,703 A 3/2000 Evans et al.
6,036,720 A 3/2000 Abrams et al.
6,045,570 A 4/2000 Epstein et al.
6,048,358 A 4/2000 Barak
6,056,744 A 5/2000 Edwards
6,056,768 A 5/2000 Cates et al.
6,056,769 A 5/2000 Epstein et al.
6,056,770 A 5/2000 Epstein et al.
6,059,800 A 5/2000 Hart et al.
6,059,825 A 5/2000 Hobbs et al.
6,063,085 A 5/2000 Tay et al.
6,063,114 A 5/2000 Nash et al.
6,066,160 A 5/2000 Colvin et al.
6,068,603 A 5/2000 Suzuki
6,071,300 A 6/2000 Brenneman et al.
6,074,395 A 6/2000 Trott et al.
6,074,409 A 6/2000 Goldfarb
6,077,281 A 6/2000 Das
6,077,291 A 6/2000 Das
6,080,182 A 6/2000 Shaw et al.
6,080,183 A 6/2000 Tsugita et al.
6,083,242 A 7/2000 Cook
6,086,608 A 7/2000 Ek et al.
6,090,130 A 7/2000 Nash et al.
6,092,561 A 7/2000 Schmid
6,095,155 A 8/2000 Criscuolo
6,099,553 A 8/2000 Hart et al.
6,102,271 A 8/2000 Longo et al.
6,106,545 A 8/2000 Egan
6,110,184 A 8/2000 Weadock
6,113,610 A 9/2000 Poncet
6,113,612 A 9/2000 Swanson et al.
6,117,125 A 9/2000 Rothbarth et al.
6,117,148 A 9/2000 Ravo
6,117,157 A 9/2000 Tekulve
6,117,159 A 9/2000 Huebsch et al.
6,120,513 A 9/2000 Bailey et al.
6,120,524 A 9/2000 Taheri
6,126,675 A 10/2000 Schervinsky et al.
6,126,677 A 10/2000 Ganaja et al.
6,136,010 A 10/2000 Modesitt et al.
6,143,004 A 11/2000 Davis et al.
6,143,017 A 11/2000 Thal
6,146,385 A 11/2000 Torrie et al.
6,149,660 A 11/2000 Laufer et al.
6,149,667 A 11/2000 Hovland et al.
6,152,144 A 11/2000 Lesh et al.
6,152,934 A 11/2000 Harper et al.
6,152,936 A 11/2000 Christy et al.
6,152,937 A 11/2000 Peterson et al.
6,159,234 A 12/2000 Bonutti et al.
6,161,263 A 12/2000 Anderson
6,165,204 A 12/2000 Levinson et al.
6,171,277 B1 1/2001 Ponzi
6,171,329 B1 1/2001 Shaw et al.
6,174,322 B1 1/2001 Schneidt
6,174,324 B1 1/2001 Egan et al.
6,179,849 B1 1/2001 Yencho et al.
6,179,860 B1 1/2001 Fulton, III et al.
6,193,708 B1 2/2001 Ken et al.
6,193,734 B1 2/2001 Bolduc et al.
6,197,042 B1 3/2001 Ginn et al.
6,198,974 B1 3/2001 Webster, Jr.
6,200,329 B1 3/2001 Fung et al.
6,200,330 B1 3/2001 Benderev et al.
6,203,565 B1 3/2001 Bonutti et al.
6,206,895 B1 3/2001 Levinson
6,206,913 B1 3/2001 Yencho et al.
6,206,931 B1 3/2001 Cook et al.
6,210,407 B1 4/2001 Webster
6,220,248 B1 4/2001 Voegele et al.
6,221,084 B1 4/2001 Fleenor
6,221,102 B1 4/2001 Baker et al.
6,231,561 B1 5/2001 Frazier et al.
6,231,592 B1 5/2001 Bonutti et al.
6,238,705 B1 5/2001 Liu et al.
6,241,740 B1 6/2001 Davis et al.
6,245,079 B1 6/2001 Nobles et al.
6,248,124 B1 6/2001 Pedros et al.
6,254,615 B1 7/2001 Bolduc et al.
6,254,617 B1 7/2001 Spence et al.
6,254,642 B1 7/2001 Taylor
6,258,115 B1 7/2001 Dubrul
6,267,773 B1 7/2001 Gadberry et al.
6,273,903 B1 8/2001 Wilk
6,276,704 B1 8/2001 Suiter
6,277,140 B2 8/2001 Ginn et al.

(56) References Cited

U.S. PATENT DOCUMENTS 6,280,460 B1 8/2001 Bolduc et al.
6,287,322 B1 9/2001 Zhu et al.
6,287,335 B1 9/2001 Drasler et al.
6,290,674 B1 9/2001 Roue et al.
6,296,657 B1 10/2001 Brucker
6,302,870 B1 10/2001 Jacobsen et al.
6,302,898 B1 10/2001 Edwards et al.
6,305,891 B1 10/2001 Burlingame
6,306,081 B1 10/2001 Ishikawa et al.
6,309,416 B1 10/2001 Swanson et al.
6,319,258 B1 11/2001 McAllen, III et al.
6,322,580 B1 11/2001 Kanner
6,328,727 B1 12/2001 Frazier et al.
6,329,386 B1 12/2001 Mollison
6,334,865 B1 1/2002 Redmond et al.
6,348,064 B1 * 2/2002 Kanner ......................... 606/219
6,355,052 B1 3/2002 Neuss et al.
6,358,258 B1 3/2002 Arcia et al.
6,375,671 B1 4/2002 Kobayashi et al.
D457,958 S 5/2002 Dycus
6,383,208 B1 5/2002 Sancoff et al.
6,391,048 B1 5/2002 Ginn et al.
6,395,015 B1 5/2002 Borst et al.
6,397,110 B1 5/2002 Kuzma
6,398,752 B1 6/2002 Sweezer et al.
6,402,765 B1 6/2002 Monassevitch et al.
6,409,739 B1 6/2002 Nobles et al.
6,419,669 B1 7/2002 Frazier et al.
6,421,899 B1 7/2002 Zitnay
6,423,054 B1 7/2002 Ouchi
6,425,911 B1 7/2002 Akerfeldt et al.
6,428,472 B1 8/2002 Haas
6,428,548 B1 8/2002 Durgin et al.
6,443,158 B1 9/2002 Lafontaine et al.
6,443,963 B1 9/2002 Baldwin et al.
6,447,540 B1 9/2002 Fontaine et al.
6,450,391 B1 9/2002 Kayan et al.
6,455,053 B1 9/2002 Okada et al.
6,458,130 B1 10/2002 Frazier et al.
6,461,364 B1 10/2002 Ginn et al.
6,461,366 B1 10/2002 Seguin
6,482,224 B1 11/2002 Michler et al.
6,488,692 B1 12/2002 Spence et al.
6,500,115 B2 12/2002 Krattiger et al.
6,506,210 B1 1/2003 Kanner
6,508,828 B1 1/2003 Akerfeldt et al.
6,514,280 B1 2/2003 Gilson
6,517,498 B1 2/2003 Burbank et al.
6,517,555 B1 2/2003 Caro
6,517,569 B2 2/2003 Mikus et al.
6,527,737 B2 3/2003 Kaneshige
6,533,762 B2 3/2003 Kanner et al.
6,533,812 B2 3/2003 Swanson et al.
6,537,288 B2 3/2003 Vargas et al.
6,547,806 B1 4/2003 Ding
6,551,319 B2 4/2003 Lieberman
6,558,349 B1 5/2003 Kirkman
6,569,159 B1 5/2003 Edwards et al.
6,569,173 B1 5/2003 Blatter et al.
6,569,185 B2 5/2003 Ungs
6,572,629 B2 6/2003 Kalloo et al.
6,578,585 B1 6/2003 Stachowski et al.
6,582,452 B2 6/2003 Coleman et al.
6,582,482 B2 6/2003 Gillman et al.
6,596,012 B2 7/2003 Akerfeldt et al.
6,599,303 B1 7/2003 Peterson et al.
6,599,311 B1 7/2003 Biggs et al.
6,602,263 B1 8/2003 Swanson et al.
6,610,072 B1 8/2003 Christy et al.
6,613,059 B2 9/2003 Schaller et al.
6,613,060 B2 9/2003 Adams et al.
6,616,686 B2 9/2003 Coleman et al.
6,620,165 B2 9/2003 Wellisz
6,623,509 B2 9/2003 Ginn
6,623,510 B2 9/2003 Carley et al.
6,626,918 B1 9/2003 Ginn et al.
6,626,919 B1 9/2003 Swanstrom
6,626,920 B2 9/2003 Whayne
6,632,197 B2 10/2003 Lyon
6,632,238 B2 10/2003 Ginn et al.
6,634,537 B2 10/2003 Chen
6,645,205 B2 11/2003 Ginn
6,645,225 B1 11/2003 Atkinson
6,652,538 B2 11/2003 Kayan et al.
6,652,556 B1 11/2003 VanTassel et al.
6,663,633 B1 12/2003 Pierson, III
6,663,655 B2 12/2003 Ginn et al.
6,669,714 B2 12/2003 Coleman et al.
6,673,083 B1 1/2004 Kayan et al.
6,676,665 B2 1/2004 Foley et al.
6,676,671 B2 1/2004 Robertson et al.
6,676,685 B2 1/2004 Pedros et al.
6,679,904 B2 1/2004 Gleeson et al.
6,685,707 B2 2/2004 Roman et al.
6,689,051 B2 2/2004 Nakada et al.
6,689,147 B1 2/2004 Koster, Jr.
6,695,867 B2 2/2004 Ginn et al.
6,699,256 B1 3/2004 Logan et al.
6,702,826 B2 3/2004 Liddicoat et al.
6,712,836 B1 3/2004 Berg et al.
6,712,837 B2 3/2004 Akerfeldt et al.
6,726,704 B1 4/2004 Loshakove et al.
6,736,822 B2 5/2004 McClellan et al.
6,743,195 B2 6/2004 Zucker
6,743,243 B1 6/2004 Roy et al.
6,743,259 B2 6/2004 Ginn
6,745,079 B2 6/2004 King
6,746,457 B2 6/2004 Dana et al.
6,746,472 B2 6/2004 Frazier et al.
6,749,621 B2 6/2004 Pantages et al.
6,749,622 B2 6/2004 McGuckin et al.
6,752,813 B2 6/2004 Goldfarb et al.
6,755,842 B2 6/2004 Kanner et al.
6,758,855 B2 7/2004 Fulton, III et al.
6,767,356 B2 7/2004 Kanner et al.
6,776,785 B1 8/2004 Yencho et al.
6,780,197 B2 8/2004 Roe et al.
6,786,915 B2 9/2004 Akerfeldt et al.
6,790,218 B2 9/2004 Jayaraman
6,790,220 B2 9/2004 Morris et al.
6,837,893 B2 1/2005 Miller
6,837,906 B2 1/2005 Ginn
6,846,319 B2 1/2005 Ginn et al.
6,849,078 B2 2/2005 Durgin et al.
6,860,895 B1 3/2005 Akerfeldt et al.
6,890,343 B2 5/2005 Ginn et al.
6,896,687 B2 5/2005 Dakov
6,896,692 B2 5/2005 Ginn et al.
6,904,647 B2 6/2005 Byers, Jr.
6,913,607 B2 7/2005 Ainsworth et al.
6,926,723 B1 8/2005 Mulhauser et al.
6,926,731 B2 8/2005 Coleman et al.
6,929,634 B2 8/2005 Dorros et al.
6,942,641 B2 9/2005 Seddon
6,942,674 B2 9/2005 Belef et al.
6,942,691 B1 9/2005 Chuter
6,964,668 B2 11/2005 Modesitt et al.
6,969,391 B1 11/2005 Gazzani
6,969,397 B2 11/2005 Ginn
6,984,238 B2 1/2006 Gifford, III et al.
6,989,003 B2 1/2006 Wing et al.
6,989,016 B2 1/2006 Tallarida et al.
7,001,398 B2 2/2006 Carley et al.
7,001,400 B1 2/2006 Modesitt et al.
7,008,435 B2 3/2006 Cummins
7,008,439 B1 3/2006 Janzen et al.
7,025,776 B1 4/2006 Houser et al.
7,033,379 B2 4/2006 Peterson
7,048,747 B2 5/2006 Arcia et al.
7,060,084 B1 6/2006 Loshakove et al.
7,063,661 B2 6/2006 Okada
7,063,711 B1 6/2006 Loshakove et al.
7,074,232 B2 7/2006 Kanner et al.
7,076,305 B2 7/2006 Imran et al.

(56) References Cited

U.S. PATENT DOCUMENTS 7,083,635 B2 8/2006 Ginn
7,087,064 B1 8/2006 Hyde
7,108,709 B2 9/2006 Cummins
7,108,710 B2 9/2006 Anderson
7,111,768 B2 9/2006 Cummins et al.
7,112,225 B2 9/2006 Ginn
7,122,002 B2 10/2006 Okada
7,144,411 B2 12/2006 Ginn et al.
7,147,646 B2 12/2006 Dana et al.
7,163,551 B2 1/2007 Anthony et al.
7,169,158 B2 1/2007 Sniffin et al.
7,169,164 B2 1/2007 Borillo et al.
7,211,101 B2 5/2007 Carley et
7,220,268 B2 5/2007 Blatter
7,261,716 B2 8/2007 Strobel et al.
7,270,672 B1 9/2007 Singer
7,306,614 B2 12/2007 Weller et al.
7,311,720 B2 12/2007 Mueller et al.
7,316,704 B2 1/2008 Bagaoisan et al.
7,316,706 B2 1/2008 Bloom et al.
7,322,995 B2 1/2008 Bechman et al.
7,326,230 B2 2/2008 Ravikumar
7,331,979 B2 2/2008 Khosravi et al.
7,335,220 B2 2/2008 Khosravi et al.
D566,272 S 4/2008 Walberg et al.
7,361,178 B2 4/2008 Hearn et al.
7,361,183 B2 4/2008 Ginn
7,361,185 B2 4/2008 O'Malley et al.
7,393,363 B2 7/2008 Ginn
7,396,359 B1 7/2008 Derowe et al.
7,431,727 B2 10/2008 Cole et al.
7,431,729 B2 10/2008 Chanduszko
7,445,596 B2 11/2008 Kucklick et al.
7,465,286 B2 12/2008 Patterson et al.
7,507,200 B2 3/2009 Okada
7,533,790 B1 5/2009 Knodel et al.
7,582,103 B2 9/2009 Young et al.
7,582,104 B2 9/2009 Corcoran et al.
7,597,706 B2 10/2009 Kanner et al.
7,618,427 B2 11/2009 Ortiz et al.
7,622,628 B2 11/2009 Bergin et al.
7,645,285 B2 1/2010 Cosgrove et al.
D611,144 S 3/2010 Reynolds
7,678,135 B2 3/2010 Maahs et al.
7,727,249 B2 6/2010 Rahmani
7,731,655 B2 6/2010 Smith et al.
7,749,249 B2 7/2010 Gelbart et al.
7,780,696 B2 8/2010 Daniel et al.
7,799,042 B2 9/2010 Williamson, IV et al.
7,819,895 B2 10/2010 Ginn et al.
7,931,671 B2 4/2011 Tenerz
7,967,842 B2 6/2011 Bakos
8,103,327 B2 1/2012 Harlev et al.
8,105,352 B2 1/2012 Egnelov
8,226,666 B2 7/2012 Zarbatany et al.
2001/0007077 A1 7/2001 Ginn et al.
2001/0031972 A1 10/2001 Robertson et al.
2001/0031973 A1 10/2001 Nobles et al.
2001/0044639 A1 11/2001 Levinson
2001/0046518 A1 11/2001 Sawhney
2001/0047180 A1 11/2001 Grudem et al.
2001/0053909 A1 12/2001 Nakada
2002/0022822 A1 2/2002 Cragg et al.
2002/0026215 A1 2/2002 Redmond et al.
2002/0026216 A1 2/2002 Grimes
2002/0029050 A1 3/2002 Gifford, III et al.
2002/0038127 A1 3/2002 Blatter et al.
2002/0042622 A1 4/2002 Vargas et al.
2002/0049427 A1 4/2002 Wiener et al.
2002/0049472 A1 4/2002 Coleman et al.
2002/0058960 A1 5/2002 Hudson et al.
2002/0062104 A1 5/2002 Ashby et al.
2002/0072768 A1 6/2002 Ginn
2002/0077657 A1 6/2002 Ginn et al.
2002/0082641 A1 6/2002 Ginn et al.
2002/0095181 A1 7/2002 Beyar
2002/0099389 A1 7/2002 Michler et al.
2002/0106409 A1 8/2002 Sawhney et al.
2002/0107542 A1 8/2002 Kanner et al.
2002/0133193 A1 9/2002 Ginn et al.
2002/0151921 A1 10/2002 Kanner et al.
2002/0151963 A1 10/2002 Brown et al.
2002/0183786 A1 12/2002 Girton
2002/0183787 A1 12/2002 Wahr et al.
2002/0188275 A1 12/2002 McGuckin et al.
2002/0188318 A1* 12/2002 Carley et al. .................. 606/213
2002/0193808 A1* 12/2002 Belef et al. .................... 606/139
2002/0198562 A1 12/2002 Ackerfeldt et al.
2002/0198589 A1 12/2002 Leong
2003/0004543 A1 1/2003 Gleeson et al.
2003/0009180 A1 1/2003 Hinchliffe et al.
2003/0009196 A1 1/2003 Peterson
2003/0018358 A1 1/2003 Saadat
2003/0023248 A1 1/2003 Parodi
2003/0032981 A1* 2/2003 Kanner et al. ................ 606/219
2003/0033006 A1 2/2003 Phillips et al.
2003/0045893 A1 3/2003 Ginn
2003/0055455 A1 3/2003 Yang et al.
2003/0060846 A1 3/2003 Egnelov et al.
2003/0065358 A1 4/2003 Frecker et al.
2003/0078598 A1 4/2003 Ginn et al.
2003/0083679 A1 5/2003 Grudem et al.
2003/0093096 A1 5/2003 McGuckin et al.
2003/0093108 A1 5/2003 Avellanet et al.
2003/0097140 A1 5/2003 Kanner
2003/0109890 A1 6/2003 Kanner et al.
2003/0125766 A1 7/2003 Ding
2003/0139819 A1 7/2003 Beer et al.
2003/0144695 A1 7/2003 McGuckin, Jr. et al.
2003/0158577 A1* 8/2003 Ginn et al. .................... 606/213
2003/0158578 A1 8/2003 Pantages et al.
2003/0195504 A1 10/2003 Tallarida et al.
2003/0195561 A1 10/2003 Carley et al.
2003/0208211 A1 11/2003 Kortenbach
2003/0233095 A1 12/2003 Urbanski et al.
2004/0009205 A1 1/2004 Sawhney
2004/0009289 A1 1/2004 Carley et al.
2004/0010285 A1 1/2004 Carley et al.
2004/0039414 A1 2/2004 Carley et al.
2004/0044350 A1 3/2004 Martin et al.
2004/0049224 A1 3/2004 Buehlmann et al.
2004/0059376 A1 3/2004 Breuniger
2004/0068273 A1 4/2004 Fariss et al.
2004/0073236 A1 4/2004 Carley et al.
2004/0073255 A1 4/2004 Ginn et al.
2004/0078053 A1 4/2004 Berg et al.
2004/0082906 A1 4/2004 Tallarida et al.
2004/0087985 A1 5/2004 Loshakove et al.
2004/0092962 A1 5/2004 Thornton et al.
2004/0092964 A1 5/2004 Modesitt et al.
2004/0092968 A1 5/2004 Caro et al.
2004/0092973 A1 5/2004 Chandusko et al.
2004/0093024 A1 5/2004 Lousararian et al.
2004/0093027 A1 5/2004 Fabisiak et al.
2004/0097978 A1 5/2004 Modesitt et al.
2004/0106980 A1 6/2004 Solovay et al.
2004/0127940 A1 7/2004 Ginn et al.
2004/0143290 A1 7/2004 Brightbill
2004/0143291 A1 7/2004 Corcoran et al.
2004/0153122 A1* 8/2004 Palermo ........................ 606/213
2004/0153123 A1 8/2004 Palermo et al.
2004/0158127 A1 8/2004 Okada
2004/0158287 A1 8/2004 Cragg et al.
2004/0158309 A1 8/2004 Wachter et al.
2004/0167511 A1 8/2004 Buehlmann et al.
2004/0167570 A1 8/2004 Pantages et al.
2004/0191277 A1 9/2004 Sawhney et al.
2004/0215232 A1 10/2004 Belhe et al.
2004/0243216 A1 12/2004 Gregorich
2004/0249412 A1 12/2004 Snow et al.
2004/0254591 A1 12/2004 Kanner et al.
2004/0267193 A1 12/2004 Bagaoisan et al.
2004/0267308 A1 12/2004 Bagaoisan et al.
2004/0267312 A1 12/2004 Kanner et al.

(56) References Cited

U.S. PATENT DOCUMENTS

2005/0038460 A1 2/2005 Jayaraman
2005/0038500 A1 2/2005 Boylan et al.
2005/0059982 A1 3/2005 Zung et al.
2005/0075654 A1 4/2005 Kelleher
2005/0075665 A1 4/2005 Brenzel et al.
2005/0085851 A1 4/2005 Fiehler et al.
2005/0085854 A1 4/2005 Ginn
2005/0085855 A1 4/2005 Forsberg
2005/0090859 A1 4/2005 Ravlkumar
2005/0119695 A1 6/2005 Carley et al.
2005/0121042 A1 6/2005 Belhe et al.
2005/0148818 A1 7/2005 Mesallum
2005/0149117 A1 7/2005 Khosravi et al.
2005/0152949 A1 7/2005 Hotchkiss et al.
2005/0154401 A1 7/2005 Weldon et al.
2005/0165357 A1 7/2005 McGuckin et al.
2005/0169974 A1 8/2005 Tenerz et al.
2005/0177189 A1 8/2005 Ginn et al.
2005/0187564 A1 8/2005 Jayaraman
2005/0203552 A1 9/2005 Laufer et al.
2005/0216057 A1 9/2005 Coleman et al.
2005/0222614 A1 10/2005 Ginn et al.
2005/0228443 A1 10/2005 Yassinzadeh
2005/0234508 A1 10/2005 Cummins et al.
2005/0245876 A1 11/2005 Khosravi et al.
2005/0256532 A1 11/2005 Nayak et al.
2005/0267528 A1 12/2005 Ginn et al.
2005/0267530 A1 12/2005 Cummins et al.
2005/0273136 A1 12/2005 Belef et al.
2005/0273137 A1 12/2005 Ginn
2005/0274768 A1 12/2005 Cummins et al.
2005/0283188 A1 12/2005 Loshakove et al.
2006/0020270 A1 1/2006 Jabba et al.
2006/0030867 A1 2/2006 Zadno
2006/0034930 A1 2/2006 Khosravi et al.
2006/0047313 A1 3/2006 Khanna et al.
2006/0058844 A1 3/2006 White et al.
2006/0064115 A1 3/2006 Allen et al.
2006/0089635 A1 4/2006 Young et al.
2006/0095029 A1 5/2006 Young et al.
2006/0100664 A1 5/2006 Pai et al.
2006/0135989 A1 6/2006 Carley et al.
2006/0142784 A1 6/2006 Kontos
2006/0144479 A1 7/2006 Carley et al.
2006/0167484 A1 7/2006 Carley et al.
2006/0190014 A1 8/2006 Ginn et al.
2006/0190036 A1 8/2006 Wendel et al.
2006/0190037 A1 8/2006 Ginn et al.
2006/0190038 A1 8/2006 Carley et al.
2006/0195123 A1 8/2006 Ginn et al.
2006/0195124 A1 8/2006 Ginn et al.
2006/0206146 A1 9/2006 Tenerz
2006/0253037 A1 11/2006 Ginn et al.
2006/0253072 A1 11/2006 Pai et al.
2006/0259049 A1 11/2006 Harada et al.
2006/0265012 A1 11/2006 Anderson
2006/0287674 A1 12/2006 Ginn et al.
2006/0293698 A1 12/2006 Douk
2007/0005093 A1 1/2007 Cox
2007/0010851 A1 1/2007 Chanduszko et al.
2007/0010853 A1 1/2007 Ginn et al.
2007/0010854 A1 1/2007 Cummins et al.
2007/0027476 A1 2/2007 Harris et al.
2007/0027525 A1 2/2007 Ben-Muvhar
2007/0049967 A1 3/2007 Sibbitt et al.
2007/0049968 A1 3/2007 Sibbitt, Jr. et al.
2007/0049970 A1 3/2007 Belef et al.
2007/0060895 A1 3/2007 Sibbitt et al.
2007/0060950 A1 3/2007 Khosravi et al.
2007/0060951 A1 3/2007 Shannon
2007/0073337 A1 3/2007 Abbott et al.
2007/0083230 A1 4/2007 Javois
2007/0083231 A1 4/2007 Lee
2007/0093869 A1 * 4/2007 Bloom et al. ................. 606/219
2007/0112304 A1 5/2007 Voss
2007/0112365 A1 5/2007 Hilal et al.
2007/0112385 A1 5/2007 Conlon
2007/0123816 A1 5/2007 Zhu et al.
2007/0123817 A1 5/2007 Khosravi et al.
2007/0123936 A1 5/2007 Goldin et al.
2007/0149996 A1 6/2007 Coughlin
2007/0172430 A1 7/2007 Brito et al.
2007/0179527 A1 8/2007 Eskuri et al.
2007/0185530 A1 8/2007 Chin-Chen et al.
2007/0203506 A1 8/2007 Sibbitt, Jr. et al.
2007/0203507 A1 8/2007 McLaughlin et al.
2007/0213747 A1 9/2007 Monassevitch et al.
2007/0225755 A1 9/2007 Preinitz et al.
2007/0225756 A1 9/2007 Preinitz et al.
2007/0225757 A1 9/2007 Preinitz et al.
2007/0225758 A1 9/2007 Preinitz et al.
2007/0239209 A1 10/2007 Fallman
2007/0250080 A1 10/2007 Jones et al.
2007/0265658 A1 11/2007 Nelson et al.
2007/0270904 A1 11/2007 Ginn
2007/0275036 A1 11/2007 Green III et al.
2007/0276416 A1 11/2007 Ginn et al.
2007/0276488 A1 11/2007 Wachter et al.
2007/0282352 A1 12/2007 Carley et al.
2007/0282373 A1 12/2007 Ashby et al.
2008/0004636 A1 1/2008 Walberg
2008/0004640 A1 1/2008 Ellingwood
2008/0009794 A1 1/2008 Bagaoisan et al.
2008/0033459 A1 2/2008 Shafi et al.
2008/0045979 A1 2/2008 Ma
2008/0058839 A1 3/2008 Nobles et al.
2008/0065151 A1 3/2008 Ginn
2008/0065152 A1 3/2008 Carley
2008/0086075 A1 4/2008 Isik et al.
2008/0091235 A1 4/2008 Sirota
2008/0093414 A1 4/2008 Bender et al.
2008/0114378 A1 5/2008 Matsushita
2008/0114395 A1 5/2008 Mathisen et al.
2008/0177288 A1 7/2008 Carlson
2008/0210737 A1 9/2008 Ginn et al.
2008/0221616 A1 9/2008 Ginn et al.
2008/0243148 A1 10/2008 Mikkaichi et al.
2008/0243182 A1 10/2008 Bates et al.
2008/0269801 A1 10/2008 Coleman et al.
2008/0269802 A1 10/2008 Coleman et al.
2008/0272173 A1 11/2008 Coleman et al.
2008/0287967 A1 11/2008 Andreas et al.
2008/0287988 A1 11/2008 Smith et al.
2008/0294001 A1 11/2008 Surti
2008/0300628 A1 12/2008 Ellingwood
2008/0312666 A1 12/2008 Ellingwood et al.
2008/0312686 A1 12/2008 Ellingwood
2008/0312740 A1 12/2008 Wachter et al.
2008/0319475 A1 12/2008 Clark
2009/0054912 A1 2/2009 Heanue et al.
2009/0105728 A1 4/2009 Noda et al.
2009/0112306 A1 4/2009 Bonsignore et al.
2009/0137900 A1 5/2009 Bonner et al.
2009/0157101 A1 6/2009 Reyes et al.
2009/0157102 A1 6/2009 Reynolds et al.
2009/0157103 A1 6/2009 Walberg et al.
2009/0171388 A1 7/2009 Dave et al.
2009/0177212 A1 7/2009 Carley et al.
2009/0177213 A1 7/2009 Carley et al.
2009/0187215 A1 7/2009 Mackiewicz et al.
2009/0216267 A1 8/2009 Willard et al.
2009/0221960 A1 9/2009 Albrecht et al.
2009/0227938 A1 9/2009 Fasching et al.
2009/0254119 A1 10/2009 Sibbitt, Jr. et al.
2009/0287244 A1 11/2009 Kokish
2009/0312789 A1 12/2009 Kassab et al.
2010/0042144 A1 2/2010 Bennett
2010/0114156 A1 5/2010 Mehl
2010/0114159 A1 5/2010 Roorda et al.
2010/0130965 A1 5/2010 Sibbitt, Jr. et al.
2010/0179567 A1 7/2010 Voss et al.
2010/0179571 A1 7/2010 Voss
2010/0179572 A1 7/2010 Voss et al.
2010/0179589 A1 7/2010 Roorda et al.

(56) References Cited

U.S. PATENT DOCUMENTS

2010/0179590 A1 7/2010 Fortson et al.
2010/0185234 A1 7/2010 Fortson et al.
2010/0249828 A1 9/2010 Mavani et al.
2011/0066163 A1 3/2011 Cho et al.
2011/0178548 A1 7/2011 Tenerz
2011/0270282 A1 11/2011 Lemke
2012/0035630 A1 2/2012 Roorda
2012/0101520 A1 4/2012 Ginn et al.
2012/0245603 A1 9/2012 Voss
2012/0245623 A1 9/2012 Kariniemi et al.
2012/0245626 A1 9/2012 Ellingwood et al.
2012/0310261 A1 12/2012 Cummins et al.
2013/0006274 A1 1/2013 Walberg et al.
2013/0338708 A1 12/2013 Cummins et al.
2014/0005692 A1 1/2014 Ellingwood et al.
2014/0018850 A1 1/2014 Ellingwood
2014/0142624 A1 5/2014 Pantages et al.

FOREIGN PATENT DOCUMENTS

DE 197 11 288 10/1998
DE 29723736 U1 4/1999
DE 19859952 2/2000
DE 102006056283 6/2008
EP 0 386 361 9/1990
EP 0 534 696 3/1993
EP 0 621 032 10/1994
EP 0 756 851 2/1997
EP 0 774 237 5/1997
EP 0 858 776 8/1998
EP 0 941 697 9/1999
EP 1 867 287 12/2007
FR 2 443 238 7/1980
FR 2 715 290 7/1995
FR 2 722 975 2/1996
FR 2 768 324 3/1999
GB 1 358 466 7/1974
GB 2 075 144 11/1981
GB 2 397 240 7/2004
IE S2000/0722 10/2001
IE S2000/0724 10/2001
IE S2001/0547 7/2002
IE S2001/0815 7/2002
IE S2001/0748 8/2002
IE S2001/0749 8/2002
IE S2002/0452 12/2002
IE S2002/0664 2/2003
IE S2002/0665 2/2003
IE S2002/0451 7/2003
IE S2002/0552 7/2003
IE S2003/0424 12/2003
IE S2003/0490 1/2004
IE S2004/0368 11/2005
IE S2005/0342 11/2005
JP 58-181006 12/1983
JP 12 74750 11/1989
JP 11500642 8/1997
JP 2000102546 4/2000
NL 9302140 7/1995
PL 171425 4/1997
RU 2086192 8/1997
SU 197801 6/1967
SU 495067 12/1975
SU 912155 3/1982
SU 1243708 7/1986
SU 1324650 7/1987
SU 1405828 6/1988
SU 1456109 2/1989
SU 1560133 4/1990
WO WO 95/21573 8/1995
WO WO 96/24291 8/1996
WO WO 97/07741 3/1997
WO WO 97/20505 6/1997
WO WO 97/27897 8/1997
WO WO 97/28745 8/1997
WO WO 98/06346 2/1998
WO WO 98/06448 2/1998
WO WO 98/16161 4/1998
WO WO 98/17179 4/1998
WO WO 98/18389 5/1998
WO WO 98/24374 6/1998
WO WO 98/25508 6/1998
WO WO 98/58591 12/1998
WO WO 99/21491 5/1999
WO WO 99/40849 8/1999
WO WO 99/60941 12/1999
WO WO 99/62408 12/1999
WO WO 99/62415 12/1999
WO WO 00/06029 2/2000
WO WO 00/07505 2/2000
WO WO 00/07640 2/2000
WO WO 00/27311 5/2000
WO WO 00/27313 5/2000
WO WO 00/56223 9/2000
WO WO 00/56227 9/2000
WO WO 00/56228 9/2000
WO WO 00/71032 11/2000
WO WO 01/21058 3/2001
WO WO 01/35832 5/2001
WO WO 01/47594 7/2001
WO WO 01/49186 7/2001
WO WO 01/91628 12/2001
WO WO 02/19915 3/2002
WO WO 02/19920 3/2002
WO WO 02/19922 3/2002
WO WO 02/19924 3/2002
WO WO 02/28286 4/2002
WO WO 02/38055 5/2002
WO WO 02/45593 6/2002
WO WO 02/45594 6/2002
WO WO 02/062234 8/2002
WO WO 02/098302 12/2002
WO WO 03/013363 2/2003
WO WO 03/013364 2/2003
WO WO03/071956 4/2003
WO WO 03/047434 6/2003
WO WO 03/071955 9/2003
WO WO 03/071956 9/2003
WO WO 03/071957 9/2003
WO WO 03/094748 11/2003
WO WO03/101310 11/2003
WO WO 03/101310 12/2003
WO WO 03101310 A1 * 12/2003
WO WO 2004/004578 1/2004
WO WO 2004/012602 2/2004
WO WO 2004/060169 7/2004
WO WO 2004/069054 8/2004
WO WO 2005/000126 1/2005
WO WO 2005/006990 1/2005
WO WO 2005/041782 5/2005
WO WO 2005/063129 7/2005
WO WO 2005/082256 9/2005
WO WO 2005/092204 10/2005
WO WO 2005/110240 11/2005
WO WO 2005/112782 12/2005
WO WO 2005/115251 12/2005
WO WO 2005/115521 12/2005
WO WO 2006/000514 1/2006
WO WO 0206/026116 3/2006
WO WO 2006/052611 5/2006
WO WO 2006/052612 5/2006
WO WO 2006/078578 7/2006
WO WO 2006/083889 8/2006
WO WO 2006/115901 11/2006
WO WO 2006/115904 11/2006
WO WO 2006/118877 11/2006
WO WO 2007/005585 1/2007
WO WO 2007/025014 3/2007
WO WO 2007/025017 3/2007
WO WO 2007/025019 3/2007
WO WO 20070/25018 3/2007
WO WO 2007/081836 7/2007
WO WO 2007/088069 8/2007

(56) References Cited

FOREIGN PATENT DOCUMENTS

| | | |
|---|---|---|
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/031050 | 3/2010 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

PCT patent application No. PCT/US2006/024334, Written Opinion mailed Jan. 16, 2007.
Marshall A.C., Lock J.E., *Structural and Compliant Anatomy of the Patent Foramen Ovale in Patients Undergoing Transcatheter Closure*, Am Heart J Aug. 2000; 140(2); pp. 303-307.
Taber's Cyclopedic Medical Dictionary, 18th Ed. 1997, pp. 747 and 1420.
U.S. Appl. No. 12/481,377, filed Jan. 3, 2012, Office Action.
U.S. Appl. No. 12/548,274, filed Dec. 28, 2011, Office Action.
U.S. Appl. No. 12/684,562, filed Dec. 28, 2011, Office Action.
U.S. Appl. No. 11/113,549, filed Jan. 4, 2011, Office Action.
U.S. Appl. No. 11/344,891, filed Jan. 22, 2013, Notice of Allowance.
U.S. Appl. No. 13/030,922, filed Jan. 31, 2013, Office Action.
U.S. Appl. No. 13/153,594, filed Jan. 29, 2013, Office Action.
U.S. Appl. No. 11/958,281, filed Mar. 10, 2011, Office Action.
U.S. Appl. No. 12/113,851, filed Apr. 27, 2011, Office Action.
U.S. Appl. No. 12/122,603, filed Apr. 22, 2011, Office Action.
U.S. Appl. No. 12/481,377, filed Apr. 28, 2011, Office Action.
U.S. Appl. No. 11/396,141, filed Apr. 30, 2013, Office Action.
U.S. Appl. No. 11/852,190, filed Apr. 24, 2013, Office Action.
U.S. Appl. No. 12/848,642, filed Apr. 26, 2013, Office Action.
U.S. Appl. No. 13/490,143, filed Apr. 29, 2013, Notice of Allowance.
U.S. Appl. No. 12/114,031, filed May 11, 2011, Office Action.
U.S. Appl. No. 12/143,020, filed May 11, 2011, Office Action.
U.S. Appl. No. 11/390,586, filed May 3, 2012, Notice of Allowance.
U.S. Appl. No. 12/684,400, filed May 9, 2012, Office Action.
U.S. Appl. No. 12/897,358, filed May 2, 2012, Issue Notification.
U.S. Appl. No. 12/966,923, filed May 16, 2012, Issue Notification.
U.S. Appl. No. 13/898,202, filed May 20, 2013, Walberg et al.
U.S. Appl. No. 11/344,891, filed May 15, 2013, Issue Notification.
U.S. Appl. No. 12/955,859, filed May 16, 2013, Office Action.
U.S. Appl. No. 13/488,233, filed May 15, 2013, Issue Notification.
U.S. Appl. No. 12/143,020, filed May 30, 2012, Issue Notification.
U.S. Appl. No. 12/393,877, filed May 21, 2012, Office Action.
U.S. Appl. No. 12/941,809, filed Jun. 1, 2012, Office Action.
U.S. Appl. No. 12/945,646, filed May 30, 2012, Issue Notification.
U.S. Appl. No. 12/973,204, filed May 30, 2012, Issue Notification.
U.S. Appl. No. 13/153,594, filed May 29, 2013, Office Action.
U.S. Appl. No. 13/791,829, filed May 29, 2013, Office Action.
U.S. Appl. No. 13/153,594, filed Jun. 6, 2011, Reyes et al.
U.S. Appl. No. 10/667,144, filed Jun. 6, 2011, Office Action.
U.S. Appl. No. 11/427,309, filed Jun. 7, 2013, Notice of Allowance.
U.S. Appl. No. 13/112,618, filed Jun. 7, 2013, Office Action.
U.S. Appl. No. 13/488,233, filed Jun. 5, 2013, Issue Notification.
U.S. Appl. No. 12/608,773, filed Jun. 7, 2012, Office Action.
U.S. Appl. No. 13/026,989, filed Jun. 8, 2012, Office Action.
U.S. Appl. No. 12/338,977, filed Jun. 19, 2013, Office Action.
U.S. Appl. No. 11/344,891, filed Jun. 26, 2013, Issue Notification.
U.S. Appl. No. 12/402,398, filed Jun. 26, 2013, Issue Notification.
U.S. Appl. No. 13/112,631, filed Jun. 26, 2013, Office Action.
U.S. Appl. No. 12/481,377, filed Jun. 21, 2011, Office Action.
U.S. Appl. No. 12/106,928, filed Jun. 28, 2013, Office Action.
U.S. Appl. No. 12/106,937, filed Jun. 28, 2013, Office Action.
U.S. Appl. No. 12/941,809, filed Jul. 3, 2013, Office Action.
U.S. Appl. No. 12/961,331, filed Jul. 3, 2013, Office Action.
U.S. Appl. No. 13/525,839, filed Jun. 18, 2012, Carley et al.
U.S. Appl. No. 11/427,297, filed Jun. 26, 2012, Notice of Allowance.
U.S. Appl. No. 11/767,818, filed Jul. 4, 2012, Issue Notification.
U.S. Appl. No. 12/338,977, filed Jul. 11, 2012, Office Action.
U.S. Appl. No. 12/135,858, filed Jul. 13, 2011, Office Action.
U.S. Appl. No. 10/786,444, filed Jul. 11, 2013, Notice of Allowance.
U.S. Appl. No. 11/532,325, filed Jul. 17, 2013, Office Action.
U.S. Appl. No. 13/030,922, filed Jul. 18, 2013, Office Action.
U.S. Appl. No. 13/525,839, filed Jul. 15, 2013, Notice of Allowance.
U.S. Appl. No. 13/615,547, filed Jul. 10, 2013, Issue Notification.
U.S. Appl. No. 10/435,104, filed Jul. 23, 2009, Notice of Allowance.
U.S. Appl. No. 10/669,313, filed Oct. 31, 2005, Office Action.
U.S. Appl. No. 11/113,549, filed Jul. 6, 2010, Offfice Action.
U.S. Appl. No. 11/959,334, filed Jul. 23, 2010, Notice of Allowance.
U.S. Appl. No. 12/403,277, filed Jul. 8, 2010, Office Action.
U.S. Appl. No. 10/908,721, filed Jul. 18, 2013, Notice of Allowance.
U.S. Appl. No. 11/744,089, filed Aug. 8, 2013, Notice of Allowance.
U.S. Appl. No. 12/850,242, filed Aug. 6, 2013, Notice of Allowance.
U.S. Appl. No. 12/955,859, filed Aug. 1, 2013, Notice of Allowance.
U.S. Appl. No. 13/615,547, filed Aug. 7, 2013, Issue Notification.
U.S. Appl. No. 11/675,462, filed Aug. 3, 2011, Office Action.
U.S. Appl. No. 12/114,031, filed Aug. 2, 2011, Office Action.
U.S. Appl. No. 10/682,459, filed Aug. 10, 2011, Issue Notification.
U.S. Appl. No. 11/675,462, filed Aug. 16, 2012, Issue Notification.
U.S. Appl. No. 11/744,089, filed Aug. 8, 2012, Office Action.
U.S. Appl. No. 12/481,377, filed Aug. 10, 2012, Notice of Allowance.
U.S. Appl. No. 12/850,242, filed Aug. 6, 2012, Office Action.
U.S. Appl. No. 12/955,859, filed Aug. 6, 2012, Office Action.
U.S. Appl. No. 11/396,141, filed Aug. 21, 2013, Office Action.
U.S. Appl. No. 13/026,989, filed Aug. 23, 2013, Office Action.
U.S. Appl. No. 13/490,143, filed Aug. 21, 2013, Issue Notification.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 09/610,128, filed Jul. 5, 2000, Kerievsky.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 10/006,400, filed Aug. 2, 2010, Notice of Allowance.
U.S. Appl. No. 10/517,004, filed Aug. 3, 2010, Notice of Allowance.
U.S. Appl. No. 10/541,083, filed Aug. 17, 2010, Notice of Allowance.
U.S. Appl. No. 10/682,459, filed Apr. 28, 2010, Office Action.
U.S. Appl. No. 11/048,503, filed Jul. 30, 2010, Notice of Allowance.
U.S. Appl. No. 11/427,309, filed May 28, 2008, Office Action.
U.S. Appl. No. 11/427,309, filed Jan. 2, 2009, Office Action.
U.S. Appl. No. 11/427,309, filed Apr. 20, 2009, Office Action.
U.S. Appl. No. 11/427,309, filed Nov. 6, 2009, Office Action.
U.S. Appl. No. 11/427,309, filed Apr. 26, 2009, Office Action.
U.S. Appl. No. 11/757,108, filed Nov. 25, 2009, Office Action.
U.S. Appl. No. 12/548,274, filed Sep. 10, 2012, Office Action.
U.S. Appl. No. 12/684,470, filed Aug. 30, 2012, Office Action.
U.S. Appl. No. 12/684,542, filed Sep. 13, 2012, Office Action.
U.S. Appl. No. 12/987,792, filed Sep. 17, 2012, Office Action.
U.S. Appl. No. 12/122,603, filed Sep. 23, 2011, Office Action.
U.S. Appl. No. 09/866,551, filed May 25, 2001, Ginn.
U.S. Appl. No. 10/616,832, filed Sep. 20, 2010, Notice of Allowance.
U.S. Appl. No. 10/638,115, filed Aug. 13, 2010, Notice of Allowance.
U.S. Appl. No. 10/787,073, filed Aug. 25, 2010, Notice of Allowance.
U.S. Appl. No. 11/152,562, filed Sep. 16, 2010, Notice of Allowance.
U.S. Appl. No. 11/508,656, filed Aug. 30, 2010, Office Action.
U.S. Appl. No. 11/675,462, filed Aug. 31, 2010, Office Action.
U.S. Appl. No. 11/958,281, filed Sep. 2, 2010, Office Action.
U.S. Appl. No. 12/403,256, filed Aug. 19, 2010, Notice of Allowance.
U.S. Appl. No. 12/393,877, filed Sep. 29, 2011, Office Action.
U.S. Appl. No. 10/435,104, filed Oct. 5, 2010, Notice of Allowance.
U.S. Appl. No. 10/787,073, filed Sep. 15, 2010, Issue Notification.
U.S. Appl. No. 11/427,297, filed Sep. 15, 2010, Office Action.
U.S. Appl. No. 11/767,818, filed Sep. 30, 2010, Office Action.
U.S. Appl. No. 12/365,397, filed Sep. 13, 2010, Office Action.
U.S. Appl. No. 12/402,398, field Sep. 20, 2012, Office Action.

(56) References Cited

OTHER PUBLICATIONS

U.S. Appl. No. 12/688,065, filed Oct. 12, 2012, Office Action.
U.S. Appl. No. 12/848,642, filed Sep. 20, 2012, Office Action.
U.S. Appl. No. 12/897,358, filed Oct. 4, 2010, Carley.
U.S. Appl. No. 12/113,851, filed Dec. 16, 2010, Office Action.
U.S. Appl. No. 12/114,091, filed Dec. 17, 2010, Office Action.
U.S. Appl. No. 60/711,279, filed Aug. 24, 2005, Sibbitt Jr. et al.
U.S. Appl. No. 60/726,985, filed Oct. 14, 2005, Sibbitt Jr. et al.
U.S. Appl. No. 60/793,444, filed Apr. 20, 2006, Jones et al.
U.S. Appl. No. 61/097,072, filed Sep. 15, 2008, Sibbitt Jr. et al.
U.S. Appl. No. 61/139,995, filed Dec. 22, 2008, Clark.
U.S. Appl. No. 61/141,597, filed Dec. 30, 2008, Clark.
U.S. Appl. No. 12/481,377, filed Jun. 9, 2009, Clark.
U.S. Appl. No. 12/642,319, filed Dec. 18, 2009, Clark.
U.S. Appl. No. 10/006,400, filed Apr. 27, 2010, Notice of Allowance.
U.S. Appl. No. 10/147,774, filed Jun. 8, 2010, Office Action.
U.S. Appl. No. 10/264,306, filed Jun. 15, 2010, Office Action.
U.S. Appl. No. 10/356,214, filed May 13, 2010, Notice of Allowance.
U.S. Appl. No. 10/435,104, filed Jun. 2, 2010, Office Action.
U.S. Appl. No. 10/541,083, filed May 10, 2010, Notice of Allowance.
U.S. Appl. No. 10/616,832, filed May 12, 2010, Notice of Allowance.
U.S. Appl. No. 10/667,144, filed Jun. 22, 2010, Office Action.
U.S. Appl. No. 11/048,503, filed Apr. 26, 2010, Notice of Allowance.
U.S. Appl. No. 11/198,811, filed Jun. 29, 2010, Notice of Allowance.
U.S. Appl. No. 11/316,775, filed Apr. 16, 2008, Office Action.
U.S. Appl. No. 11/316,775, filed Aug. 6, 2008, Office Action.
U.S. Appl. No. 11/344,891, filed May 7, 2010, Office Action.
U.S. Appl. No. 11/390,586, filed Jul. 6, 2010, Office Action.
U.S. Appl. No. 11/396,141, filed May 4, 2010, Office Action.
U.S. Appl. No. 11/396,731, filed Jun. 29, 2010, Office Action.
U.S. Appl. No. 11/406,203, filed Jun. 18, 2010, Notice of Allowance.
U.S. Appl. No. 11/508,656, filed Dec. 9, 2009, Office Action.
U.S. Appl. No. 11/508,656, filed Mar. 25, 2010, Office Action.
U.S. Appl. No. 11/508,662, filed Dec. 28, 2009, Office Action.
U.S. Appl. No. 11/508,662, filed Apr. 14, 2010, Office Action.
U.S. Appl. No. 11/508,715, filed Jan. 6, 2010, Office Action.
U.S. Appl. No. 11/508,715, filed Apr. 26, 2010, Office Action.
U.S. Appl. No. 11/674,930, filed Jan. 8, 2009, Office Action.
U.S. Appl. No. 11/674,930, filed Jun. 4, 2009, Office Action.
U.S. Appl. No. 11/674,930, filed Jan. 8, 2010, Office Action.
U.S. Appl. No. 11/852,190, filed Jun. 24, 2010, Office Action.
U.S. Appl. No. 11/958,295, filed May 25, 2010, Office Action.
U.S. Appl. No. 12/106,928, filed May 10, 2010, Office Action.
U.S. Appl. No. 12/113,851, filed Apr. 27, 2010, Office Action.
U.S. Appl. No. 12/113,851, filed Jun. 24, 2010, Office Action.
U.S. Appl. No. 12/402,398, filed May 20, 2010, Office Action.
U.S. Appl. No. 11/198,811, filed Oct. 20, 2010, Issue Notification.
U.S. Appl. No. 11/508,662, filed Oct. 26, 2010, Office Action.
U.S. Appl. No. 11/852,190, filed Nov. 1, 2010, Office Action.
U.S. Appl. No. 12/114,091, filed Oct. 27, 2010, Office Action.
U.S. Appl. No. 12/114,091, filed Apr. 5, 2012, Office Action.
U.S. Appl. No. 12/684,542, filed Apr. 16, 2012, Office Action.
U.S. Appl. No. 12/897,358, filed Jan. 12, 2012, Notice of Allowance.
U.S. Appl. No. 12/338,977, filed Jan. 19, 2012, Office Action.
U.S. Appl. No. 12/684,569, filed Jan. 27, 2012, Office Action.
U.S. Appl. No. 13/017,636, filed Jan. 31, 2011, Carley et al.
U.S. Appl. No. 13/026,989, filed Feb. 14, 2011, Cummins.
U.S. Appl. No. 10/264,306, filed Feb. 16, 2011, Issue Notification.
U.S. Appl. No. 11/767,818, filed Feb. 18, 2011, Office Action.
U.S. Appl. No. 10/667,144, filed Feb. 15, 2012, Issue Notification.
U.S. Appl. No. 12/135,858, filed Feb. 16, 2012, Office Action.
U.S. Appl. No. 12/684,562, filed Feb. 16, 2012, Office Action.
U.S. Appl. No. 12/945,646, filed Feb. 21, 2012, Notice of Allowance.
U.S. Appl. No. 13/030,922, filed Feb. 18, 2011, Cummins.
U.S. Appl. No. 13/039,087, filed Mar. 2, 2011, Palermo et al.
U.S. Appl. No. 10/356,214, filed Feb. 23, 2011, Issue Notification.
U.S. Appl. No. 11/852,190, filed Mar. 2, 2011, Office Action.
U.S. Appl. No. 12/122,603, filed Mar. 3, 2011, Office Action.
U.S. Appl. No. 11/396,731, filed Mar. 22, 2011, Office Action.
U.S. Appl. No. 11/427,297, filed Mar. 21, 2011, Office Action.
U.S. Appl. No. 10/682,459, filed Apr. 1, 2011, Notice of Allowance.
U.S. Appl. No. 12/403,277, filed Mar. 31, 2011, Office Action.
U.S. Appl. No. 13/791,829, filed Mar. 8, 2013, Roorda et al.
U.S. Appl. No. 13/791,846, filed Mar. 8, 2013, Palermo.
U.S. Appl. No. 13/112,618, filed Mar. 29, 2013, Office Action.
U.S. Appl. No. 13/112,631, filed Mar. 29, 2013, Office Action.
U.S. Appl. No. 13/308,227, filed Apr. 10, 2013, Office Action.
U.S. Appl. No. 13/525,839, filed Apr. 1, 2013, Office Action.
U.S. Appl. No. 10/147,774, filed Apr. 6, 2011, Issue Notification.
U.S. Appl. No. 11/744,089, filed Apr. 15, 2013, Office Action.
U.S. Appl. No. 12/850,242, filed Apr. 18, 2013, Office Action.
U.S. Appl. No. 13/052,634, filed Feb. 8, 2013, Office Action.
U.S. Appl. No. 13/052,634, filed Apr. 22, 2013, Office Action.
U.S. Appl. No. 13/615,547, filed Apr. 12, 2013, Notice of Allowance.
U.S. Appl. No. 13/308,227, filed Nov. 30, 2011, Yibarren.
U.S. Appl. No. 12/688,065, filed Apr. 26, 2012, Office Action.
U.S. Appl. No. 12/607,769, filed Aug. 22, 2012, Office Action.
U.S. Appl. No. 12/642,319, filed Aug. 28, 2012, Office Action.
U.S. Appl. No. 12/684,562, filed Aug. 21, 2012, Office Action.
U.S. Appl. No. 13/222,899, filed Aug. 31, 2011, Carley et al.
U.S. Appl. No. 12/143,020, filed Aug. 31, 2011, Office Action.
U.S. Appl. No. 12/897,358, filed Aug. 22, 2011, Office Action.
U.S. Appl. No. 13/026,989, filed Sep. 16, 2011, Office Action.
U.S. Appl. No. 10/264,306, filed Oct. 29, 2010, Notice of Allowance.
U.S. Appl. No. 10/356,214, filed Sep. 3, 2010, Notice of Allowance.
U.S. Appl. No. 10/682,459, filed Oct. 12, 2010, Office Action.
U.S. Appl. No. 11/406,203, filed Oct. 6, 2010, Issue Notification.
U.S. Appl. No. 11/508,715, filed Oct. 18, 2010, Office Action.
U.S. Appl. No. 11/532,576, filed Oct. 13, 2010, Notice of Allowance.
U.S. Appl. No. 11/958,281, filed Oct. 8, 2010, Office Action.
U.S. Appl. No. 12/114,031, filed Oct. 5, 2010, Office Action.
U.S. Appl. No. 12/403,277, filed Oct. 12, 2010, Office Action.
U.S. Appl. No. 11/427,309, filed Nov. 15, 2010, Office Action.
U.S. Appl. No. 11/675,462, filed Dec. 22, 2011, Notice of Allowance.
U.S. Appl. No. 12/684,470, filed Dec. 20, 2011, Restriction Requirement.
U.S. Appl. No. 12/684,569, filed Dec. 20, 2011, Restriction Requirement.
U.S. Appl. No. 12/608,773, filed Jan. 7, 2013, Office Action.
U.S. Appl. No. 13/490,143, filed Jan. 4, 2013, Retriction Requirement.
U.S. Appl. No. 13/615,547, filed Jan. 18, 2013, Office Action.
U.S. Appl. No. 10/616,832, filed Jan. 26, 2011, Issue Notification.
U.S. Appl. No. 11/152,562, filed Jan. 26, 2011, Issue Notification.
U.S. Appl. No. 11/767,818, filed Feb. 3, 2012, Notice of Allowance.
U.S. Appl. No. 12/684,542, filed Jan. 30, 2012, Office Action.
U.S. Appl. No. 12/941,809, filed Jan. 30, 2012, Office Action.
U.S. Appl. No. 12/966,923, filed Feb. 3, 2012, Notice of Allowance.
U.S. Appl. No. 12/961,331, filed Feb. 1, 2013, Office Action.
U.S. Appl. No. 13/488,233, filed Feb. 5, 2013, Notice of Allowance.
U.S. Appl. No. 12/608,769, filed Feb. 10, 2012, Office Action.
U.S. Appl. No. 12/684,400, filed Feb. 13, 2012, Office Action.
U.S. Appl. No. 12/724,304, filed Feb. 10, 2012, Office Action.
U.S. Appl. No. 12/143,020, filed Feb. 23, 2012, Notice of Allowance.
U.S. Appl. No. 12/548,274, filed Mar. 2, 2012, Office Action.
U.S. Appl. No. 12/642,319, filed Feb. 27, 2012, Office Action.
U.S. Appl. No. 11/532,576, filed Mar. 16, 2011, Issue Notification.
U.S. Appl. No. 12/114,031, filed Mar. 6, 2012, Office Action.
U.S. Appl. No. 12/684,470, filed Mar. 23, 2012, Office Action.
U.S. Appl. No. 12/688,065, filed Mar. 13, 2012, Office Action.
U.S. Appl. No. 12/897,358, filed Mar. 5, 2012, Notice of Allowance.
U.S. Appl. No. 12/973,204, filed Mar. 7, 2012, Notice of Allowance.
U.S. Appl. No. 12/987,792, filed Mar. 13, 2012, Office Action.
U.S. Appl. No. 12/113,851, filed Mar. 29, 2012, Office Action.
U.S. Appl. No. 12/403,277, filed Apr. 3, 2012, Office Action.
U.S. Appl. No. 60/696,069, filed Jul. 1, 2005, Pantages et al.
U.S. Appl. No. 60/693,531, filed Jun. 24, 2005, Carly.
U.S. Appl. No. 60/843,325, filed Sep. 8, 2006, Carly.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 12/113,092, filed Apr. 30, 2008, Ginn et al.
U.S. Appl. No. 12/393,877, filed Feb. 26, 2009, Ellingwood et al.

(56) References Cited

OTHER PUBLICATIONS

U.S. Appl. No. 12/403,277, filed Mar. 12, 2009, Coleman et al.
"Hand tool for forming telephone connections—comprises pliers with reciprocably driven ram crimping clip around conductors against anvil".
Database WPI; Section PQ, Week 200120; Derwent Publications Ltd., London GB; Class P31, AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62 —No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PhD, Wound Closure Biomaterials and Devices, Shock., Mar. 1999, p. 226, vol. 11—No. 3, Institution Northwestern University.
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
McCarthy, et al., "Tension (Stay) Suture Bridge", J. of International College of Surgeons, 34(5), pp. 613-614 (Nov. 1960). cited by other.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Stretch Comb by Scunci, retrieved via internet at www.scunci.com/productdetail by examiner on Oct. 9, 2007, publication date unavailable.
Swee Lian Tan, MD, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.
UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.
U.S. Appl. No. 09/478,179, filed Nov. 6, 2000, Notice of Allowance.
U.S. Appl. No. 09/478,179, filed Feb. 15, 2001, Issue Notification.
U.S. Appl. No. 09/546,998, filed May 6, 2002, Notice of Allowance.
U.S. Appl. No. 09/546,998, filed Sep. 19, 2002, Issue Notification.
U.S. Appl. No. 09/610,238, filed Mar. 26, 2001, Notice of Allowance.
U.S. Appl. No. 09/610,238, filed Sep. 5, 2001, Office Action.
U.S. Appl. No. 09/610,238, filed Feb. 11, 2002, Notice of Allowance.
U.S. Appl. No. 09/610,238, filed May 3, 2002, Issue Notification.
U.S. Appl. No. 09/680,837, filed Jul. 9, 2002, Office Action.
U.S. Appl. No. 09/680,837, filed Nov. 6, 2002, Office Action.
U.S. Appl. No. 09/680,837, filed Mar. 25, 2003, Office Action.
U.S. Appl. No. 09/680,837, filed Jun. 16, 2003, Notice of Allowance.
U.S. Appl. No. 09/680,837, filed Sep. 11, 2003, Issue Notification.

(56) References Cited

OTHER PUBLICATIONS

U.S. Appl. No. 09/732,178, filed Aug. 1, 2002, Office Action.
U.S. Appl. No. 09/732,178, filed Dec. 24, 2002, Office Action.
U.S. Appl. No. 09/732,178, filed Jun. 10, 2003, Office Action.
U.S. Appl. No. 09/732,178, filed Jul. 3, 2003, Office Action.
U.S. Appl. No. 09/732,178, filed Nov. 17, 2003, Notice of Allowance.
U.S. Appl. No. 09/732,178, filed Mar. 25, 2004, Issue Notification.
U.S. Appl. No. 09/732,835, filed Sep. 11, 2003, Office Action.
U.S. Appl. No. 09/732,835, filed Feb. 9, 2004, Office Action.
U.S. Appl. No. 09/732,835, filed Mar. 17, 2004, Notice of Allowance.
U.S. Appl. No. 09/764,813, filed Mar. 26, 2001, Office Action.
U.S. Appl. No. 09/764,813, filed Jun. 4, 2001, Notice of Allowance.
U.S. Appl. No. 09/764,813, filed Aug. 6, 2001, Issue Notification.
U.S. Appl. No. 09/933,299, filed Feb. 26, 2003, Office Action.
U.S. Appl. No. 09/933,299, filed Jun. 16, 2003, Notice of Allowance.
U.S. Appl. No. 09/933,299, filed Sep. 25, 2003, Issue Notification.
U.S. Appl. No. 09/948,813, filed Jan. 31, 2003, Notice of Allowance.
U.S. Appl. No. 09/948,813, filed Jun. 5, 2003, Issue Notification.
U.S. Appl. No. 09/949,398, filed Mar. 4, 2003, Office Action.
U.S. Appl. No. 09/949,398, filed Jul. 28, 2003, Notice of Allowance.
U.S. Appl. No. 09/949,398, filed Dec. 11, 2003, Issue Notification.
U.S. Appl. No. 09/949,438, filed Dec. 17, 2002, Office Action.
U.S. Appl. No. 09/949,438, filed Apr. 21, 2003, Notice of Allowance.
U.S. Appl. No. 09/949,438, filed Aug. 21, 2003, Issue Notification.
U.S. Appl. No. 10/006,400, filed Aug. 27, 2004, Office Action.
U.S. Appl. No. 10/006,400, filed Feb. 23, 2005, Office Action.
U.S. Appl. No. 10/006,400, filed Apr. 11, 2005, Office Action.
U.S. Appl. No. 10/006,400, filed Jul. 27, 2005, Office Action.
U.S. Appl. No. 10/006,400, filed Mar. 6, 2006, Office Action.
U.S. Appl. No. 10/006,400, filed May 24, 2006, Office Action.
U.S. Appl. No. 10/006,400, filed Oct. 26, 2006, Office Action.
U.S. Appl. No. 10/006,400, filed Apr. 19, 2007, Office Action.
U.S. Appl. No. 10/006,400, filed Apr. 2, 2008, Office Action.
U.S. Appl. No. 10/006,400, filed Jan. 2, 2009, Office Action.
U.S. Appl. No. 10/006,400, filed Jul. 9, 2009, Notice of Allowance.
U.S. Appl. No. 10/006,400, filed Jan. 13, 2010, Notice of Allowance.
U.S. Appl. No. 10/081,717, filed Sep. 29, 2003, Notice of Allowance.
U.S. Appl. No. 10/081,717, filed Feb. 5, 2004, Issue Notification.
U.S. Appl. No. 10/081,723, filed Sep. 29, 2004, Office Action.
U.S. Appl. No. 10/081,723, filed May 13, 2005, Notice of Allowance.
U.S. Appl. No. 10/081,725, filed Feb. 9, 2004, Notice of Allowance.
U.S. Appl. No. 10/081,725, filed Apr. 13, 2004, Office Action.
U.S. Appl. No. 10/081,725, filed May 27, 2004, Issue Notification.
U.S. Appl. No. 10/081,726, filed Apr. 11, 2003, Notice of Allowance.
U.S. Appl. No. 10/081,726, filed Jun. 9, 2003, Notice of Allowance.
U.S. Appl. No. 10/081,726, filed Sep. 4, 2003, Issue Notification.
U.S. Appl. No. 10/147,774, filed Nov. 4, 2004, Office Action.
U.S. Appl. No. 10/147,774, filed May 4, 2005, Office Action.
U.S. Appl. No. 10/147,774, filed Oct. 18, 2005, Office Action.
U.S. Appl. No. 10/147,774, filed Apr. 18, 2007, Notice of Allowance.
U.S. Appl. No. 10/147,774, filed Sep. 27, 2007, Notice of Allowance.
U.S. Appl. No. 10/147,774, filed Feb. 4, 2008, Notice of Allowance.
U.S. Appl. No. 10/147,774, filed Jun. 30, 2008, Office Action.
U.S. Appl. No. 10/147,774, filed Mar. 18, 2009, Office Action.
U.S. Appl. No. 10/147,774, filed Oct. 26, 2009, Office Action.
U.S. Appl. No. 10/240,183, filed Jul. 27, 2004, Office Action.
U.S. Appl. No. 10/240,183, filed Dec. 17, 2004, Office Action.
U.S. Appl. No. 10/240,183, filed Mar. 9, 2005, Notice of Allowance.
U.S. Appl. No. 10/240,183, filed Aug. 11, 2006, Office Action.
U.S. Appl. No. 10/264,306, filed Feb. 9, 2005, Office Action.
U.S. Appl. No. 10/264,306, filed May 26, 2005, Office Action.
U.S. Appl. No. 10/264,306, filed Oct. 4, 2005, Office Action.
U.S. Appl. No. 10/264,306, filed May 10, 2006, Notice of Allowance.
U.S. Appl. No. 10/264,306, filed Jul. 2, 2007, Notice of Allowance.
U.S. Appl. No. 10/264,306, filed Feb. 4, 2008, Notice of Allowance.
U.S. Appl. No. 10/264,306, filed Jun. 27, 2008, Office Action.
U.S. Appl. No. 10/264,306, filed Feb. 26, 2009, Office Action.
U.S. Appl. No. 10/264,306, filed Aug. 13, 2009, Office Action.
U.S. Appl. No. 10/264,306, filed Jan. 27, 2010, Office Action.
U.S. Appl. No. 10/305,923, filed Nov. 1, 2004, Office Action.
U.S. Appl. No. 10/305,923, filed Mar. 3, 2005, Notice of Allowance.
U.S. Appl. No. 10/335,075, filed Aug. 10, 2005, Office Action.
U.S. Appl. No. 10/335,075, filed Dec. 19, 2005, Office Action.
U.S. Appl. No. 10/335,075, filed Apr. 21, 2006, Office Action.
U.S. Appl. No. 10/335,075, filed Dec. 27, 2006, Notice of Allowance.
U.S. Appl. No. 10/335,075, filed Apr. 11, 2007, Issue Notification.
U.S. Appl. No. 10/356,214, filed Nov. 30, 2005, Office Action.
U.S. Appl. No. 10/356,214, filed Aug. 23, 2006, Office Action.
U.S. Appl. No. 10/356,214, filed Feb. 13, 2007, Office Action.
U.S. Appl. No. 10/356,214, filed Sep. 12, 2007, Office Action.
U.S. Appl. No. 10/356,214, filed Mar. 6, 2008, Office Action.
U.S. Appl. No. 10/356,214, filed Nov. 4, 2008, Office Action.
U.S. Appl. No. 10/356,214, filed Apr. 29, 2009, Office Action.
U.S. Appl. No. 10/356,214, filed Jan. 13, 2010, Notice of Allowance.
U.S. Appl. No. 10/435,104, filed Jun. 10, 2004, Office Action.
U.S. Appl. No. 10/435,104, filed Sep. 21, 2004, Notice of Allowance.
U.S. Appl. No. 10/435,104, filed Jan. 3, 2006, Examiner's Amendment.
U.S. Appl. No. 10/435,104, filed Feb. 15, 2006, Issue Notification.
U.S. Appl. No. 10/435,104, filed May 16, 2006, Office Action.
U.S. Appl. No. 10/435,104, filed Dec. 28, 2006, Notice of Allowance.
U.S. Appl. No. 10/435,104, filed May 23, 2007, Issue Notification.
U.S. Appl. No. 10/435,104, filed Jul. 10, 2007, Notice of Allowance.
U.S. Appl. No. 10/435,104, filed Aug. 2, 2007, Supplemental Notice of Allowance.
U.S. Appl. No. 10/435,104, filed Oct. 26, 2007, Notice of Allowance.
U.S. Appl. No. 10/435,104, filed Nov. 14, 2007, Supplemental Notice of Allowance.
U.S. Appl. No. 10/435,104, filed Apr. 4, 2008, Notice of Allowance.
U.S. Appl. No. 10/435,104, filed Sep. 26, 2008, Notice of Allowance.
U.S. Appl. No. 10/435,104, filed Dec. 22, 2008, Supplemental Notice of Allowance.
U.S. Appl. No. 10/435,104, filed Jan. 20, 2010, Notice of Allowance.
U.S. Appl. No. 10/455,768, filed Nov. 16, 2004, Office Action.
U.S. Appl. No. 10/455,768, filed Apr. 6, 2005, Notice of Allowance.
U.S. Appl. No. 10/486,067, filed Jan. 10, 2006, Office Action.
U.S. Appl. No. 10/486,067, filed Sep. 20, 2006, Notice of Allowance.
U.S. Appl. No. 10/486,067, filed Dec. 27, 2006, Issue Notification.
U.S. Appl. No. 10/486,070, filed Apr. 20, 2005, Office Action.
U.S. Appl. No. 10/486,070, filed Aug. 10, 2005, Office Action.
U.S. Appl. No. 10/486,070, filed Oct. 18, 2005, Notice of Allowance.
U.S. Appl. No. 10/517,004, filed Aug. 13, 2007, Office Action.
U.S. Appl. No. 10/517,004, filed Jan. 30, 2008, Office Action.
U.S. Appl. No. 10/517,004, filed Aug. 13, 2008, Notice of Allowance.
U.S. Appl. No. 10/517,004, filed Feb. 10, 2009, Notice of Allowance.
U.S. Appl. No. 10/517,004, filed Mar. 24, 2009, SNotice of Allowance.
U.S. Appl. No. 10/517,004, filed Jun. 26, 2009, Notice of Allowance.
U.S. Appl. No. 10/517,004, filed Jan. 11, 2010, Notice of Allowance.
U.S. Appl. No. 10/519,778, filed Feb. 23, 2006, Office Action.
U.S. Appl. No. 10/519,778, filed May 31, 2006, Notice of Allowance.
U.S. Appl. No. 10/541,083, filed Oct. 16, 2007, Office Action.
U.S. Appl. No. 10/541,083, filed Oct. 31, 2007, Office Action.
U.S. Appl. No. 10/541,083, filed May 5, 2008, Office Action.
U.S. Appl. No. 10/541,083, filed Sep. 19, 2008, Notice of Allowance.
U.S. Appl. No. 10/541,083, filed Dec. 29, 2008, Notice of Allowance.
U.S. Appl. No. 10/541,083, filed Apr. 16, 2009, Notice of Allowance.
U.S. Appl. No. 10/541,083, filed Feb. 5, 2010, Notice of Allowance.
U.S. Appl. No. 10/616,832, filed Jun. 30, 2006, Office Action.
U.S. Appl. No. 10/616,832, filed Oct. 20, 2006, Office Action.
U.S. Appl. No. 10/616,832, filed May 29, 2007, Office Action.
U.S. Appl. No. 10/616,832, filed Jan. 22, 2008, Office Action.
U.S. Appl. No. 10/616,832, filed Jan. 11, 2010, Notice of Allowance.
U.S. Appl. No. 10/541,083, filed Sep. 30, 2009, Notice of Allowance.
U.S. Appl. No. 10/616,832, filed Sep. 17, 2008, Office Action.
U.S. Appl. No. 10/616,832, filed Jul. 21, 2009, Office Action.
U.S. Appl. No. 10/617,090, filed Mar. 22, 2005, Office Action.
U.S. Appl. No. 10/617,090, filed Jul. 6, 2005, Notice of Allowance.
U.S. Appl. No. 10/617,090, filed Oct. 5, 2005, Notice of Allowance.
U.S. Appl. No. 10/617,090, filed Feb. 1, 2006, Issue Notification.
U.S. Appl. No. 10/638,115, filed Sep. 22, 2006, Office Action.
U.S. Appl. No. 10/638,115, filed Jan. 31, 2007, Office Action.
U.S. Appl. No. 10/638,115, filed Sep. 18, 2007, Office Action.

(56) References Cited

OTHER PUBLICATIONS

U.S. Appl. No. 10/638,115, filed Feb. 7, 2008, Office Action.
U.S. Appl. No. 10/638,115, filed Oct. 29, 2008, Office Action.
U.S. Appl. No. 10/638,115, filed May 7, 2009, Notice of Allowance.
U.S. Appl. No. 10/638,115, filed Dec. 1, 2009, Notice of Allowance.
U.S. Appl. No. 10/638,115, filed Apr. 2, 2010, Notice of Allowance.
U.S. Appl. No. 10/667,144, filed Sep. 19, 2006, Office Action.
U.S. Appl. No. 10/667,144, filed May 2, 2007, Office Action.
U.S. Appl. No. 10/667,144, filed Nov. 19, 2007, Office Action.
U.S. Appl. No. 10/667,144, filed Dec. 5, 2007, Office Action.
U.S. Appl. No. 10/667,144, filed May 12, 2008, Office Action.
U.S. Appl. No. 10/667,144, filed Mar. 24, 2009, Office Action.
U.S. Appl. No. 10/667,144, filed Nov. 23, 2009, Office Action.
U.S. Appl. No. 10/669,313, filed Jan. 11, 2006, Notice of Allowance.
U.S. Appl. No. 10/669,313, filed Jun. 28, 2006, Notice of Allowance.
U.S. Appl. No. 10/669,313, filed Nov. 15, 2006, Issue Notification.
U.S. Appl. No. 10/682,459, filed Sep. 15, 2006, Office Action.
U.S. Appl. No. 10/682,459, filed Apr. 18, 2007, Office Action.
U.S. Appl. No. 10/682,459, filed Apr. 2, 2008, Office Action.
U.S. Appl. No. 10/682,459, filed Dec. 4, 2008, Office Action.
U.S. Appl. No. 10/682,459, filed Jun. 10, 2009, Office Action.
U.S. Appl. No. 10/682,459, filed Dec. 23, 2009, Office Action.
U.S. Appl. No. 10/786,444, filed Oct. 30, 2006, Office Action.
U.S. Appl. No. 10/786,444, filed Apr. 17, 2007, Office Action.
U.S. Appl. No. 10/786,444, filed Aug. 31, 2007, Office Action.
U.S. Appl. No. 10/786,444, filed Apr. 24, 2008, Office Action.
U.S. Appl. No. 10/786,444, filed Oct. 17, 2008, Office Action.
U.S. Appl. No. 10/786,444, filed Jun. 18, 2009, Office Action.
U.S. Appl. No. 10/786,444, filed Jan. 14, 2010, Office Action.
U.S. Appl. No. 10/787,073, filed Nov. 30, 2006, Office Action.
U.S. Appl. No. 10/787,073, filed Sep. 5, 2007, Office Action.
U.S. Appl. No. 10/787,073, filed Feb. 22, 2008, Office Action.
U.S. Appl. No. 10/787,073, filed Nov. 12, 2008, Office Action.
U.S. Appl. No. 10/787,073, filed Aug. 13, 2009, Office Action.
U.S. Appl. No. 10/787,073, filed Feb. 17, 2010, Notice of Allowance.
U.S. Appl. No. 10/908,721, filed Oct. 19, 2006, Office Action.
U.S. Appl. No. 10/908,721, filed Aug. 10, 2007, Office Action.
U.S. Appl. No. 10/908,721, filed Jan. 25, 2008, Office Action.
U.S. Appl. No. 10/908,721, filed Nov. 25, 2008, Office Action.
U.S. Appl. No. 10/908,721, filed Jun. 23, 2009, Office Action.
U.S. Appl. No. 10/908,721, filed Feb. 2, 2010, Office Action.
U.S. Appl. No. 11/048,503, filed Mar. 13, 2009, Office Action.
U.S. Appl. No. 11/048,503, filed Jun. 26, 2009, Office Action.
U.S. Appl. No. 11/048,503, filed Jan. 11, 2010, Notice of Allowance.
U.S. Appl. No. 11/113,549, filed Feb. 6, 2007, Office Action.
U.S. Appl. No. 11/113,549, filed May 30, 2007, Office Action.
U.S. Appl. No. 11/113,549, filed Nov. 9, 2007, Office Action.
U.S. Appl. No. 11/113,549, filed Apr. 16, 2008, Office Action.
U.S. Appl. No. 11/113,549, filed Jul. 21, 2009, Office Action.
U.S. Appl. No. 11/152,562, filed May 13, 2008, Office Action.
U.S. Appl. No. 11/152,562, filed Feb. 13, 2009, Office Action.
U.S. Appl. No. 11/152,562, filed Jul. 6, 2009, Office Action.
U.S. Appl. No. 11/152,562, filed Mar. 31, 2010, Office Action.
U.S. Appl. No. 11/198,811, filed Aug. 26, 2008, Office Action.
U.S. Appl. No. 11/198,811, filed Apr. 6, 2009, Office Action.
U.S. Appl. No. 11/198,811, filed Sep. 22, 2009, Office Action.
U.S. Appl. No. 11/344,793, filed Jan. 22, 2009, Office Action.
U.S. Appl. No. 11/344,868, filed Mar. 25, 2009, Office Action.
U.S. Appl. No. 11/344,891, filed Apr. 29, 2008, Office Action.
U.S. Appl. No. 11/344,891, filed Dec. 8, 2008, Office Action.
U.S. Appl. No. 11/344,891, filed Feb. 26, 2009, Office Action.
U.S. Appl. No. 11/344,891, filed Oct. 7, 2009, Office Action.
U.S. Appl. No. 11/390,586, filed Jun. 24, 2009, Office Action.
U.S. Appl. No. 11/396,141, filed May 22, 2009, Office Action.
U.S. Appl. No. 11/396,141, filed Aug. 26, 2009, Office Action.
U.S. Appl. No. 11/396,731, filed Feb. 13, 2009, Office Action.
U.S. Appl. No. 11/396,731, filed May 22, 2009, Office Action.
U.S. Appl. No. 11/406,203, filed May 14, 2007, Office Action.
U.S. Appl. No. 11/406,203, filed Jan. 29, 2008, Notice of Allowance.
U.S. Appl. No. 11/406,203, filed May 23, 2008, Notice of Allowance.
U.S. Appl. No. 11/406,203, filed Sep. 22, 2008, Notice of Allowance.
U.S. Appl. No. 11/406,203, filed Mar. 3, 2009, Office Action.
U.S. Appl. No. 11/406,203, filed Sep. 16, 2009, Office Action.
U.S. Appl. No. 11/411,925, filed Jun. 6, 2007, Office Action.
U.S. Appl. No. 11/411,925, filed Feb. 5, 2008, Office Action.
U.S. Appl. No. 11/411,925, filed Jan. 12, 2009, Office Action.
U.S. Appl. No. 11/411,925, filed Sep. 10, 2009 , Office Action.
U.S. Appl. No. 11/427,297, filed Jan. 30, 2009, Office Action.
U.S. Appl. No. 11/427,297, filed Sep. 15, 2009, Office Action.
U.S. Appl. No. 11/461,323, filed May 2, 2007, Office Action.
U.S. Appl. No. 11/461,323, filed Oct. 29, 2007, Office Action.
U.S. Appl. No. 11/461,323, filed Apr. 25, 2008, Office Action.
U.S. Appl. No. 11/461,323, filed Nov. 6, 2008, Office Action.
U.S. Appl. No. 11/461,323, filed Jul. 27, 2009, Office Action.
U.S. Appl. No. 11/461,323, filed Apr. 5, 2010, Notice of Allowance.
U.S. Appl. No. 11/532,325, filed Feb. 23, 2009, Office Action.
U.S. Appl. No. 11/532,325, filed Jun. 17, 2009, Office Action.
U.S. Appl. No. 11/532,325, filed Jan. 5, 2010, Office Action.
U.S. Appl. No. 11/532,576, filed Mar. 1, 2010, Office Action.
U.S. Appl. No. 11/675,462, filed Dec. 10, 2009, Office Action.
U.S. Appl. No. 11/744,089, filed Nov. 26, 2008, Office Action.
U.S. Appl. No. 11/744,089, filed Aug. 14, 2009, Office Action.
U.S. Appl. No. 11/767,818, filed Dec. 24, 2009, Office Action.
U.S. Appl. No. 11/767,818, filed Mar. 22, 2010, Office Action.
U.S. Appl. No. 11/958,295, filed Aug. 27, 2009, Office Action.
U.S. Appl. No. 11/959,334, filed Aug. 19, 2009, Office Action.
U.S. Appl. No. 11/959,334, filed Jan. 12, 2010, Notice of Allowance.
U.S. Appl. No. 11/959,334, filed Apr. 14, 2010, Notice of Allowance.
U.S. Appl. No. 12/106,937, filed Mar. 30, 2009, Office Action.
U.S. Appl. No. 12/106,937, filed Nov. 18, 2009, Office Action.
U.S. Appl. No. 12/106,928, filed Jan. 23, 2009, Office Action.
U.S. Appl. No. 12/106,928, filed Oct. 5, 2009, Office Action.
U.S. Appl. No. 12/402,398, filed Mar. 9, 2010, Office Action.
U.S. Appl. No. 12/403,256, filed Dec. 16, 2009, Office Action.
U.S. Appl. No. 12/403,256, filed Mar. 30, 2010, Office Action.
U.S. Appl. No. 10/517,004, filed Apr. 23, 2010, Notice of Allowance.
U.S. Appl. No. 11/532,576, filed Apr. 23, 2010, Office Action.
U.S. Appl. No. 29/296,370, filed Aug. 18, 2008, Office Action.
U.S. Appl. No. 29/296,370, filed Dec. 2, 2008, Notice of Allowance.
U.S. Appl. No. 29/296,370, filed Apr. 1, 2009, Notice of Allowance.
U.S. Appl. No. 29/296,370, filed Feb. 10, 2010, Issue Notification.
U.S. Appl. No. 13/112,618, filed May 20, 2011, Gianotti et al.
U.S. Appl. No. 13/112,631, filed May 20, 2011, Voss.
U.S. Appl. No. 12/955,859, filed May 26, 2011, Office Action.
U.S. Appl. No. 12/114,091, filed Jul. 7, 2011, Office Action.
U.S. Appl. No. 12/945,646, filed Jul. 6, 2011, Office Action.
U.S. Appl. No. 12/955,859, filed Jul. 21, 2011, Office Action.
U.S. Appl. No. 11/390,586, filed Jul. 18, 2012, Issue Notification.
U.S. Appl. No. 12/608,773, filed Jul. 20, 2012, Office Action.
U.S. Appl. No. 12/684,569, filed Jul. 30, 2012, Office Action.
U.S. Appl. No. 13/039,087, filed Jul. 17, 2012, Office Action.
U.S. Appl. No. 11/427,297, filed Oct. 31, 2012, Issue Notification.
U.S. Appl. No. 12/114,091, filed Nov. 8, 2012, Office Action.
U.S. Appl. No. 12/403,277, filed Nov. 5, 2012, Office Action.
U.S. Appl. No. 12/608,769, filed Nov. 5, 2012, Notice of Allowance.
U.S. Appl. No. 12/684,400, filed Oct. 16, 2012, Office Action.
U.S. Appl. No. 12/848,642, filed Nov. 9, 2012, Office Action.
U.S. Appl. No. 12/850,242, filed Oct. 17, 2012, Office Action.
U.S. Appl. No. 13/039,087, filed Nov. 6, 2012, Notice of Allowance.
U.S. Appl. No. 10/638,115, filed Dec. 22, 2010, Issue Notification.
U.S. Appl. No. 12/941,809, filed Nov. 8, 2010, Ginn et al.
U.S. Appl. No. 12/950,628, filed Nov. 19, 2010, Walberg et al.
U.S. Appl. No. 12/955,859, filed Nov. 29, 2010, Ginn.
U.S. Appl. No. 12/945,646, filed Nov. 12, 2010, Carley et al.
U.S. Appl. No. 12/973,204, filed Dec. 20, 2010, Jabba et al.
U.S. Appl. No. 12/987,792, filed Jan. 10, 2011, Palermo et al.
U.S. Appl. No. 10/435,104, filed Jan. 12, 2011, Issue Notification.
U.S. Appl. No. 12/402,398, filed Jan. 24, 2011, Office Action.
U.S. Appl. No. 12/945,646, filed Jan. 20, 2011, Office Action.
U.S. Appl. No. 11/396,731, filed Sep. 1, 2011, Office Action.
U.S. Appl. No. 10/667,144, filed Oct. 28, 2011, Notice of Allowance.
U.S. Appl. No. 12/945,646, filed Oct. 26, 2011, Office Action.
U.S. Appl. No. 12/106,928, filed Oct. 25, 2010, Office Action.

(56) References Cited

OTHER PUBLICATIONS

U.S. Appl. No. 12/961,331, filed Dec. 6, 2010, Voss.
U.S. Appl. No. 12/966,923, filed Dec. 13, 2010, Cummins et al.
U.S. Appl. No. 10/147,774, filed Dec. 2, 2010, Notice of Allowance.
U.S. Appl. No. 10/517,004, filed Nov. 23, 2010, Issue Notification.
U.S. Appl. No. 10/541,083, filed Dec. 1, 2010, Issue Notification.
U.S. Appl. No. 11/959,334, filed Nov. 10, 2010, Issue Notification.
U.S. Appl. No. 12/114,031, filed Nov. 22, 2010, Office Action.
U.S. Appl. No. 12/4003,256, filed Nov. 23, 2010, Issue Notification.
U.S. Appl. No. 11/048,503, filed Dec. 8, 2010, Issue Notification.
U.S. Appl. No. 12/393,877, filed Dec. 13, 2011, Office Action.
U.S. Appl. No. 12/941,809, filed Dec. 13, 2011, Restriction Requirement.
U.S. Appl. No. 12/955,859, filed Dec. 15, 2011, Office Action.
U.S. Appl. No. 12/338,977, filed Nov. 28, 2012, Office Action.
U.S. Appl. No. 12/961,331, filed Dec. 4, 2012, Office Action.
U.S. Appl. No. 13/030,922, filed Dec. 18, 2012, Office Action.
U.S. Appl. No. 12/402,398, filed Mar. 13, 2013, Notice of Allowance.
Turn—macmillandictionary.com/dictionary.american/turn.
Turn—Merriam-webster.com/dictionary/turn.
U.S. Appl. No. 11/396,141, filed Nov. 4, 2013, Notice of Allowance.
U.S. Appl. No. 11/411,925, filed Oct. 1, 2013, Office Action.
U.S. Appl. No. 11/532,325, filed Dec. 2, 2013, Office Action.
U.S. Appl. No. 11/852,190, filed Nov. 26, 2013, Office Action.
U.S. Appl. No. 12/106,928, filed Dec. 2, 2013, Office Action.
U.S. Appl. No. 12/106,937, filed Jan. 22, 2014, Office Action.
U.S. Appl. No. 12/122,603, filed Nov. 20, 2013, Office Action.
U.S. Appl. No. 12/403,277, filed Jan. 27, 2014, Office Action.
U.S. Appl. No. 12/642,319, filed Dec. 16, 2013, Office Action.
U.S. Appl. No. 12/688,065, filed Oct. 18, 2013, Office Action.
U.S. Appl. No. 12/941,809, filed Nov. 8, 2013, Office Action.
U.S. Appl. No. 12/961,331, filed Sep. 20, 2013, Advisory Action.
U.S. Appl. No. 12/987,792, filed Jan. 21, 2014, Office Action.
U.S. Appl. No. 13/030,922, filed Jan. 8, 2014, Notice of Allowance.
U.S. Appl. No. 13/052,634, filed Nov. 8, 2013, Office Action.
U.S. Appl. No. 13/112,618, filed Nov. 20, 2013, Office Action.
U.S. Appl. No. 13/112,631, filed Dec. 2, 2013, Office Action.
U.S. Appl. No. 13/153,594, filed Oct. 16, 2013, Notice of Allowance.
U.S. Appl. No. 13/308,227, filed Sep. 11, 2013, Office Action.
U.S. Appl. No. 13/791,829, filed Oct. 8, 2013, Notice of Allowance.
U.S. Appl. No. 13/898,202, filed Jan. 3, 2014, Office Action.
U.S. Appl. No. 13/222,899, filed Jan. 10, 2014, Office Action.
U.S. Appl. No. 14/246,926, filed Apr. 7, 2014, Carley et al.
U.S. Appl. No. 14/246,973, filed Apr. 1, 2014, Carley et al.
U.S. Appl. No. 11/113,549, filed Mar. 14, 2014, Notice of Allowance.
U.S. Appl. No. 11/411,925, filed Feb. 5, 2014, Notice of Allowance.
U.S. Appl. No. 11/674,930, filed Apr. 3, 2014, Notice of Allowance.
U.S. Appl. No. 11/852,190, filed Feb. 12, 2014, Notice of Allowance.
U.S. Appl. No. 12/106,928, filed Mar. 25, 2014, Advisory Action.
U.S. Appl. No. 12/113,851, filed Mar. 17, 2014, Office Action.
U.S. Appl. No. 12/114,031, filed Mar. 10, 2014, Office Action.
U.S. Appl. No. 12/684,569, filed Apr. 23, 2014, Office Action.
U.S. Appl. No. 12/688,065, filed Apr. 8, 2014, Office Action.
U.S. Appl. No. 12/848,642, filed Feb. 3, 2014, Notice of Allowance.
U.S. Appl. No. 12/941,809, filed Feb. 3, 2014, Notice of Allowance.
U.S. Appl. No. 12/950,628, filed Apr. 25, 2014, Notice of Allowance.
U.S. Appl. No. 12/961,331, filed Apr. 25, 2014, Notice of Allowance.
U.S. Appl. No. 14/323,753, Jul. 3, 2014, Fortson et al.
U.S. Appl. No. 11/113,549, Jul. 2, 2014, Issue Notification.
U.S. Appl. No. 11/411,925, Jun. 4, 2014, Issue Notification.
U.S. Appl. No. 11/674,930, Jul. 30, 2014, Issue Notification.
U.S. Appl. No. 11/852,190, Jun. 4, 2014, Issue Notification.
U.S. Appl. No. 11/958,295, Jun. 13, 2014, Notice of Allowance.
U.S. Appl. No. 12/122,603, Apr. 30, 2014, Office Action.
U.S. Appl. No. 12/393,877, Aug. 4, 2014, Notice of Allowance.
U.S. Appl. No. 12/608,773, Jul. 17, 2014, Office Action.
U.S. Appl. No. 12/642,319, May 27, 2014, Notice of Allowance.
U.S. Appl. No. 12/684,470, Jun. 4, 2014, Office Action.
U.S. Appl. No. 12/684,542, Jun. 18, 2014, Office Action.
U.S. Appl. No. 12/848,642, Jun. 4, 2014, Issue Notification.
U.S. Appl. No. 12/941,809, Jun. 4, 2014, Issue Notification.
U.S. Appl. No. 12/987,792, Jun. 11, 2014, Office Action.
U.S. Appl. No. 13/222,899, Jul. 31, 2014, Office Action.
U.S. Appl. No. 11/958,295, Oct. 8, 2014, Issue Notification.
U.S. Appl. No. 12/106,928, Oct. 3, 2014, Notice of Allowance.
U.S. Appl. No. 12/113,851, Aug. 21, 2014, Office Action.
U.S. Appl. No. 12/403,277, Aug. 15, 2014, Office Action.
U.S. Appl. No. 12/642,319, Sep. 24, 2014, Issue Notification.
U.S. Appl. No. 12/987,792, Aug. 25, 2014, Notice of Allowance.
U.S. Appl. No. 13/898,202, Aug. 21, 2014, Office Action.

* cited by examiner 200
210
210b
300
302a
304c'
304b'
304a'
304'
302
302b
211
202a
202
230a'
230b'
230'
230c'
202b 312
212
220

620
600
630
650
540
610
500
620b
620a
202
640b
320b
330b
640
320
330
640
200

APPARATUS AND METHOD FOR DELIVERING A CLOSURE ELEMENT

RELATED APPLICATION DATA

The present application claims priority under35 U.S.C. §119 to U.S. Provisional Application Ser. No. 60/693,531, naming Carly as the inventor, filed Jun. 24, 2006, entitled the same, and incorporated herein by reference in its entirety and for all purposes.

FIELD OF THE INVENTION

The present invention relates generally to apparatus and methods for closing and/or sealing openings through tissue, and more particularly to apparatus and methods for delivering a closure element for closing a puncture in a blood vessel or other body lumen formed during a diagnostic or therapeutic procedure.

BACKGROUND OF THE INVENTION

Catheterization and interventional procedures, such as angioplasty or stenting, generally are performed by inserting a hollow needle through a patient's skin and tissue into the vascular system. A guide wire may be advanced through the needle and into the patient's blood vessel accessed by the needle. The needle then is removed, enabling an introducer sheath to be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. Another technique has been suggested that involves percutaneously suturing the puncture site, such as that disclosed in U.S. Pat. No. 5,304,184, issued to Hathaway et al.

To facilitate positioning devices that are percutaneously inserted into a blood vessel, "bleed back" indicators have been suggested. For example, U.S. Pat. No. 5,676,974, issued to Kensey et al., discloses a bleed back lumen intended to facilitate positioning of a biodegradable plug within a puncture site. This device, however, requires that an anchor of the plug-be positioned within the vessel, and therefore, may increase the risk of over-advancement of the plug itself into the vessel.

Alternatively, U.S. Pat. No. 5,674,231, issued to Green et al., discloses a deployable loop that may be advanced through a sheath into a vessel. The loop is intended to resiliently expand to engage the inner wall of the vessel, thereby facilitating holding the sheath in a desired location with respect to the vessel.

Accordingly, apparatus and methods for delivering a device for closing a vascular puncture site or other opening through tissue would be useful.

SUMMARY OF THE INVENTION

The present invention is directed toward an apparatus and method for delivering a closure element through tissue and into an opening formed in, or adjacent to, a wall of a blood vessel or other body lumen of any size.

The delivery apparatus is configured to receive and retain the closure element such that the closure element is disposed substantially within the apparatus during advancement to the lumen opening. Thereby, if the apparatus is introduced via an introducer sheath, for example, the closure element can be disposed within, and delivered by way of, a lumen of the introducer sheath. The apparatus also is configured to engage the blood vessel wall adjacent to the opening and to position the closure element substantially adjacent to an outer surface of the blood vessel wall adjacent to the opening.

When properly positioned, the apparatus can be activated to distally deploy the closure element. During deployment, the apparatus preferably is configured to substantially uniformly expand the closure element beyond a natural cross-section of the closure element such that the closure element, when deployed, is configured to engage significant amount of the blood vessel wall and/or tissue. Engaging the blood vessel wall and/or tissue, the closure element is further configured to return to the natural cross-section. Thereby, the engaged blood vessel wall and/or tissue are drawn substantially closed and/or sealed, such that, for example, hemostasis within the opening is enhanced.

An apparatus is provided, hence, for delivering and deploying a resilient closure element to an opening formed in a body lumen. The closure element is configured to resiliently deform between a natural, substantially planar configuration to a substantially tubular configuration. Further, the closure element is configured to substantially radially displace between a reduced substantially tubular configuration and an expanded substantially tubular configuration having a greater cross-sectional dimension. The delivery apparatus includes a delivery assembly positionable through the tissue and into the opening in the body lumen. The assembly includes a distal locator portion and a carrier portion oriented proximal to the distal locator portion. The distal locator portion is configured to selectably engage the body lumen adjacent to the opening, and the carrier portion is configured to carry and support the closure element, in the reduced substantially tubular configuration. Further, the carrier portion is configured to urge the closure element toward the expanded substantially tubular configuration for deployment thereof. The closure element is oriented to engage the tissue when deployed in the expanded substantially tubular configuration, and to return toward the natural, substantially planar configuration such that the engaged tissue is drawn substantially closed.

In one specific embodiment, a cover member is included that protects the delivery assembly such that at least the carrier portion and the closure element, in the reduced substantially tubular configuration, are filly contained therein, in a support configuration. The cover member defines a lumen sized and dimensioned for relative axial sliding receipt of the delivery assembly therein for movement from the support configuration to a pre-deployment configuration. In the pre-deployment configuration, at least a distal portion of the closure element is exposed to enable radial expansion thereof by the carrier portion from the reduced in the reduced substantially tubular configuration to the expanded substantially tubular configuration.

In another specific embodiment, the distal portion of the cover member includes a plurality of substantially resilient extension members that are tapered radially inward. In the pre-deployment configuration, each extension member is configured to retain at least a proximal portion of the closure element against the carrier portion as the carrier portion is selectably moved from an unexpanded state to an expanded state. Consequently, the closure element is urged from the reduced substantially tubular configuration to the expanded substantially tubular configuration, for deployment thereof.

The carrier portion also preferably includes one or more expansion elements configured to expand substantially transversely with respect to a longitudinal axis of the carrier portion. Hence, the proximal carrier portion can be in the form of a proximal obturator, while the distal locator portion can also be essentially a distal obturator.

In yet another configuration, the distal obturator is selectively controlled by a locator control system coupled to a proximal end region of the delivery assembly. In particular, the locator control system selectively controls movement of the distal locator portion between the expanded state and the unexpanded state. Similarly, a carrier control system selectively controls movement of the carrier portion between the expanded state and the unexpanded state.

In one specific embodiment, a pusher member is included that is slideably disposed within the cover member. The pusher member includes a contact end region configured to distally displace the closure member longitudinally along the delivery assembly. The delivery assembly, the pusher member and the cover member are provided as a plurality of nested, telescoping members with a substantially common longitudinal axis. Further, the contact end region of the pusher member includes one or more longitudinal extensions extending distally therefrom. The extension are further r configured to expand radially as the distal end region of the pusher member moves distally and engages a distally-increasing transverse cross-sectional dimension of the carrier portion.

In another aspect of the present invention, a method is provided for closing an opening formed in a body lumen. The method includes extending a distal end region of a distal locator portion of a delivery apparatus through tissue into the opening in the body lumen, and engaging the body lumen adjacent to the opening. A carrier portion of the delivery apparatus is further positioned through the tissue adjacent to the opening. The carrier portion is proximally disposed relative to the locator portion, and the carrier portion, in an unexpanded state, is configured to support a resilient closure element, naturally in a substantially planar configuration, in a reduced substantially tubular configuration. The closure element is radially expanded from the reduced, substantially tubular configuration to an expanded, substantially tubular configuration, via the carrier portion. Subsequently, the closure element is distally deployed from the carrier portion, such that the closure element substantially uniformly expands to a cross-section that is greater than a natural cross-section of the closure element. The closure element then engages the tissue, and returns to the natural, planar configuration and the natural cross-section such that the tissue is drawn substantially closed.

BRIEF DESCRIPTION OF THE DRAWINGS

The assembly of the present invention has other objects and features of advantage that will be more readily apparent from the following description of the best mode of carrying out the invention and the appended claims, when taken in conjunction with the accompanying drawing, in which:

DETAILED DESCRIPTION OF THE PREFERRED EMBODIMENTS

Figure 1:
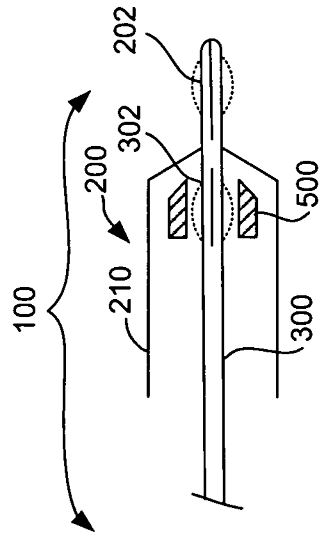
FIG. 1 provides a general illustration of an apparatus for closing openings formed in blood vessel walls in accordance with the present invention.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Figure 8A:
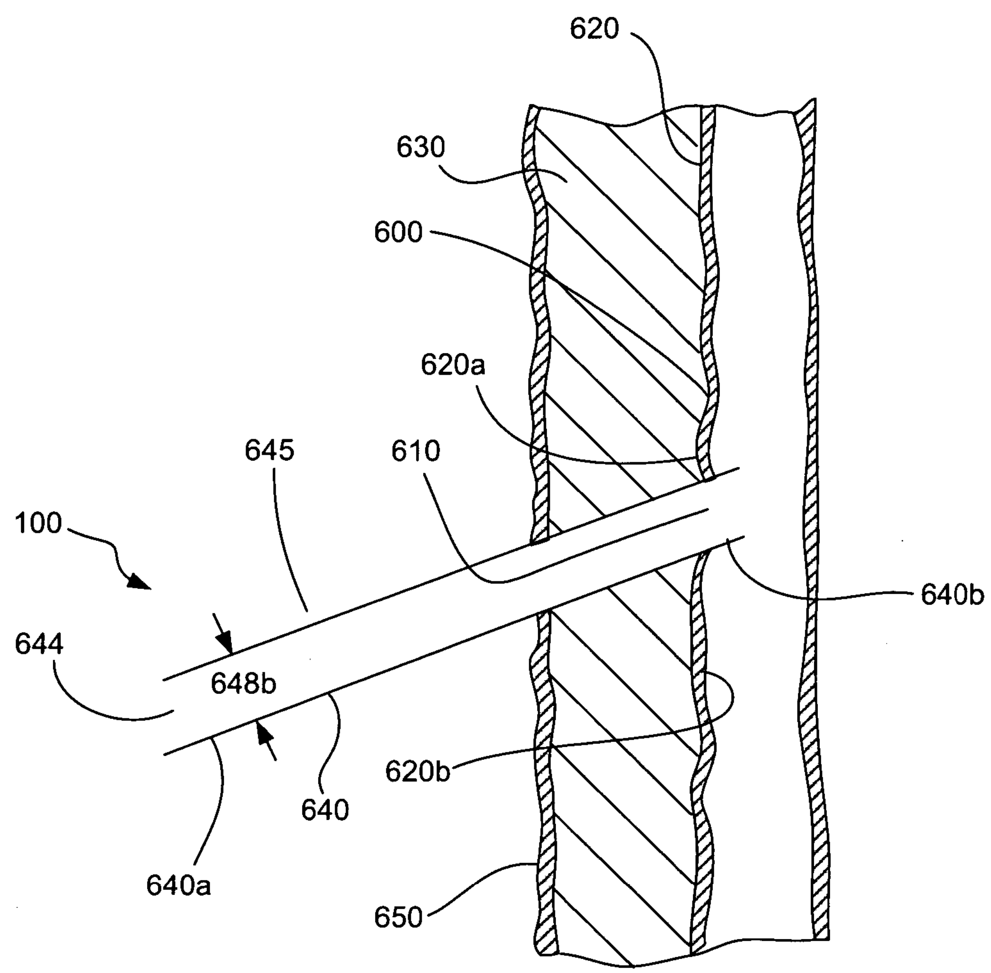
FIG. 8A illustrates a sheath that is positioned through tissue and into an opening formed in a wall of a blood vessel.
Figure 8C:
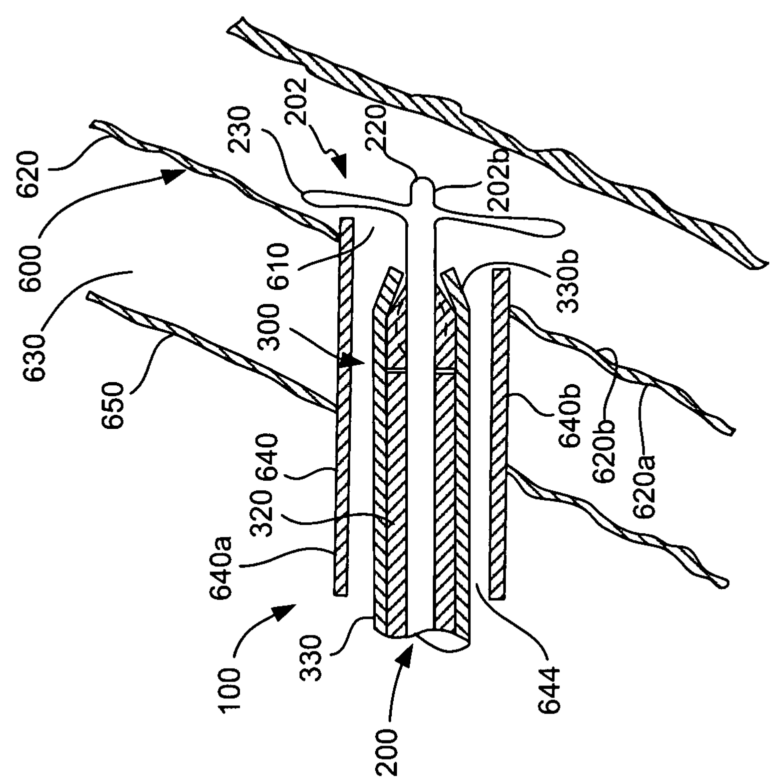
FIG. 8C illustrates a distal end region of the locator portion of FIG. 8B extending into the blood vessel and being transitioned into an expanded state.
Figure 8B:
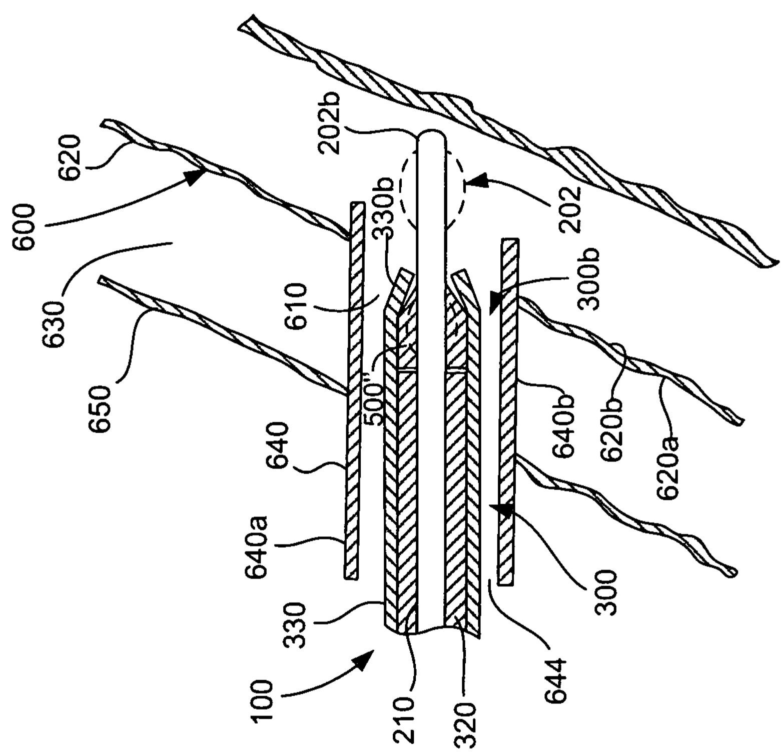
FIG. 8B illustrates the locator portion and the carrier portion of the delivery assembly of the apparatus being advanced distally into the blood vessel.
Figure 8E:
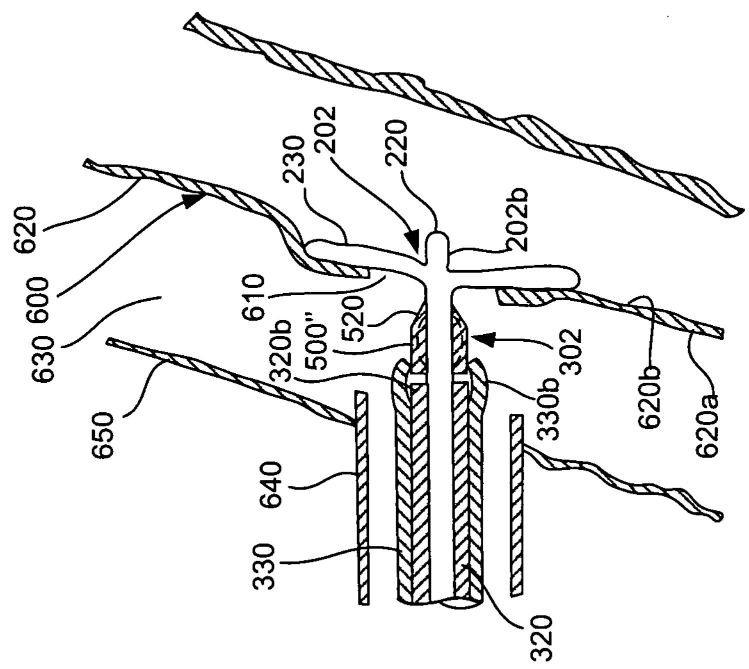
FIG. 8E illustrates a carrier portion of the apparatus of FIG. 8D with the cover member thereof being retracted to expose a portion of the closure element once the distal end region of FIG. 8D has engaged the inner surface of the blood vessel wall.
Figure 8D:
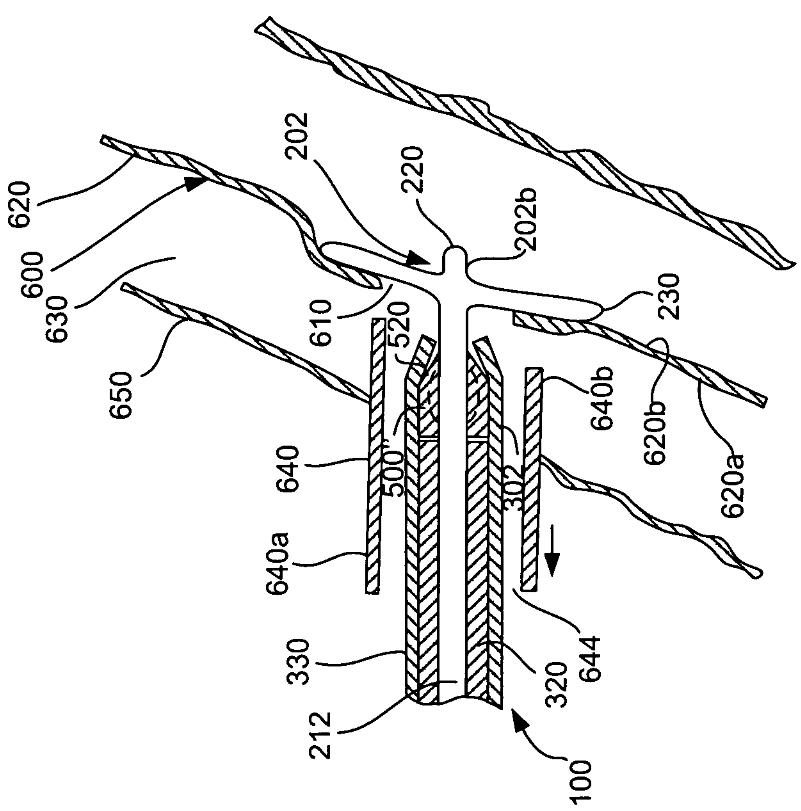
FIG. 8D illustrates the distal end region of the locator portion of FIG. 8C being retracted proximally to engage an inner surface of the blood vessel wall.
Figure 8F:
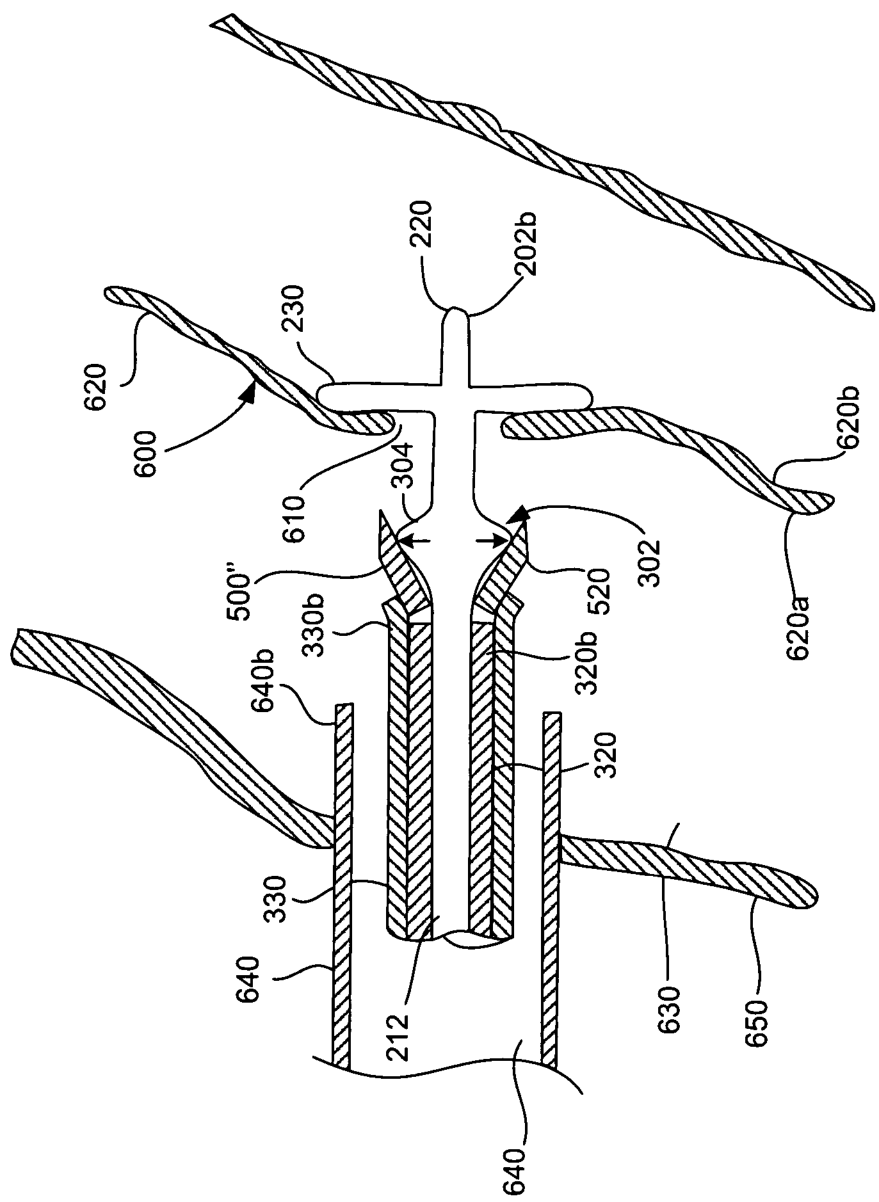
FIG. 8F illustrates a deployment device of the carrier portion of FIG. 8E being transitioned into an expanded state and beginning to distally deploy the closure element.
Figure 8G:
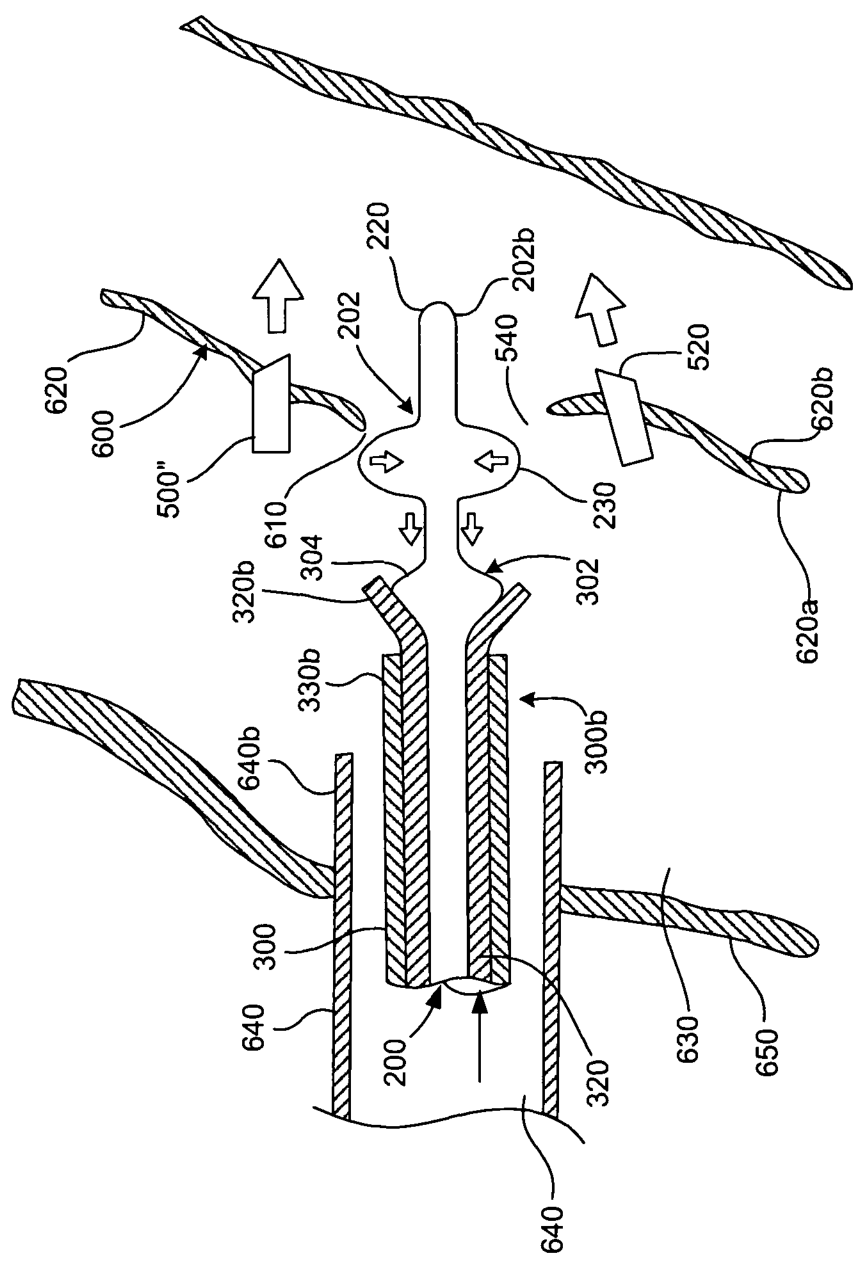
FIG. 8G illustrates the closure element of FIG. 8F upon being deployed and engaging tissue adjacent to the opening in the blood vessel wall.
Figure 8H:
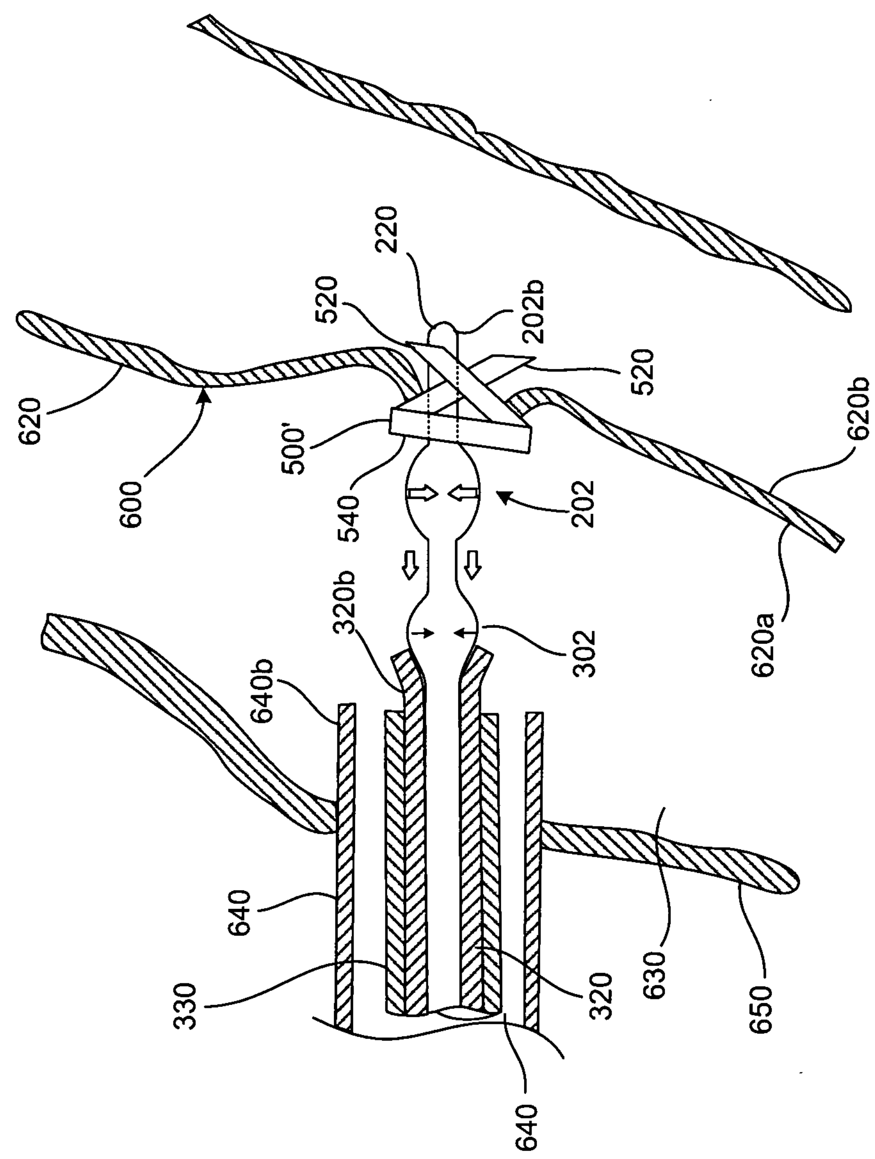
FIG. 8H illustrates the closure element of FIG. 8G transitioning from the substantially tubular configuration to the natural, planar configuration while engaging the engaged tissue.

Referring now generally to FIGS. 1-4 and 8A-8H, a clip or closure applier apparatus, generally designated 100, is provided for delivering and deploying a closure element 500 to an opening 610 formed in a body lumen, such as a blood vessel 600. Briefly, as shown in FIGS. 3A-3G, the closure element 500 is configured to resiliently deform between a natural, substantially planar configuration (FIG. 3A) to a substantially tubular configuration (FIG. 3F and 3G). Further, the closure element is configured to substantially radially displace between a reduced substantially tubular configuration (when mounted on the apparatus in a support configuration (FIG. 8B-8E) and an expanded substantially tubular configuration (FIG. 8F and 8G), having a greater cross-sectional dimension. The apparatus 100 includes a delivery assembly, generally designated 200, positionable through the tissue 630 and into the opening 610. The apparatus includes distal locator portion 202 and a carrier portion 300 oriented proximal to the distal locator portion. The distal locator portion 202 is configured to selectably engage the body lumen 600 adjacent to the opening 610 (FIGS. 8D and 8E), and the carrier portion 300 is configured to carry and support the closure element 500 in the reduced, substantially tubular configuration (FIG. 8B-8E), and further configured to urge the closure element 500 toward the expanded, substantially tubular configuration for deployment thereof (FIG. 8G). When deployed, the closure element 500 is oriented to engage the blood vessel wall 620 and/or the tissue 630 around the opening 610, and to return to the natural, substantially planar configuration and the natural cross-section such that the engaged tissue is drawn substantially closed (FIG. 8H).

Figure 2:
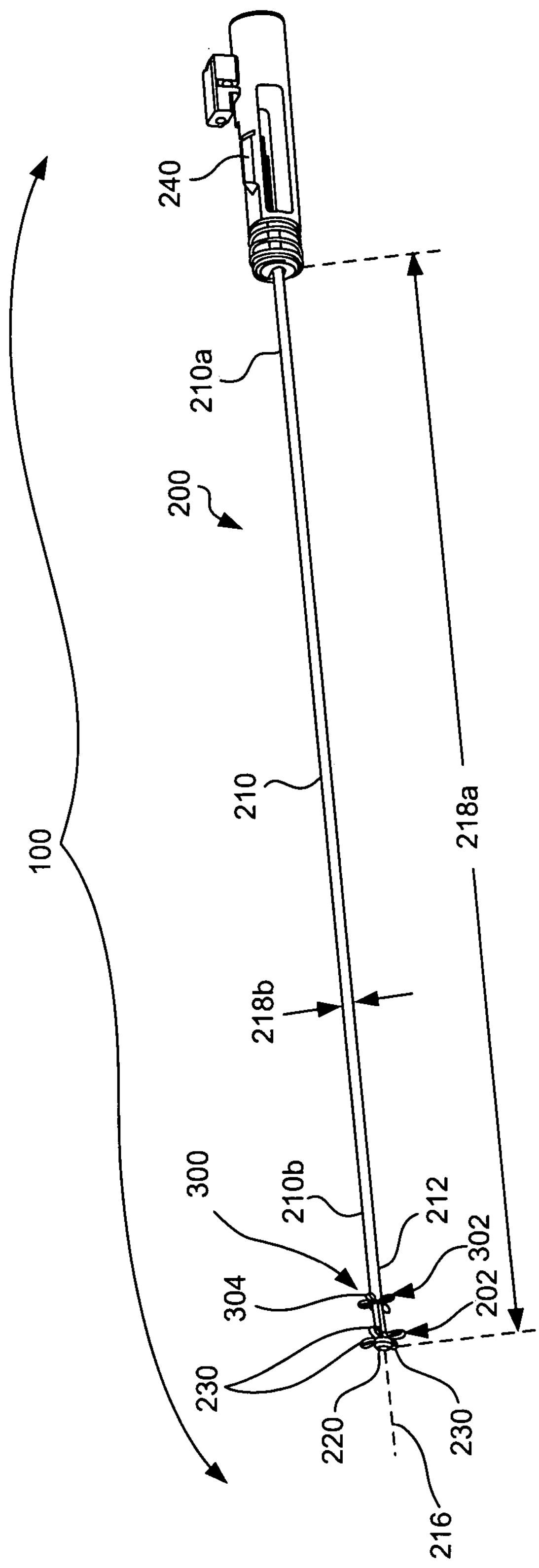
FIG. 2 illustrates one embodiment of a delivery assembly for the apparatus of FIG. 1.

Accordingly, the reduced complexity of the present inventive closure applier enables a diametric footprint that is significantly smaller than previous designs. Moreover, a closure applier apparatus is provided that fully encloses the closure element therein before deployment and delivery to the targeted vessel walls. This reduces potential tissue snag by the closure element during positioning. Hence, since the current apparatuses for sealing openings formed in blood vessel walls can snag tissue adjacent to the openings during positioning and may not provide an adequate seal, this apparatus, as well as co-pending U.S. patent application Ser. No. 10/356,214, filed Jan. 30, 2003, entitled "CLIP APPLIER AND METHODS OF USE" (hereinafter referred to as the '214 Patent Application), and herein incorporated by reference in its entirety, is configured to prevent inadvertent tissue contact during positioning and to engage a substantial amount of tissue adjacent to the opening. This proves much more desirable and provides a basis for a wide range of medical applications, such as diagnostic and/or therapeutic procedures involving blood vessels or other body lumens of any size. This result can be achieved, according to one embodiment of the present invention, by employing an apparatus 100 as shown in FIGS. 1 and 2.

Figure 3A:
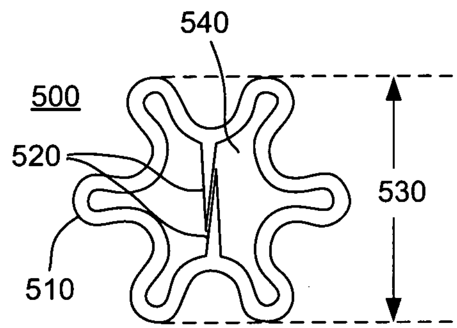
FIG. 3A illustrates a top view of one embodiment of a closure element in a natural, planar configuration and with a natural cross-section for use with the apparatus of FIG. 1.
Figure 3B:
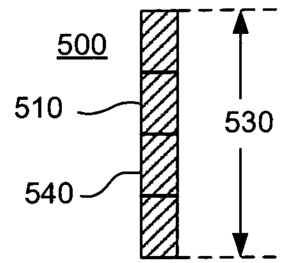
FIG. 3B illustrates a side view of the closure element of FIG. 3A.
Figure 3C:
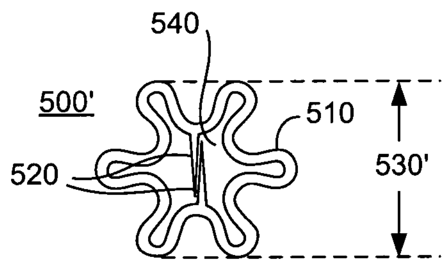
FIG. 3C illustrates a top view of the closure element of FIGS. 3A-3B after a natural cross-section of the closure element has been reduced.
Figure 3D:
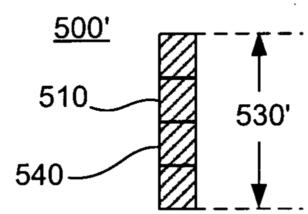
FIG. 3D illustrates a side view of the reduced closure element of FIG. 3C.
Figure 3E:
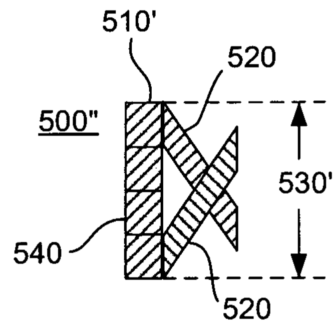
FIG. 3E illustrates a side view of the reduced closure element of FIGS. 3C-3D as the reduced closure element transitions from the natural, planar configuration to a tubular configuration.
Figure 3F:
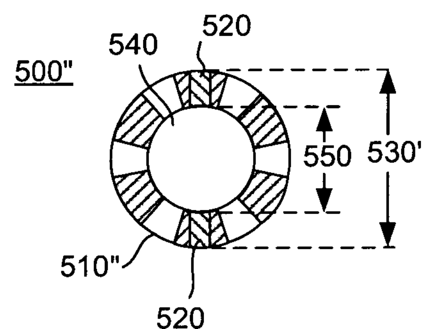
FIG. 3F illustrates a top view of the closure element of FIGS. 3C-3D upon completing the transition from the natural, planar configuration to a substantially tubular configuration.
Figure 3G:
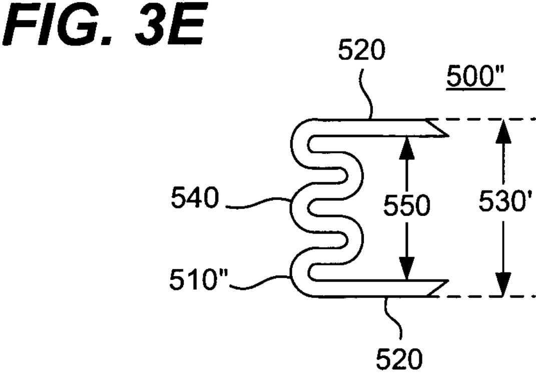
FIG. 3G illustrates a side view of the closure element of FIG. 3F.

As will be discussed in more detail below, the apparatus 100 can deliver a closure element 500 (shown in FIGS. 3A-B) through tissue 630 (shown in FIG. 8A) and into an opening 610 formed in and/or adjacent to a wall 620 of a blood vessel 600 or other body lumen. The closure element (or clip) 500 preferably has a generally annular-shape body 510 (shown in FIGS. 3A-3B) defining a channel 540 and one or more barbs and/or tines 520 for receiving and engaging the blood vessel wall 620 and/or the tissue 630 around the opening 610. Although the closure element 500 has a natural shape and size, the closure element 500 can be deformed into other shapes and sizes, as desired, and is configured to return to the natural shape and size when released. For example, the closure element 500 can have a natural, planar configuration with opposing tines 520 and a natural cross-section 530 as shown in FIGS. 3A-3B. The natural cross-section 530 of the closure element 500 can be reduced to form a reduced closure element 500' that has a natural, planar configuration with opposing tines 520 and a reduced cross-section 530' as shown in FIGS. 3C-3D. By rotating the opposing tines 520 axially as shown in FIG. 3E, the reduced closure element 500' can be further deformed to form a substantially tubular closure element 500" (shown in FIG. 3F). In this reduced, substantially tubular configuration with the tines 520 in an axial configuration (FIG. 3G which is the configuration when loaded on the carrier portion configuration), the resulting cross-section 530' is reduced as well.

Being configured to draw the blood vessel wall 620 and/or the tissue 630 adjacent to the opening 610 substantially closed and/or to enhance hemostasis within the opening 610, the closure element 500 can be formed from any suitable material, including any biodegradable material, any shape memory alloy, such as alloys of nickel-titanium, or any combination thereof. As desired, the closure element 500 can include radiopaque markers (not shown) or can be wholly or partially formed from a radiopaque material to facilitate observation of the closure element 500 using fluoroscopy or other imaging systems. Exemplary embodiments of a closure element are disclosed in U.S. Pat. No. 6,197,042, in co-pending application Ser. Nos.: 09/546,998, 09/610,238 and 10/081,726. The disclosures of these references and any others cited therein are expressly incorporated herein by reference.

The apparatus 100 is configured to receive and retain the closure element 500 such that the closure element 500 is disposed substantially within the apparatus 100. Thereby, if the apparatus 100 is introduced via an introducer sheath 640 (shown in FIG. 8A), for example, the closure element 500 can be disposed within, and delivered by way of, a lumen 644 (shown in FIG. 8A) of the introducer sheath 640. The apparatus 100 also is configured to engage the blood vessel wall 620 adjacent to the opening 610. Being disposed substantially within the apparatus 100, the closure element 500 can deeply penetrate, without inadvertently contacting, tissue 630 adjacent to the opening 610 such that the apparatus 100 can position the closure element 500 substantially adjacent to an outer surface 620*a* (shown in FIG. 8A) of the blood vessel wall 620 adjacent to the opening 610.

When properly positioned, the apparatus 100 can be activated to distally deploy the closure element 500. Although preferably configured to substantially uniformly expand the closure element 500 beyond the natural cross-section 530 of the closure element 500 during deployment, the apparatus 100, as desired, can deploy the closure element 500 without expanding the closure element 500. The closure element 500, when deployed, is configured to engage significant amount of the blood vessel wall 620 and/or tissue 630 adjacent to the opening 610. Engaging the blood vessel wall 620 and/or tissue 630, the closure element 500 is further configured to return to the natural cross-section 530. Thus, the engaged blood vessel wall 620 and/or tissue 630 are drawn substantially closed and/or sealed, such that, for example, hemostasis within the opening 610 is enhanced.

The apparatus 100 can be provided as one or more integrated components and/or discrete components. As shown in FIGS. 1 and 2, for example, the apparatus 100 can include an elongated delivery assembly 200 having a distal locator (or obturator) portion 202 and a carrier portion 300 that carries a closure element 500 thereon, in the reduced, substantially tubular configuration of FIGS. 8B-8E. For purposes of illustration, the locator portion 202 and the carrier portion 300 are shown in FIG. 1 as comprising substantially separate assemblies. As desired, however, the locator portion 202 and the carrier portion 300 each can be provided, in whole or in part, as one or more integrated assemblies.

Figures 4A, 4B:
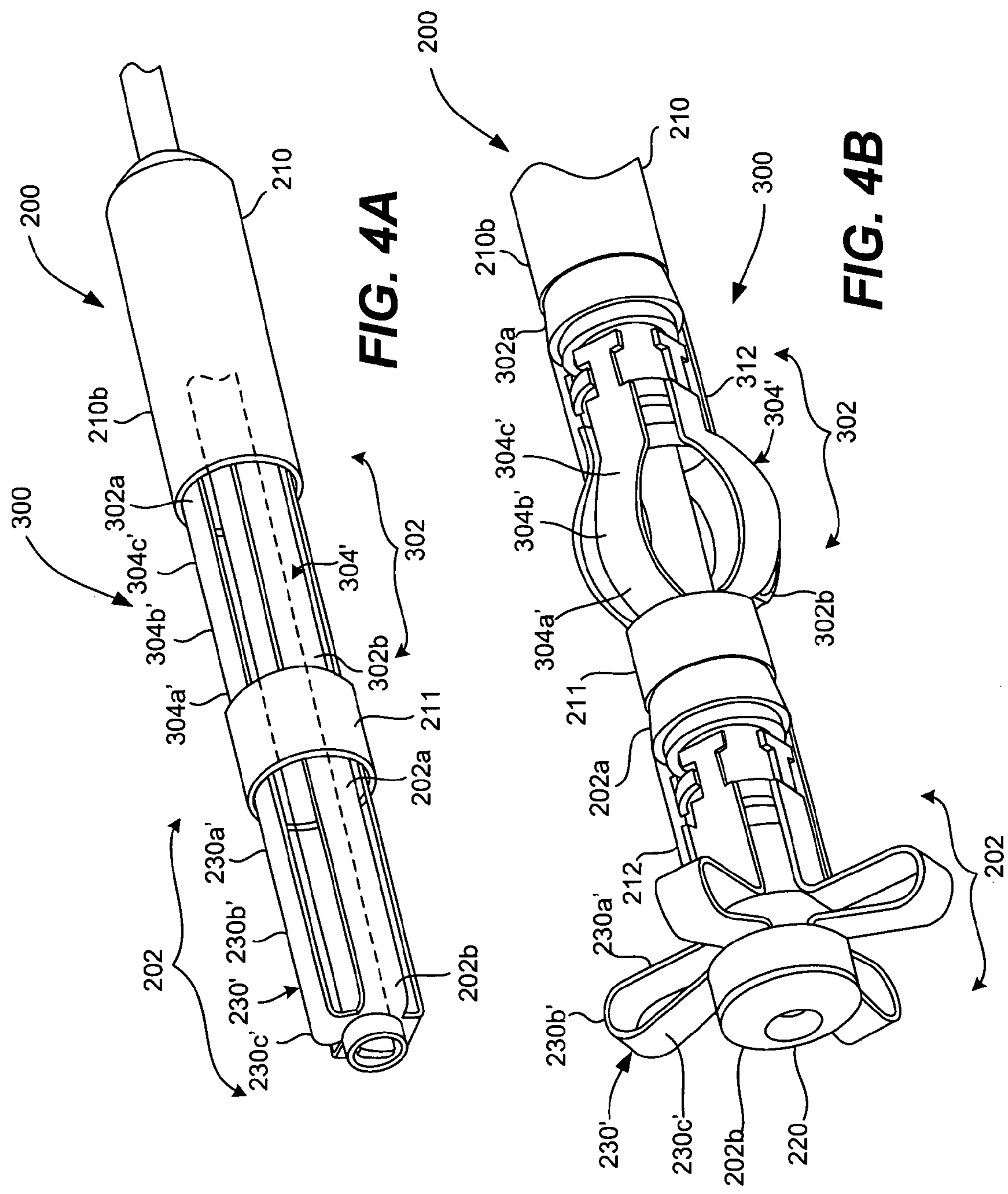
FIG. 4A illustrates one embodiment of a distal locator portion and a deployment device of a carrier portion of FIG. 2, both of which are illustrated in an unexpanded state.
FIG. 4B illustrates the distal locator portion and a deployment device of FIG. 4A, both of which are illustrated in an expanded state.

Being configured to extend into the opening 610, the locator portion 202 can selectably engage the inner surface 620*b* of the blood vessel wall 620 adjacent to the opening 610 (FIG. 8D). Thereby, the distal locator portion 202 is configured to draw the blood vessel wall 620 taut and can maintain the proper position of the apparatus 100 as the blood vessel 600 pulsates. The distal locator portion 202 can be provided in the manner disclosed in co-pending application Ser. Nos. 09/732,835 and 10/081,723, the disclosure of which is expressly incorporated herein by reference. Further, the delivery assembly 200 preferably includes a flexible, semi-rigid tubular, or rigid body 210, such as an elongate rail, with a longitudinal axis 216. As illustrated in FIG. 4A, the tubular body 210 has a proximal end region 210*a* and a distal end region 210*b* that supports the distal locator portion 202 and the carrier portion 300.

The tubular body 210 is preferably of a predetermined length 218*a* and a predetermined outer cross-section 218*b* (FIG. 2), both of which can be of any suitable dimension. The distal section of the distal locator portion 202 preferably includes a substantially rounded, soft, and/or flexible distal end or tip 220 to facilitate atraumatic advancement and/or retraction of the distal section into the blood vessel 600. As desired, a pigtail (not shown) may be provided on the distal end 220 to further aid atraumatic advancement of the delivery assembly 200.

The distal locator portion 202 further is selectably controllable between an unexpanded state (FIG. 4A) and an expanded state (FIG. 4B). In the unexpanded state, the distal locator portion 202 has an unexpanded size; whereas, the distal locator portion 202 in the expanded state has an expanded size, which is greater than the unexpanded size of the distal locator portion 202 in the unexpanded state. The distal locator portion 202 is configured to expand from the unexpanded size to the expanded size and/or to contract from the expanded size to the unexpanded size, and the expansion and contraction of the distal locator portion 202 preferably is substantially uniform about the longitudinal axis 216. For example, one or more expansion elements 230 can be provided on the distal locator portion 202 and can be configured to expand substantially transversely with respect to a longitudinal axis 216 of the locator portion 202. Preferably being substantially equally distributed about an outer periphery 212 of the distal locator portion 202, the expansion elements 230 may include radiopaque markers (not shown) or may be wholly or partially formed from a radiopaque material to facilitate observation of the expansion elements 230 and/or the distal locator portion 202 using fluoroscopy or other imaging systems.

At least one, and preferably all, of the expansion elements 230 of the distal locator portion 202 can comprise a substantially flexible member 230' with a substantially fixed end region 230*a*', an intermediate region 230*b*', and a movable end region 230*c*' as shown in FIGS. 4A-4B. For each substantially flexible member 230', the proximal fixed end region 230*a*' is fixedly coupled, relatively, with an intermediary support region 211 separating the distal locator portion 202 from the carrier portion 300. In contrast, the movable end region 230*c*' is movably coupled, relatively, with the intermediary support region 211, and configured to be axially movable relative to the fixed end region 230*a*'. When each movable end region 230*c*' is axially moved toward the relevant fixed end region 230*a*', the intermediate regions 230*b*' buckle and/or expand transversely outwardly, thereby transitioning the distal locator portion 202 of the delivery assembly 200 from the unexpanded state to the expanded state. In contrast, the distal locator portion 202 transitions from the expanded state to the unexpanded state as each of the movable end regions 230*c*' are axially moved away from the relevant fixed end region 230*a*'.

Hence, the expansion elements 230 are relatively resilient, and can buckle without plastic deformation or pure elastic deformation. Further, although the expansion elements 230 are shown as comprising the flexible members 230' in FIGS. 4A-4B for purposes of illustration, it is understood that the expansion elements 230 can comprise any type of expansion elements and are not limited to the illustrated embodiments. For example, inflatable bladder type devices or the like may be employed to cause expansion of the expansion elements, such as a balloon, an expandable mesh or a slit hypotube, etc. In a preferred embodiment, the flexible members are constructed of nitinol.

Figure 4C:
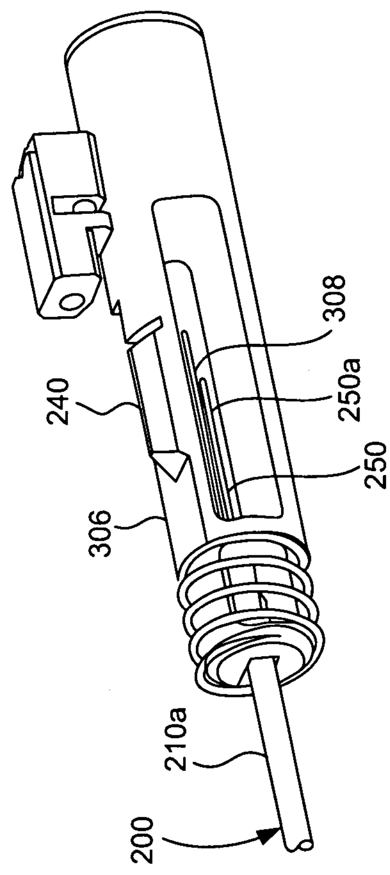
FIG. 4C illustrates one embodiment of a proximal end region of the delivery assembly of FIG. 2.

Turning to FIG. 4C, the locator portion 202 also can include a locator control system 240 that is coupled with the proximal end region 210*a* of the delivery assembly 200 and that is configured to selectively control the distal locator portion 202 between the unexpanded and expanded states. The locator control system 240 can selectively control the distal locator portion 202 between the unexpanded and expanded states, such as by being activated by a switching system (not shown). For example, a control member 250, such as a rod, wire, or other elongate member, can be moveably disposed within a lumen (not shown) formed by the tubular body 210 and extending substantially between the proximal end region 210*a* of the tubular body 210 and the distal locator portion 202. The control member 250 has a proximal end region 250*a* that is coupled with the locator control system 240, preferably through a control block (not shown, but operationally similar to the control systems and structures), and a distal end section (not shown) of the control member 250 that is coupled with the expansion elements 230, and/or the movable end regions 230*c*' of the substantially flexible members 230'. The locator control system 240 can selectively transition the expansion elements 230, and/or the substantially flexible members 230' of the distal locator portion 202 between the unexpanded and expanded states by moving the control member 250 axially relative to the tubular body 210.

The locator control system 240 preferably includes a locator release system (not shown, but one embodiment which may be similar to that disclosed in the '214 patent application) for maintaining the unexpanded state and/or the expanded state of the distal end region 210*b*, the expansion elements 230, and/or the substantially flexible members 230'. The locator release system is preferably configured to maintain the locator portion in the expanded state. Any type of locking system can be employed, and can be engaged, for instance, by activating the switching system. For example, once the substantially flexible members 230' have entered the expanded state, the locator release system can secure the control member 250 to prevent axial movement relative to the tubular body 210, thereby maintaining the substantially flexible members 230' in the expanded state.

The locator control system 240 also can be configured to disengage the locator release system, such that the distal end region 210*b*, the expansion elements 230, and/or the substantially flexible members 230' can transition between the unexpanded and expanded states. The locator release system can be disengaged, for example, by activating an emergency release system (not shown). As desired, the locator control system 240 can further include a biasing system (not shown), such as one or more springs, to bias the distal end region 210*b*, the expansion elements 230, and/or the substantially flexible members 230' to enter and/or maintain the unexpanded state when the locator release system 490 is disengaged.

Referring back to FIGS. 1 and 4, the delivery assembly 200 also includes the carrier portion 300 positioned along the tubular body 210, and oriented adjacent and proximate to the distal locator portion 202. The carrier portion 300 is configured to receive and retain the closure element 500 in the reduced, substantially tubular configuration (shown in FIG. 7B), which preferably is disposed substantially within and a cover member 330 of the carrier portion 300. When the locator portion 202 engages the inner surface 620*b* (shown in FIG. 8A) of the blood vessel wall 620, the carrier portion 300 is further configured to position the closure element 500 substantially adjacent to the opening 610 and to deploy the closure element 500. Upon being deployed, the closure element 500 can maintain the reduced cross-section 530' (shown in FIG. 7C) but preferably can temporarily and substantially uniformly expand beyond the natural cross-section 530 (shown in FIGS. 8F and 8G) of the closure element 500. In either case, the closure element 500, when deployed, can engage significant amount of the blood vessel wall 620 and/or tissue 630 adjacent to the opening 610. Thereafter, the closure element 500 is configured to return to the natural cross-section 530, preferably substantially uniformly, such that the blood vessel wall 620 and/or tissue 630 is drawn substantially closed and/or sealed (FIG. 8H).

Figure 5B:
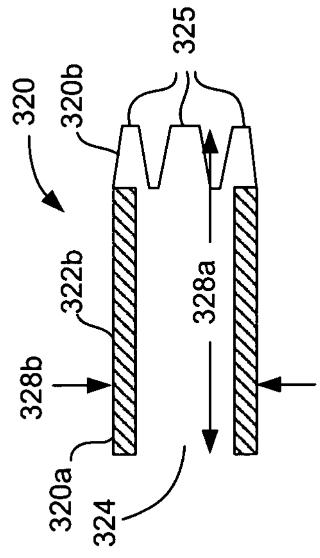
FIG. 5B illustrates one embodiment of a pusher member for the carrier portion of FIG. 5A.
Figure 5A:
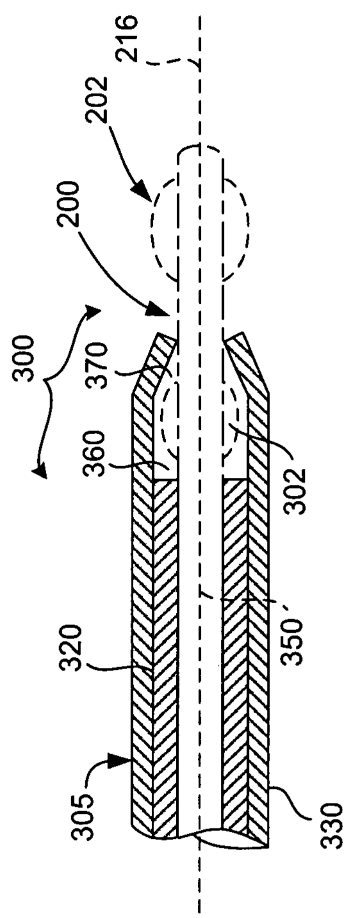
FIG. 5A illustrates one embodiment of a carrier portion for the apparatus of FIG. 1.
Figure 5C:
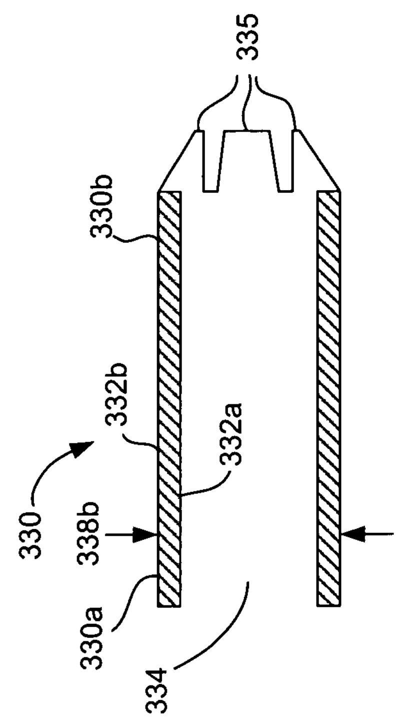
FIG. 5C illustrates one embodiment of a cover member for the carrier portion of FIG. 5A.

Turning now to FIGS. 5A-5C, the carrier portion 300 preferably includes a deployment device 302, a pusher member 320, and the cover member 330. The carrier portion 300, the pusher member 320 and the cover member 330 can be provided as a plurality of nested, telescoping members with a common longitudinal axis 350 of the tubular as illustrated in FIG. 5A. The deployment device 302 is configured to receive and support the closure element 500. While being disposed on the carrier portion 300, the closure element 500 preferably is deformed from the natural, planar configuration to form the substantially tubular closure element 500" (shown in FIGS. 3F-3G) as will be discussed in more detail below. Being disposed substantially about, and supported by, an outer periphery 312 of the deployment device 302, ), the closure element can be radially reduced in size and retained in place (FIGS. 8B-8E). In this arrangement, the substantially tubular closure element 500" can be substantially in axial alignment therewith with the tines 520 pointed substantially distally.

A biocompatible glue or adhesive may be applied to retain the resilient closure element 500" on the unexpanded deployment device 302 and loaded for deployment, in the reduced, substantially tubular configuration. Together with the compression properties of the cover member 330, the glue or adhesive must be sufficient to overcome the resilient tendency of the closure member 500" (FIG. 3G) to return to its natural planar condition 500 (FIGS. 3A and 3B). By way of example, such glues and embedded adhesives include polymer coatings, Loctite, etc. It will further be appreciated that other techniques can be applied to retain the closure element 500, in the reduced, substantially tubular configuration about the unexpanded deployment device 302.

As illustrated in FIGS. 4A and 4B, the deployment device 302 that supports the closure element 500 is configured to uniformly radially expand the reduced, substantially tubular closure element 500" beyond the natural cross-section 530 of the closure element 500 to prepare the substantially tubular closure element 500" for deployment (FIG. 8K). In some instances, however, the closure element 500 may be deployed without expanding the closure element 500. Thus, in this configuration, the carrier portion 300 will not be moved to the expanded position, maintaining a cross-section (not shown) that is substantially uniform and equal of that to the unexpanded distal locator portion 202. Accordingly, although shown and described as having the cross-section that increases distally for expanding the substantially tubular closure element 500", it will be understood that the carrier portion 300 can be provided with the substantially-uniform cross-section and that the substantially tubular closure element 500" can be deployed without being expanded.

Referring back to FIGS. 4A and 4B, in one specific embodiment, the expandable deployment device 302 of the carrier portion 300 is structurally similar to the expandable distal locator portion 202. Similar to the distal locator portion 202, the deployment device 302 is selectably controllable between an unexpanded state (FIG. 4A) and an expanded state (FIG. 4B). In the unexpanded state, the deployment device 302 has an unexpanded size that carries and supports the closure element 500" thereon, in the reduced, substantially tubular configuration shown in FIGS. 3G and 7C. The deployment device 302 in the expanded state has an expanded size, which is greater than the unexpanded size of the deployment device 302 in the unexpanded state. The deployment device 302 is configured to expand from the unexpanded size to the expanded size and/or to contract from the expanded size to the unexpanded size, and the expansion and contraction of the deployment device 302 preferably is substantially uniform about. the longitudinal axis 350, which incidentally when aligned with the distal locator portion 202, is substantially coaxial with its longitudinal axis 216. In the fully expanded state, the deployment device causes the closure element 500" to substantially uniformly expand to an expanded cross-sectional dimension (FIG. 8K) that is greater than a natural cross-sectional dimension (FIG. 3A).

More specifically, in one configuration, the deployment device is very similar to the distal locator portion 202 (or distal obturator) in that the deployment device 302 itself is in the form of a proximal obturator. As shown in FIG. 4B, the proximal obturator may include one or more expansion elements 304 that are configured to expand substantially transversely with respect to a longitudinal axis 350 of the carrier portion 300. Preferably being substantially equally distributed about an outer periphery 312 of the proximal obturator 302, the expansion elements 304 may similarly include radiopaque markers (not shown) or may be wholly or partially formed from a radiopaque material to facilitate observation of the expansion elements 304 and/or the proximal obturator 302 using fluoroscopy or other imaging systems.

At least one, and preferably all, of the expansion elements 304 of the proximal obturator 302 can comprise a substantially flexible member 304' with a substantially fixed end region 304*a*', an intermediate region 304*b*', and a movable end region 304*c*' as shown in FIGS. 4A and 4B. In contrast to the distal obturator 202, for each substantially flexible member 304', the fixed end region 304*a*' is oriented at distal end region 302*b* of the deployment device 302. The expansion elements fixed end region 304*a*' is fixedly coupled, relatively, to a proximal end of the intermediary support region 211 which incidentally is also fixedly coupled to a proximal end region 202*a* of the distal locator portion 202. The proximal movable end region 304*c*' of the flexible members 304', by comparison, is movably coupled with respect to the proximal end region 302*a* of the proximal obturator 302, and is configured to be axially movable relative to the fixed end region 304*a*'. This configuration enables the distal obturator to maintain a fixed relation to the vessel wall 620 when the distal locator portion 202 is in the expanded state, and the proximal obturator 302 is being operated.

When each movable proximal end region 304*c*' of the respective flexible member is axially moved toward the relevant fixed distal end region 304*a*', the intermediate regions 304*b*' buckle and/or expand transversely outwardly, thereby transitioning the proximal obturator 302 of the delivery assembly 200 from the unexpanded state to the expanded state. This causes the closure element 500" to expand toward the expanded substantially tubular configuration (FIG. 8G), spreading the opposed tines 520 during deployment to enable engagement with a wider area of the tissue 630 and/or blood vessel 600. Moreover, the closure element may also be caused to move closer to the distal locator portion 202. By comparison, the proximal obturator 302 transitions from the expanded state to the unexpanded state as each of the movable end regions 304*c*' are axially moved away from the relevant fixed end region 304*a'*.

Although the expansion elements 304 are shown as comprising the flexible members 304' in FIGS. 4A-4B for purposes of illustration, it is understood that the expansion elements 304 can also comprise any type of expansion elements and are not limited to the illustrated embodiments. As mentioned above, the expansion elements can be provided by inflatable bladder type devices or the like as well, such as a balloon, an expandable mesh or a slit hypotube, etc.

Similar to the locator portion, the carrier portion can also include a carrier control system 306 (FIG. 4C) that is coupled with the proximal end region 210*a* of the tubular body 210 of the delivery assembly 200, and that is configured to selectively control the proximal obturator 302 between the unexpanded and expanded states. The carrier control system 306 can selectively control the proximal obturator 302 between the unexpanded and expanded states, such as by being activated by a switching system (not shown). For example, a carrier control member 308 (adjacent locator control member 250), such as a rod, wire, or other elongate member, can be moveably disposed within a lumen (not shown) formed by the tubular body 210 and extending substantially between the tubular body proximal end region 210*a* and the proximal obturator 302. The carrier control member 308 includes a proximal end region 308*a* that is coupled to the carrier control system 306, preferably through a control block (not shown, but operationally similar to the control systems and structures described in the '214 Patent Application), and a distal end section (not shown) that is coupled to the expansion elements 304, and/or the movable end regions 304*c*' of the substantially flexible members 304'. The carrier control system 306 can selectively transition the expansion elements 304, and/or the substantially flexible members 304' of the proximal obturator 302 between the unexpanded and expanded states by moving the control member 308 axially relative to the tubular body 210.

The carrier control system 306 preferably includes a carrier release system (not shown) for maintaining the unexpanded state and/or the expanded state of the expansion elements 304, and/or the substantially flexible members 304' of the proximal obturator 302. While the release system is not shown, one similar to the locator release system above-mentioned, and as described in the '214 Patent Application may be provided.

The carrier control system 306 also can be configured to disengage the carrier release system, such that the expansion elements 304, and/or the substantially flexible members 304' can transition between the unexpanded and expanded states. The carrier release system can be disengaged, for example, by activating an emergency release system (not shown). As desired, the carrier control system 306 can further include a biasing system (not shown), such as one or more springs, to bias the expansion elements 304, and/or the substantially flexible members 304' to enter and/or maintain the unexpanded state when the carrier release system is disengaged.

Referring now to FIGS. 5A and 5B, when the substantially tubular closure element 500" is deployed, the pusher member 320 has a proximal end region 320*a* and a distal end region 320*b* and is coupled with, and slidable relative to, the carrier portion 300. The pusher member 320 includes a predetermined length 328*a* and a predetermined cross-section 328*b*, both of which can be of any suitable dimension. The pusher member is further configured to slidably receive at lease a portion of the deployment device 302, as well as the tubular body 210 therein, such that the distal end region 320*b* of the pusher member 320 is axially offset proximally from the distal end region 302*b* of the deployment device 302. This axial offset, hence, defines a space 360 that permits the positioning of the substantially tubular closure element 500" about the proximal obturator or deployment device 302.

The predetermined length 328*a* of the pusher member 320 can be greater than or substantially equal to the collective predetermined length 218*a* of the tubular body 210 and the carrier portion 300. The predetermined length 328*a* of the pusher member 320 however is preferably less than the collective predetermined length 218*a* of the tubular body 210 and the deployment device 302. In this manner, the deployment device 302 and the pusher member 320 at least partially define the space 360 distal to the distal end region 320*b* of the pusher member 320 and along the periphery 312 of the deployment device 302.

Being formed from a substantially rigid, semi-rigid, or flexible material, the pusher member 320 preferably is substantially tubular and can define a lumen 324 that extends substantially between the proximal end region 320*a* and the distal end region 320*b*. This lumen 324 is configured to slidably receive at least a portion of the tubular body 210 and the deployment device 302 therethrough. The cross-section 328*b* of the pusher member 320 preferably is substantially uniform, and the distal end region 320*b* of the pusher member 320 can comprise one or more longitudinal extensions 325, which extend distally from the pusher member 320 and along the periphery 312 of the deployment device 302, as shown in FIG. 5B. The longitudinal extensions 325 preferably are biased such that the longitudinal extensions 325 extend generally in parallel with common longitudinal axis 350. The longitudinal extensions 325 are sufficiently flexible to expand radially, and yet sufficiently rigid to inhibit buckling. Hence, to deploy the substantially tubular closure element 500" as the deployment device selectively expands from the unexpanded state to the expanded state, the distal end region 320*b* of the pusher member is directed distally along the deployment device 302 and engages the distally-increasing cross-section of the distal end region 302*b* of the deployment device 302.

Figure 7A:
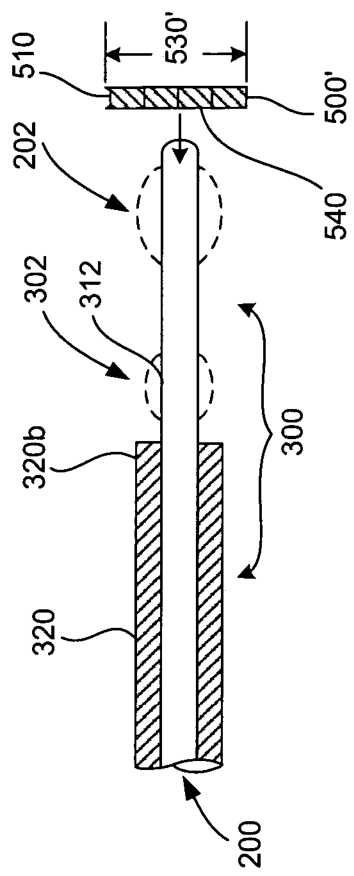
FIG. 7A illustrates the closure element of FIGS. 3A-3G prior to being disposed upon the carrier portion of FIG. 5A.
Figure 7B:
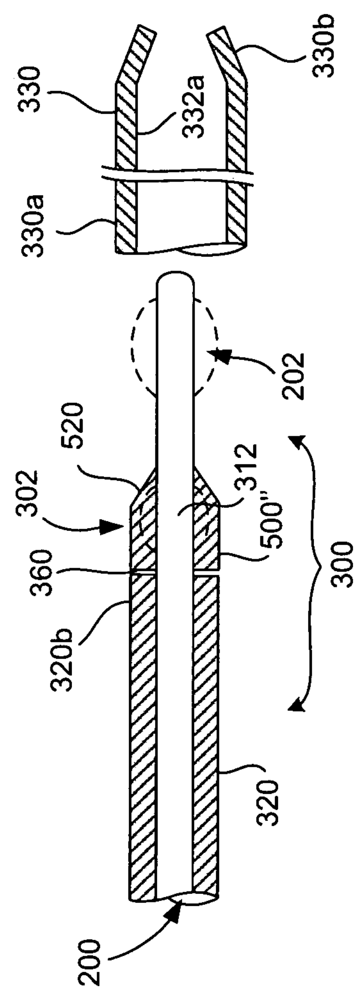
FIG. 7B illustrates the closure element of FIGS. 3A-3G upon being disposed upon the carrier portion of FIG. 5A, and further as the cover member of FIG. 5C receives the carrier portion.
Figure 7C:
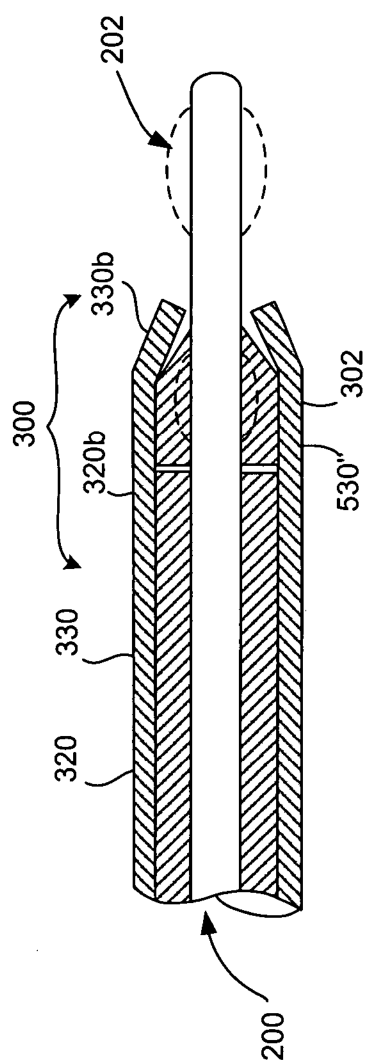
FIG. 7C illustrates the closure element of FIGS. 3A-3G being retained substantially within the carrier portion of FIG. 5A when the carrier portion is disposed substantially within the cover member of FIG. 3C.

As best shown in FIGS. 5A and 7C, the cover member 330 is configured to retain the substantially tubular closure element 500" and the carrier portion 300 substantially within a lumen 334 thereof prior to deployment. Being coupled with, and slidable relative to, the deployment device 302 and the pusher member 320, the cover member 330 has a proximal end region 330*a* and a distal end region 330*b* and includes a predetermined length 338*a* and a predetermined cross-section 338*b*, both of which can be of any suitable dimension. Preferably being formed as a substantially rigid, semi-rigid, or flexible tubular member formed from a polymer, the cover member 330 has an outer periphery 332*b* and an inner periphery 332*a* that defines lumen 334. The lumen 334 extends substantially between the proximal and distal end regions 330*a*, 330*b* of the cover member 330 and can be configured to slidably receive at least a portion of the pusher member 320. When the cover member 330 is properly positioned over the pusher member 320 and the deployment device 302, the distal end region 330*b* is configured to extend over the space 360, thereby defining an annular cavity 370 for receiving and retaining the closure element 500" in the reduced, substantially tubular configuration.

The cross-section 338*b* of the cover member 330 preferably is substantially uniform, and the distal end region 330*b* of the cover member 330 preferably comprises one or more longitudinal extensions 335, which extend distally from the cover member 330 and along an outer periphery 322*b* of the pusher member 320 as shown in FIG. 5C. Although the longitudinal extensions 335 can extend generally in parallel with common longitudinal axis 350, the longitudinal extensions 335 preferably are biased such that the plurality of longitudinal extensions 335 extend substantially radially inwardly as illustrated in FIGS. 5A and 5C. Thereby, the longitudinal extensions 335 can at least partially close the lumen 334 substantially adjacent to the distal end region 330*b* of the cover member 330. To permit the substantially tubular closure element 500" to be deployed from the annular cavity 370, the cover member 330 can be slideably retracted, relative the deployment device 302 to expose the mounted closure element 500". The longitudinal extensions 335 of the cover member 330 preferably are sufficiently flexible to expand radially to permit retractive movement of the distal end region 330*b* of the cover member 330 peripherally over the deployment device 302 and mounted closure element 500". This opens the annular cavity 370 such that the distal end region 330*b* of the cover member 330 no longer extends over the space 360.

If the carrier portion 300 is assembled as the plurality of nested, telescoping members as shown in FIG. 5A, the deployment device 302 and the tubular body 210 of the delivery assembly are least partially disposed within, and slidable relative to, the lumen 324 of the pusher member 320. The pusher member 320, in turn, is at least partially disposed within, and slidable relative to, the lumen 334 of the cover member 330. Hence, the longitudinal axis 216 of the locator portion 202, the carrier portion 300 and the tubular body 210 (i.e., of the delivery assembly 200) are preferably substantially in axial alignment with the common longitudinal axis of the pusher member 320 and the cover member 330.

Figure 6:
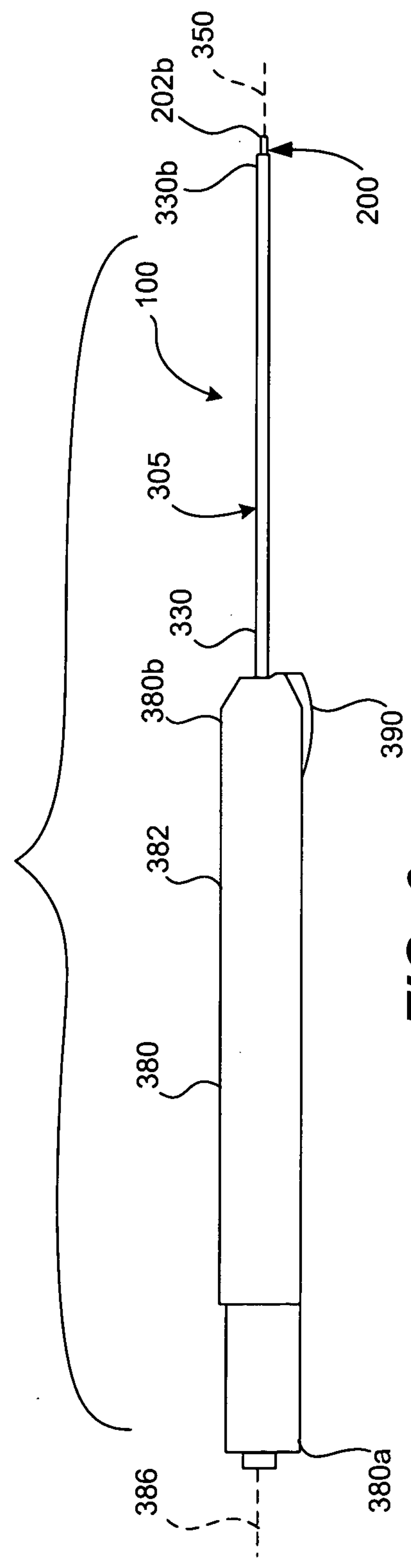
FIG. 6 illustrates a tube set and the delivery assembly of the apparatus of FIG. 1 mounted to a handle portion for operative manipulation thereof.

FIG. 6 best illustrates that the clip applier apparatus 100 includes a housing/handle 380 at a proximal end thereof suitable for gripping and manual support, manipulation and operation of the device and components thereof. Preferably, the housing is an elongated member with a longitudinal axis 386. When the apparatus 100 is properly assembled, the tube set 305 of the delivery assembly 200 is at least partially disposed within the housing handle such that the pusher member 320 and the cover member 330 are slidable relative to, the housing 380, and the tubular body, the carrier portion 300 and the distal locator portion 202 thereof. Further, respective distal end regions 210*b*, 320*b* and 330*b* extend from the distal end region 380*b* of the housing 380 such that the common longitudinal axis 350 (shown in FIG. 5A) of the tube set 305 is substantially axially aligned with the longitudinal axis 386 of the housing 380. Being configured to slidably retain the respective proximal end regions 210*a*, 320*a* and 330*a*, the housing 380 supports the tube set 305 and can have one or more handles 390 to facilitate use of the apparatus 100. The handles 390 extend substantially radially from the outer periphery 382 of the housing 380 and can be provided in the manner known in the art.

The present invention incorporates various switching systems, triggering systems, locking systems, etc. contained in the handle portion to effect use and operation of the delivery components described herein. While these subsystems are not shown and described herein in detail, it will be appreciated that they are similar to the design and operation of the analogous subsystems shown and described in our '214 Patent Application, which as mentioned is incorporated by reference herein for all purposes.

In use, the closure element 500" is carried on the deployment device 302, and disposed within the cover member 330. As shown in FIGS. 7A-7B, for example, the reduced closure element 500' can be slidably received over the distal locator portion 202 and the distal end region 300*b* of the carrier portion 300. The closure element 500 in the substantially tubular configuration is then seated and disposed about the periphery 312 of the deployment device 302 (e.g., the expansion elements 304 of the proximal obturator 302 in the unexpanded state) adjacent to the space 360.

To retain the reduced closure element 500" in the tubular configuration about the periphery of the carrier portion 300, the reduced diametric cross-section 530' of the reduced closure 500' is slightly less than or equal to the diametric cross-section 318*b* of the expansion elements 304 in the unexpanded state. Thus, to position the reduced closure element 500' on the deployment device 302, the reduced closure element 500' is temporarily radially deformed for receipt over the distal end region 302*b* of the deployment device 302. In addition, as the reduced closure element 500' is received over the distal end region 302*b*, the opposing tines 520 of the reduced closure element 500' engage the distal end region 302*b*. The reduced closure element 500' thereby forms the substantially tubular closure element 500" in the manner described in more detail above with reference to FIGS. 3E-3G.

After being received over the distal end region 302*b*, the substantially tubular closure element 500" is disposed about the space 360, and the tines 520 are directed substantially distally as shown in FIG. 7B. To improve the engagement between the closure element 500 (shown in FIGS. 3A-3B) and the blood vessel wall 620 and/or tissue 630 (collectively shown in FIG. 8A), the substantially tubular closure element 500" preferably is disposed on the deployment device 302 such that the tines 520 are contained in a plane.

Once disposed about the space 360, and together with the aforementioned glue or adhesive, the reduced, substantially tubular closure element 500" can be retained on the outer periphery 312 of the deployment device 302 when the distal end region 302*b* thereof and the distal end region 320*b* of the pusher member 320 are slidably received within the lumen 334 of the cover member 330 as illustrated in FIGS. 7B and 7C. When the cover member 330 is properly positioned over the carrier portion 300, the distal end region 330*b* of the cover member 330 extends over the space 360 and defines the annular cavity 370 for retaining the substantially tubular closure element 500". As such, the substantially tubular closure element 500" is disposed substantially between the outer periphery 312 of the delivery device 302 and the inner periphery 332*a* of the cover member 330 such that the substantially tubular closure element 500" maintains the substantially tubular configuration with the tines 520 being directed substantially distally. As desired, the tube set 305 may radially compress the substantially tubular closure element 500" such that the substantially tubular closure element 500" enters and maintains a compressed tubular configuration. The body 510 of the substantially tubular closure element 500" can be disposed distally of the distal end region 320*b* of the pusher member 320, as illustrated in FIGS. 7C, or can engage the distal end region 320*b*, as desired.

Turning now to FIG. 8A, an introducer sheath 640 may be inserted or otherwise positioned through skin 650 and tissue 630 and within the blood vessel 600 or other body lumen via the opening 610. Comprising a substantially flexible or semirigid tubular member, the sheath 640 has a proximal end region 640*a* and a distal end region 640*b* and includes a predetermined length and a predetermined cross-section, both of which can be of any suitable dimension. The sheath 640 also forms a lumen 644 that extends along a longitudinal axis of the sheath 640 and substantially between the proximal and distal end regions 640*a*, 640*b*. The lumen 644 can have any suitable internal cross-section 648*b* and is suitable for receiving one or more devices (not shown), such as a catheter, a guide wire, or the like. The lumen 644 is configured to slidably receive tube set 305 and the delivery assembly 200 of the apparatus 100, including the nested tubular body 210, the deployment device 302, the distal locator portion 202, pusher member 320 and the cover member 330 as a single unit. Accordingly, one significant advantage of the present invention is that, due to the reduced complexity of the cooperating componentry, the overall diametric footprint can be significantly smaller relative to the current systems. Hence, the entire nested tube set 305 may be slidably received in the lumen 644 of the introducer sheath 640 without requiring a radial expansion or splitting of the sheath 640. Such a configuration is beneficial in that, when required, the delivery assembly 200 can be retracted and reinserted unlike the previous designs that irreversibly radially expanded, stretched, split or severed the analogous sheaths.

The sheath 640 may be advanced over a guide wire or other rail (not shown) that was previously positioned through the opening 610 and into the blood vessel 600 using conventional procedures. In one specific use, the blood vessel 600 is a peripheral blood vessel, such as a femoral or carotid artery, although other body lumens may be accessed using the sheath 640 as will be appreciated by those skilled in the art. The opening 610, and consequently the sheath 640, may be oriented with respect to the blood vessel 600 such as to facilitate the introduction of devices through the lumen 644 of the sheath 640 and into the blood vessel 600 with minimal risk of damage to the blood vessel 600. One or more devices (not shown), such as a catheter, a guide wire, or the like, may be inserted through the sheath 640 and advanced to a predetermined location within the patient's body. For example, the devices may be used to perform a therapeutic or diagnostic procedure, such as angioplasty, atherectomy, stent implantation, and the like, within the patent's vasculature.

After the procedure is completed, the devices are removed from the sheath 640, and the apparatus 100 is prepared to be received by the lumen 644 of the sheath 640 as shown in FIG. 8B. Being in the unexpanded state, the distal end region 202*b* of the distal locator portion, via tubular body 210, is slidably received by the lumen 644 and atraumatically advanced distally into the blood vessel 600 (FIG. 8B). Briefly, it will be appreciated that, due to the fixed configuration between the distal end region 300*b* of the carrier portion 300 and the proximal end region 202*a* of the distal locator portion 202, in a support configuration, that the deployment device 302, the pusher member 320 and the cover member 330, together with the closure element in the reduced, substantially tubular configuration, are also advanced distally near the blood vessel 600 as a unit. Moreover, since the pusher member 320 and the cover member are also coupled to the tubular body 210, those components are likewise advanced distally together with the locator portion 202. Once the distal end region 202*b* of the distal locator portion 202 extends into the blood vessel 600, the distal locator portion 202 can transition from the unexpanded state to the expanded state as shown in FIG. 8C by activating the switching system of the locator portion 202.

Turning now to FIG. 8D, the apparatus 100 and the sheath 640 then are retracted proximally until the distal end region 202*b* of the locator portion 202 is substantially adjacent to an inner surface 620*b* of the blood vessel wall 620. The distal end region 202*b* of the locator portion 202 thereby draws the blood vessel wall 620 taut and maintains the proper position of the apparatus 100 as the blood vessel 600 pulsates. Since the expanded cross-section of the distal end region 202*b* is greater than or substantially equal to the cross-section of the opening 610 and/or the cross-section of the lumen 644, the distal end region 202*b* remains in the blood vessel 600 and engages the inner surface 620*b* of the blood vessel wall 620. The distal end region 202*b* can frictionally engage the inner surface 620*b* of the blood vessel wall 620, thereby securing the apparatus 100 to the blood vessel 600. The sheath 640 is retracted proximally such that the distal end region 640*b* of the sheath 640 is substantially withdrawn from the blood vessel 600, as shown in FIG. 8D, permitting the apparatus 100 to access the blood vessel wall 620.

As above-mentioned, the relative distance between the distal end region 300*b* of the carrier portion 300 and the proximal end region 202*a* of the distal locator portion 202 is fixed. Hence, once the distal end region 202*b* of the locator portion 202 properly engages the inner surface 620*b* of the blood vessel wall 620 as the expansion elements 230 are selectively positioned and moved to the expanded state, the carrier portion 300 is simultaneously axially positioned adjacent the opening 610, at a first predetermined position (FIG. 8D), where the closure element 500" can be prepared for deployment. More particularly, upon establishing the first predetermined position, the deployment device 302 and the loaded reduced closure element 500", in the reduced, substantially tubular configuration, are disposed proximal and substantially adjacent to the outer surface 620*a* of the blood vessel wall 620. In this manner, the blood vessel wall 620, adjacent to the opening 610, is disposed substantially between the expanded distal region 202*b* of the locator portion 202 and the distal end region 300*b* of the carrier portion 300.

Once the first predetermined position is established, the carrier portion 300 can be manipulated to deploy the closure element. Initially, the cover member 330 is proximally retracted to a pre-deployment position, relative to the distal locator portion 202, the deployment device 302 and the pusher member 320, which are to remain axially substantially stationary, in order to expose at least a portion of the closure element. This is performed by decoupling the cover member 330 from the deployment device 302, the distal locator portion 202, and the pusher member 320, all of which are preferably inhibited from axial relative movement.

As best shown in FIG. 8E, as the cover member 330 is retracted proximally, relative the carrier portion 300, toward the pre-deployment configuration, the distal end region 300*b* of the cover member 330 moves proximally such that the cover member 330 no longer encloses the annular cavity 370. In this configuration, the space 360 and at least a portion of the closure element 500" (e.g., the tines 520) are exposed through an opening into lumen 334 of the cover member 330. Thereby, the substantially tubular closure element 500" is not completely enclosed by the annular cavity 370 formed by the distal end regions 320*b* and 330*b* of the pusher member 320 and the cover member 330, respectively.

Although not completely enclosed by the annular cavity 370, the substantially tubular closure element 500" is advantageously retained on the outer periphery 312 of the deployment device 302 by the distal end region 330*b* of the cover member 330 as illustrated in FIG. 8E. For example, the longitudinal extensions 335 of the cover member 330 resiliently contact at least a portion of the closure element, in the reduced tubular configuration, by an amount sufficient to maintain the closure element 500" on the deployment device 302 during movement thereof from the unexpanded state to the expanded state. By retaining the proximal portion of the substantially tubular closure element 500" between the distal end region 330*b* (e.g., the radially, inwardly directed longitudinal extensions 335) of the cover member 330 and the distal end region 202*b* of the deployment device 302, the apparatus 100 is configured to provide better tissue penetration for the closure element 500".

Moreover, the timing between the deployment of the substantially tubular closure element 500" by the carrier portion 300, and the retraction and transition to the unexpanded state by the locator portion 202 and the deployment device 302 likewise are facilitated because the substantially tubular closure element 500" is retained between the cover member distal end region 330*b* and the deployment device distal end region 202*b*. Further, the deployment device 302 and the cover member 330 operate to maintain the substantially tubular closure element 500" in the tubular configuration.

Referring back to FIG. 8E, once the cover member 330 is properly retracted to expose the tines 520 of the closure member 500", in the pre-deployment configuration, the cover member is recoupled to the delivery assembly 200 so as to be maintained axially substantially stationary relative the deployment device 302 and the distal locator portion 202. The deployment device 302 can then transition from the unexpanded state to the expanded state, as shown in FIG. 8F, by activating the switching system of the carrier portion 300. This causes the closure element 500", in the reduced substantially tubular configuration, to expand radially outward toward the expanded substantially tubular configuration for deployment thereof.

In one embodiment where the deployment device 302 is in the form of a proximal obturator, by way of example, when the switching system is actuated, the wire 308 (FIG. 4C) causes the movable expansion elements 304 to retract, thereby collectively radially expanding the expansion elements 304. Since portions of the closure element 500" (E.g., the tines 520) are adhered and/or resiliently retained about the periphery 312 of the expansion elements 304 of the deployment device 302, as the expansion elements 304 move toward the expanded state, the closure element 500" is caused to radially expand. In particular, the cross-section 530' (shown in FIGS. 3F-3G) of the reduced, substantially tubular closure element 500" begins to radially expand, preferably in a substantially radially uniform manner with the expansion of the deployment device to the expanded state (FIG. 8F).

By axially positioning the distal tips of the tines 520 of the closure element 500" at or near the region of greatest radial expansion of the expansion elements 304, such as for example the intermediate regions 304*b*' of the substantially flexible members 304' of the proximal obturator 302, the distal tips of the tines are caused to be radially displaced outward at least as much as any other portion of the closure element in the tubular configuration. As the expansion elements 304 of the deployment device 302 are caused to fully expand, in the expanded state, the distal tips of the closure element tines 520 are oriented in a direction radially outward from the longitudinal axis 350 of the deployment device to increase the area of tissue engagement. Further, the cross-section 530' of the substantially tubular closure element 500" radially expands beyond natural cross-section 530 (shown in FIGS. 3A-3B) of the closure element 500, placing the tube set in condition to deploy the closure element 500" (FIG. 8F).

Once the carrier portion 300 is moved to the expanded state, a lock system of the carrier portion may retain the expansion elements 304 in the expanded state for deployment of the closure element. To deploy the closure element 500" in the expanded substantially tubular configuration, the pusher member 320 decouples from the delivery assembly 200 and the cover member 330. Therefore, the carrier portion 300, the locator portion 202 and the cover member 330 preferably are inhibited from further axial movement and remain substantially stationary, relative the handle portion; whereas, the pusher member 320 remains axially slidable.

As the pusher member 320 selectively continues distally, the distal end region 320*b* of the pusher member 320 engages the substantially tubular closure element 500" and displaces the substantially tubular closure element 500" from the space 360. Since the space 360 is substantially radially exposed, the pusher member 320 directs the substantially tubular closure element 500" over the expanded cross-section of the deployment device expansion elements 304 such that the cross-section 530' (shown in FIGS. 3F-3G) of the substantially tubular closure element 500" continues to radially expand, preferably in a substantially uniform manner. As the substantially tubular closure element 500" traverses over the expanded cross-section of the deployment device expansion elements 304, in the expanded state, the closure element is advanced distally and completely out of the radially inward grasp of the distal end region 300*b* of the cover member 330. Further, the cross-section 530' of the substantially tubular closure element 500" radially expands beyond natural cross-section 530 (shown in FIGS. 3A-3B) of the closure element 500. As mentioned and as shown in FIG. 8F, in some configurations, the tips of the distally facing tines 520 may be directed radially outward, enabling the closure element to engage a larger area of tissue.

Upon being directed over the distally-increasing cross-section of the expansion elements 304 of deployment device 302 by the pusher member 320, the substantially tubular closure element 500" is distally deployed as illustrated in FIG. 8G. When the substantially tubular closure element 500" is deployed, the tines 520 can pierce and otherwise engage significant amount of the blood vessel wall 620 and/or tissue 630 adjacent to the opening 610. For example, the tines 520 can engage significant amount of the blood vessel wall 620 and/or tissue 630 because the cross-section 530' of the substantially tubular closure element 500" is expanded beyond natural cross-section 530 of the closure element 500 during deployment.

The proximal end region 202*a* of the locator portion 202 also begins to retract proximally and a locator release system (not shown) can be activated to transition from the expanded state to the unexpanded state as the substantially tubular closure element 500" is deployed as shown in FIG. 8G. Simultaneously, the distal end region 300*b* of the carrier portion 300 also begins to retract proximally and a carrier release system (not shown) can be activated to transition from the expanded state to the unexpanded state. Preferably, the distal end regions 202*b*, 300*b* of the locator portion 202 and carrier portion 300 retract proximally and transition from the expanded state to the unexpanded state substantially simultaneously with the deployment of the substantially tubular closure element 500".

As desired, the distal end region 210*b* of the tubular body 210 may be configured to draw the blood vessel wall 620 and/or tissue 630 adjacent to the opening 610 proximally and into the channel 540 defined by the substantially tubular closure element 500". The tines 520 of the substantially tubular closure element 500" thereby can pierce and otherwise engage the drawn blood vessel wall 620 and/or tissue 630. Since the cross-section 530' of the substantially tubular closure element 500" is expanded beyond natural cross-section 530 of the closure element 500, a significant amount of the blood vessel wall 620 and/or tissue 630 can be drawn into the channel 540 and engaged by the tines 520.

Figure 8I:
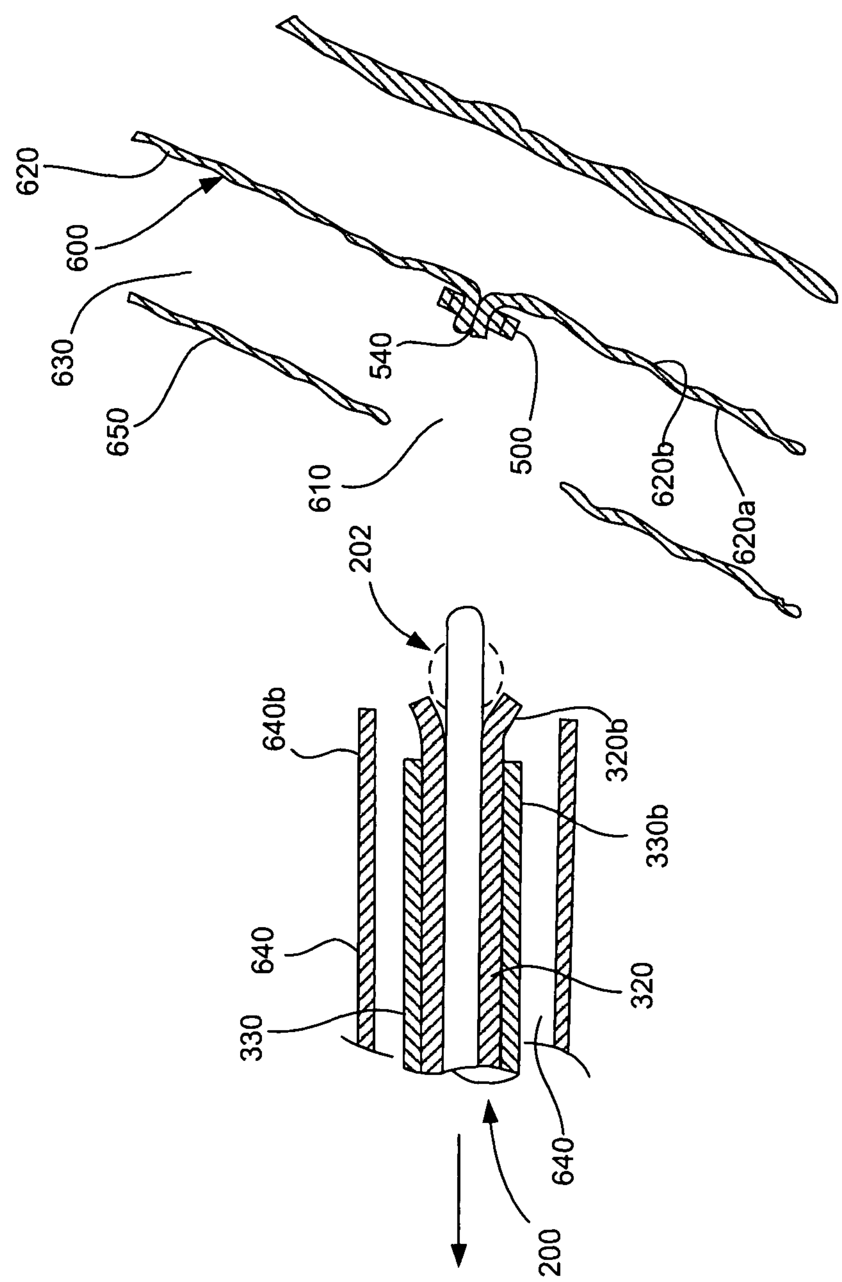
FIG. 8I illustrates the closure element of FIG. 8H drawing the engaged tissue substantially closed and/or sealed

Turning to FIG. 8H, the substantially tubular closure element 500", once deployed, begins to transition from the tubular configuration, returning to the natural, planar configuration with opposing tines 520 and a natural cross-section 530 of the closure element 500. Preferably, the substantially tubular closure element 500" substantially uniformly transitions from the tubular configuration to the natural, planar configuration. Rotating axially inwardly to form the opposing tines 520 of the closure element 500, the tines 520 draw the tissue 630 and/or vessel wall 620 into the channel 540 as the substantially tubular closure element 500" forms the closure element 500. In addition, the tissue 630 is drawn substantially closed and/or sealed as the cross-section 530' of the substantially tubular closure element 500" contracts to return to the natural cross-section 530 of the closure element 500. Thereby, the opening 610 in the blood vessel wall 620 can be drawn substantially closed and/or sealed via the closure element 500 as illustrated in FIG. 8I.

The invention is susceptible to various modifications, alternative forms and uses, and specific examples thereof have been shown by way of example in the drawings and are herein described in detail. For instance, while the present invention has been primarily described for use in vessel closure, it will be appreciated that the present invention may be suitable for other repair applications as well, such as for patent foramina ovalia (PFO) application. Other modifications may include a guide wire lumen so that the distal ends may be positioned over a guide wire as well. It should be understood, however, that the invention is not to be limited to the particular forms or methods disclosed, but to the contrary, the invention is to cover all modifications, equivalents, and alternatives falling within the spirit and scope of the claims.

What is claimed is:

1. An apparatus for delivering and deploying a closure element to an opening formed in a body lumen, said apparatus comprising: a closure element configured to resiliently deform between a natural, substantially planar configuration to a substantially tubular configuration, and further configured to substantially radially displace between a reduced substantially tubular configuration and an expanded substantially tubular configuration having a greater cross-sectional dimension; and a delivery assembly positionable through said tissue and into said opening in the body lumen, and having a distal locator portion and a carrier portion oriented proximal to said distal locator portion, each of said distal locator portion and said carrier portion being supported by a support member and being selectively expandable to an expanded state and selectively contracted from said expanded state to an unexpanded state around the support member, a proximal end of the distal locator portion and a distal end of the carrier portion being fixed to an intermediate support region disposed at the distal end of the delivery assembly, said distal locator portion being configured to selectably engage said body lumen adjacent to said opening, and said carrier portion being configured to carry and support said closure element, in the reduced substantially tubular configuration with said carrier portion in said unexpanded state, and further configured to urge said closure element toward the expanded substantially tubular configuration for deployment thereof when said carrier portion is selectively expanded to said expanded state, wherein said closure element is oriented to engage said tissue when deployed in the expanded substantially tubular configuration, and to return toward said natural, substantially planar configuration such that the engaged tissue is drawn substantially closed.

2. The apparatus of claim 1, further including:

a cover member protecting said delivery assembly such that at least said carrier portion and said closure element, in the reduced substantially tubular configuration, are fully contained therein, in a support configuration.

3. The apparatus of claim 2, wherein said cover member defines a lumen sized and dimensioned for relative axial sliding receipt of said delivery assembly therein from the support configuration to a predeployment configuration, exposing at least a distal portion of said closure element to enable radial expansion thereof by said carrier portion from the reduced substantially tubular configuration to the expanded substantially tubular configuration, for deployment thereof.

4. The apparatus of claim 3, wherein a distal portion of said cover member is biased and tapered radially inward.

5. The apparatus of claim 4, wherein said distal portion of said cover member includes a plurality of substantially resilient extension members tapered radially inward.

6. The apparatus of claim 5, wherein in said pre-deployment configuration, each extension member is configured to retain at least a proximal portion of the closure element against the carrier portion as said carrier portion is selectably moved from said unexpanded state to said expanded state urging said closure element from the reduced substantially tubular configuration to the expanded substantially tubular configuration, for deployment thereof.

7. The apparatus of claim 6, wherein said carrier portion includes one or more expansion elements configured to expand substantially transversely with respect to a longitudinal axis of the carrier portion to said expanded state.

8. The apparatus of claim 1, wherein said distal locator portion includes a distal obturator selectably controllable between an unexpanded state and an expanded state for engaging said body lumen.

9. The apparatus of claim 8, wherein in said unexpanded state, said distal locator portion has a transverse cross-sectional dimension less than that of said opening, and in said expanded state, said distal locator portion has a transverse cross-sectional dimension greater than or substantially equal to that of said opening.

10. The apparatus of claim 8, wherein said distal obturator includes one or more expansion elements configured to expand substantially transversely with respect to a longitudinal axis of the distal locator portion.

11. The apparatus of claim 8, further including:

a locator control system coupled to a proximal end region of said delivery assembly, said locator control system being configured to selectively control said distal locator portion between said expanded state and said unexpanded state.

12. The apparatus of claim 1, wherein said carrier portion includes a proximal obturator selectably controllable between an unexpanded state and an expanded state urging said closure element from the reduced substantially tubular configuration to the expanded substantially tubular configuration, for deployment thereof.

13. The apparatus of claim 12, wherein said proximal obturator includes one or more expansion elements configured to expand substantially transversely with respect to a longitudinal axis of the carrier portion.

14. The apparatus of claim 13, further including:

a carrier control system coupled to a proximal end region of said delivery assembly, said carrier control system being configured to selectively control said carrier portion between said expanded state and said unexpanded state.

15. The apparatus of claim 2, further including:

a pusher member slideably disposed within said cover member, said pusher member including a contact end region configured to distally displace said closure member longitudinally along said delivery assembly.

16. The apparatus of claim 15, wherein said delivery assembly, said pusher member and said cover member are provided as a plurality of nested, telescoping members with a substantially common longitudinal axis.

17. The apparatus of claim 16, wherein said contact end region of said pusher member includes one or more longitudinal extensions extending distally and being configured to expand radially as said distal end region of said pusher member moves distally and engages a distally-increasing transverse cross-sectional dimension of said closure element on said carrier portion.

18. The apparatus of claim 1, wherein said distal locator portion has a first transverse dimension and said carrier portion has a second transverse dimension, said first transverse dimension being greater than said second transverse dimension.

19. A system for closing an opening formed in a body lumen, comprising:

a superelastic closure element configured to resiliently deform between a natural, substantially planar configuration to a substantially tubular configuration, and further configured to substantially radially displace between a reduced substantially tubular configuration and an expanded substantially tubular configuration, having a greater cross-sectional dimension, said apparatus comprising:

a delivery assembly positionable through said tissue and into said opening in the body lumen, and having a distal locator portion and a carrier portion oriented proximal to said distal locator portion, each of said distal locator portion and said carrier portion being supported by a tubular member and being individually selectively expandable to an expanded state and selectively contracted from said expanded state to an unexpanded state through proximal and distal movement of respective control members extending longitudinally within a lumen of the tubular member, a proximal end of the distal locator portion being fixed relative to a distal end of the carrier portion by an intermediate support region, the proximal end of the distal locator portion and the distal end of the carrier portion being fixed to the intermediate support reach, each of the distal locator portion and the carrier portion including one or more expansion elements, said distal locator portion being configured to selectably engage said body lumen adjacent to said opening, and said carrier portion being disposed proximal to the distal locator portion by a fixed distance during insertion and deployment, said carrier portion being configured to carry and support said closure element, in the reduced substantially tubular configuration, and further configured to urge said closure element toward the expanded substantially tubular configuration for deployment thereof; and a cover member protecting said delivery assembly such that at least said carrier portion and said closure element, in the reduced substantially tubular configuration, are fully contained therein, in a support configuration;

said carrier portion including a proximal obturator selectably controllable between said unexpanded state and said expanded state urging said closure element from the reduced substantially tubular configuration to the expanded substantially tubular configuration, for deployment thereof; and a pusher member slideably disposed within said cover member, said pusher member including a contact end region configured to distally displace said closure element longitudinally along said delivery assembly, said contact end region of said pusher member including one or more longitudinal extensions extending distally and being configured to expand radially as said distal end region of said pusher member moves distally and engages a distally-increasing transverse cross-sectional dimension of said closure element on said carrier portion, wherein said closure element is oriented to engage said tissue when deployed in the expanded substantially tubular configuration, and to return toward said natural, substantially planar configuration such that the engaged tissue is drawn substantially closed.

20. The system of claim 19, wherein said cover member defines a lumen sized and dimensioned for relative axial sliding receipt of said delivery assembly therein from the support configuration to a predeployment configuration, exposing at least a distal portion of said closure element to enable radial expansion thereof by said carrier portion from the reduced in the reduced substantially tubular configuration to the expanded substantially tubular configuration, for deployment thereof.

21. The system of claim 20, wherein said distal portion of said closure element includes two or more tines distally directed, in the substantially tubular condition.

22. The system of claim 21, wherein a distal portion of said cover member is biased and tapered radially inward.

23. The system of claim 22, wherein said distal portion of said cover member includes a plurality of substantially resilient extension members tapered radially inward.

24. The system of claim 23, wherein in said pre-deployment configuration, each extension member is configured to retain at least a proximal portion of the closure element against the carrier portion as said carrier portion is selectably moved from said unexpanded state to said expanded state, urging said closure element from the reduced substantially tubular configuration to the expanded substantially tubular configuration, for deployment thereof.

25. The system of claim 19, wherein said distal locator portion includes a distal obturator selectably controllable between said unexpanded state and said expanded state for engaging said body lumen.

26. The system of claim 25, wherein in said unexpanded state, said distal locator portion has a transverse cross-sectional dimension less than that of said opening, and in said expanded state, said distal locator portion has a transverse cross-sectional dimension greater than or substantially equal to that of said opening.

27. The system of claim 19, wherein said one or more expansion elements of said distal locator portion are configured to expand substantially transversely with respect to a longitudinal axis of the distal locator portion, and said one or more expansion elements of said carrier portion are configured to expand substantially transversely with respect to a longitudinal axis of the carrier portion.

28. The system of claim 27, further including:

a locator control system coupled to a proximal end region of said delivery assembly, said locator control system being configured to selectively control said distal locator portion between said expanded state and said unexpanded state; and a carrier control system coupled to a proximal end region of said delivery assembly, said carrier control system being configured to selectively control said carrier portion between said expanded state and said unexpanded state.

29. A method for closing an opening formed in a body lumen, comprising: extending a distal end region of a distal locator portion of a delivery apparatus through tissue into the opening in the body lumen; engaging said body lumen adjacent to said opening; positioning a carrier portion of the delivery apparatus through said tissue adjacent to said opening, said carrier portion being oriented proximal to said distal locator portion, a proximal end of said distal locator portion and a distal end of said carrier portion being fixed to an intermediate support region disposed at a distal end of the delivery assembly, each of said distal locator portion and said carrier portion being supported by a support member and being selectively expandable to an expanded state and selectively contracted from the expanded state to an unexpanded state around said support member, said carrier portion, in an unexpanded state being configured to support a closure element that resiliently deforms between, a natural, substantially planar configuration to a substantially tubular configuration; radially expanding the closure element from the reduced, substantially tubular configuration to an expanded, substantially tubular configuration, via the carrier portion; and urging said closure element toward the expanded substantially tubular configuration with said carrier portion when said carrier portion is selectively expanded to said expanded state; distally deploying said closure element from said carrier portion such that said closure element substantially uniformly expands to a cross-section that is greater than a natural cross-section of said closure element, engages said tissue, and returns to said natural, planar configuration and said natural cross-section such that said tissue is drawn substantially closed.

* * * * *